United States Patent
Sainsbury et al.

(10) Patent No.: US 10,822,613 B2
(45) Date of Patent: *Nov. 3, 2020

(54) PROTEIN EXPRESSION SYSTEMS

(71) Applicant: PLANT BIOSCIENCE LIMITED, Norwich, Norfolk (GB)

(72) Inventors: Frank Sainsbury, Norfolk (GB); George Peter Lomonossoff, Norfolk (GB)

(73) Assignee: PLANT BIOSCIENCE LIMITED, Norwich, Norfolk (GB)

(*) Notice: Subject to any disclaimer, the term of this patent is extended or adjusted under 35 U.S.C. 154(b) by 0 days.

This patent is subject to a terminal disclaimer.

(21) Appl. No.: 15/674,881

(22) Filed: Aug. 11, 2017

(65) Prior Publication Data

US 2018/0030462 A1 Feb. 1, 2018

Related U.S. Application Data

(60) Division of application No. 14/172,301, filed on Feb. 4, 2014, now abandoned, which is a continuation of application No. 12/812,165, filed as application No. PCT/GB2009/000060 on Jan. 8, 2009, now Pat. No. 8,674,084.

(30) Foreign Application Priority Data

Jan. 8, 2008 (GB) .................................. 0800272.7

(51) Int. Cl.
*C12N 15/82* (2006.01)

(52) U.S. Cl.
CPC ..... *C12N 15/8216* (2013.01); *C12N 15/8203* (2013.01); *C12N 15/8257* (2013.01); *C12N 15/8258* (2013.01)

(58) Field of Classification Search
None
See application file for complete search history.

(56) References Cited

U.S. PATENT DOCUMENTS

| 8,674,084 | B2 | 3/2014 | Sainsbury et al. |
| 2010/0287670 | A1 | 11/2010 | Sainsbury et al. |
| 2014/0250549 | A1 | 9/2014 | Sainsbury et al. |

FOREIGN PATENT DOCUMENTS

| WO | WO 01/96569 | 12/2001 |
| WO | WO 2007/135480 | 11/2007 |
| WO | WO 2009/087391 | 7/2009 |
| WO | 2015/103704 A1 | 7/2015 |
| WO | 2015/143567 A1 | 10/2015 |

OTHER PUBLICATIONS

Canizares, M.C. et al., "A bipartite system for the constitutive and inducible expression of high levels of foreign proteins in plants," Plant Biotech. J. (2006) 4(2):183-193.
Dinesh-Kumar, S.P. et al., "Control of start codon choice on a plant viral RNA encoding overlapping genes," Plant Cell (1993) 5(6):679-692.
Genbank Accession No. X00729 (1983).
Gleave, Plant Mol. Biol. (1992) 20:1203-1207.
Holness, C.L. et al., "Identification of the initiation codons for translation of cowpea mosaic virus middle component RNA using site-directed mutagenesis of an infectious cDNA clone," Virology (1989) 172(1):311-320.
Kozak, M., "Pushing the limits of the scanning mechanism for initiation of translation," Gene (2002) 299(1-2):1-34.
Liu, L. et al., "Cowpea mosaic virus-based systems for the production of antigens and antibodies in plants," Vaccine (2005) 23(15):1788-1792.
Matsuda, D. et al., "Expression of the two nested overlapping reading frames of turnip yellow mosaic virus RNA is enhanced by a 5' cap and by 5' and 3' viral sequences," J. Virol. (2004) 78(17):9325-9335.
Macfarlane et al., Virology (2000) 267:29-35.
Pouwels et al., J. Gen. Virol. (2003) 84:3485-3494.
Rohll, J.B. et al., "3'-terminal nucleotide sequences important for the accumulation of cowpea mosaic virus M-RNA," Virology (1993) 193(2):672-679.
Sainsbury, F. et al., "Expression and multiple proteins using full-length and deleted versions of cowpea mosaic virus RNA-2," Plant Biotech. J. (2008) 6(1):82-92.
Sainsbury, F. et al., "Extremely high-level and rapid transient protein production in plants without the use of viral replication," Plant Physiol. (2008) 148(3):1212-1218.
Weiland, J.J. et al., "Infectious TYMV RNA from cloned cDNA: effects in-vitro and in vivo of point substitutions in the initiation codons of two extensively overlapping ORFs," Nucl. Acids Res. (1989) 17(12):4675-4688.
Wellink, J. et al., "Mutational analysis of AUG codons of cowpea mosaic virus M RNA," Biochimie (1993) 75(8):741-747.
International Search Report and Written Opinion for Application No. PCT/GB2009/000060 dated May 7, 2009 (13 pages).
United States Patent Office Action for U.S. Appl. No. 12/812,165 dated Apr. 11, 2012 (28 pages).
United States Patent Office Final Rejection for U.S. Appl. No. 12/812,165 dated Dec. 18, 2012 (11 pages).
United States Patent Office Notice of Allowance for U.S. Appl. No. 12/812,165 dated Oct. 28, 2013 (14 pages).

*Primary Examiner* — Matthew R Keogh
(74) *Attorney, Agent, or Firm* — Duane Morris LLP; Thomas J. Kowalski; Deborah L. Lu

(57) ABSTRACT

The invention is based on an expression enhancer sequence derived from the RNA-2 genome segment of a bipartite RNA virus, in which a target initiation site in the RNA-2 genome segment has been mutated. Deletion of appropriate start codons upstream of the main RNA2 translation initiation can greatly increase in foreign protein accumulation without the need for viral replication. Also provided are methods, vectors and systems, including the 'hyper-translatable' Cowpea Mosaic Virus ("CPMV-HT") based protein expression system.

13 Claims, 23 Drawing Sheets

Specification includes a Sequence Listing.

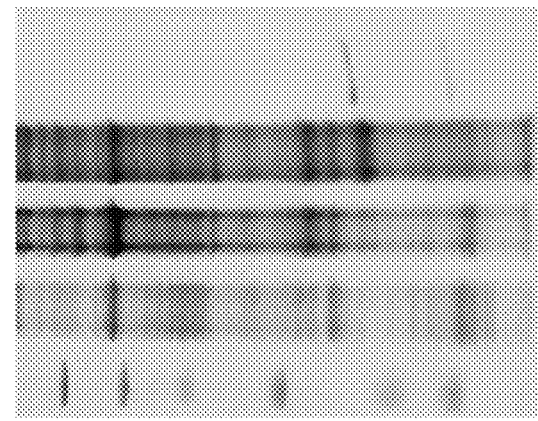
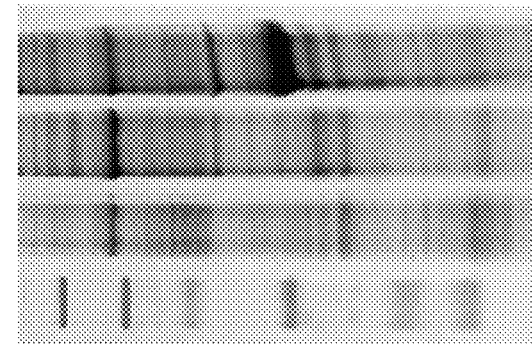
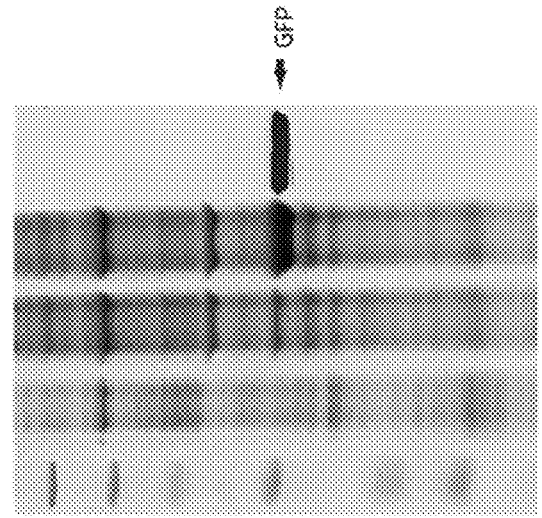
FIGURE 4 CONT'D

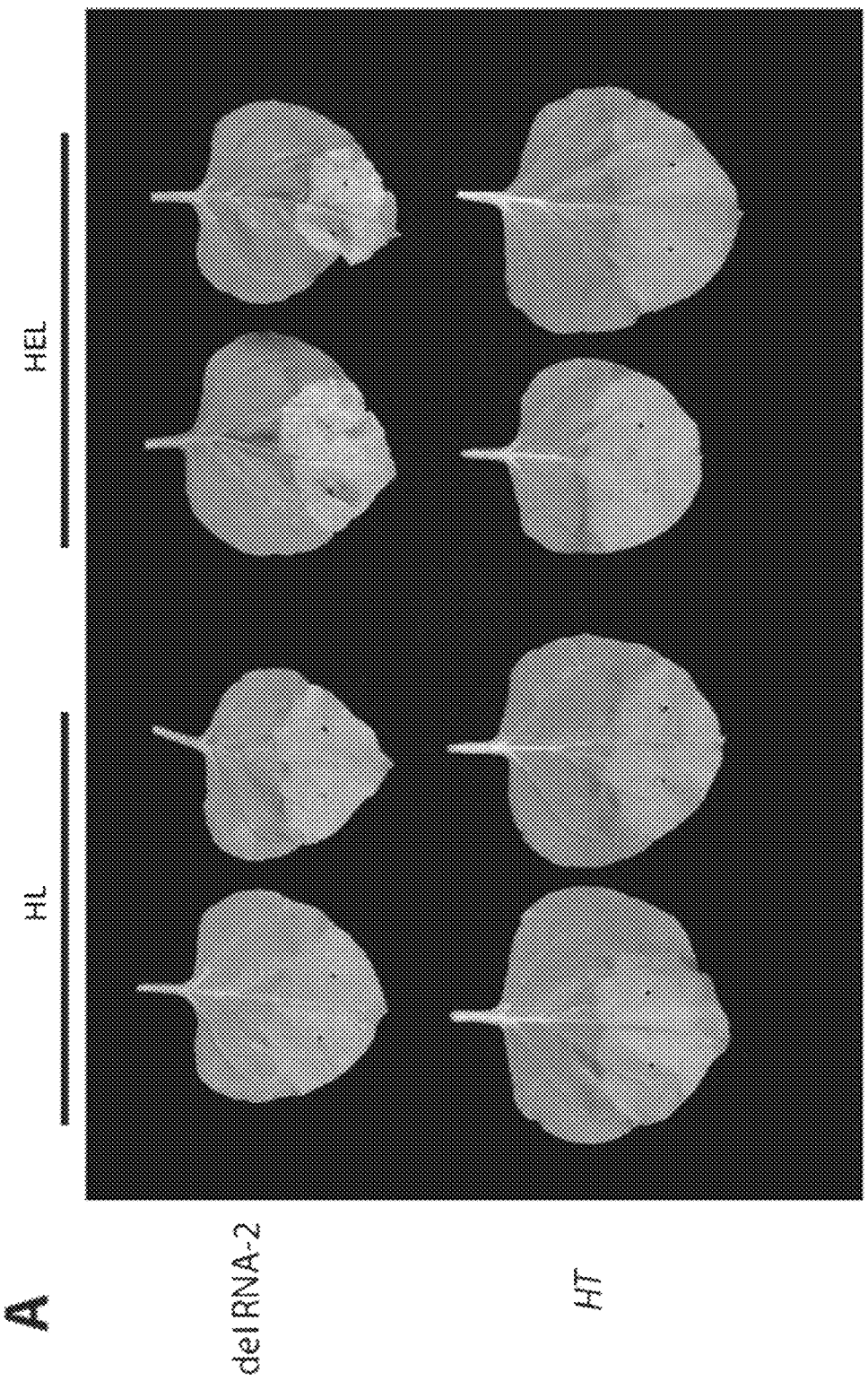

FIGURE 5 CONT'D
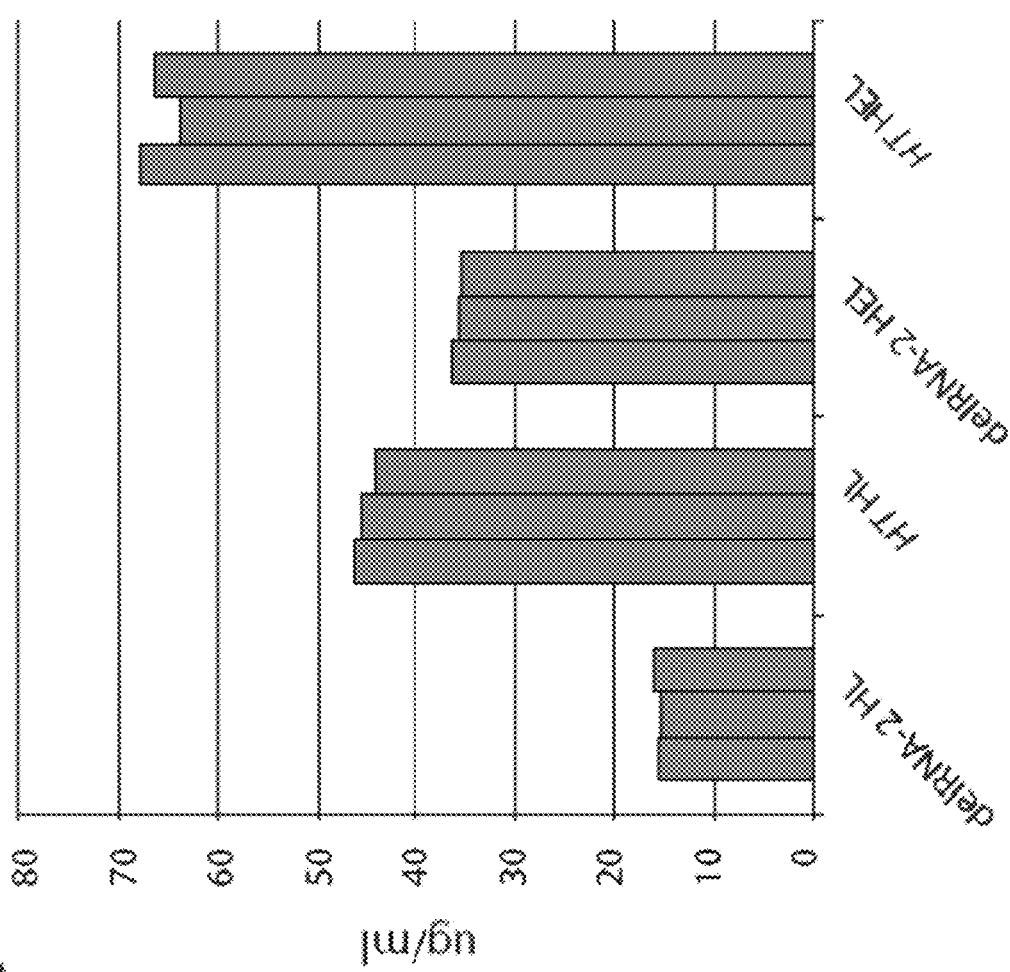
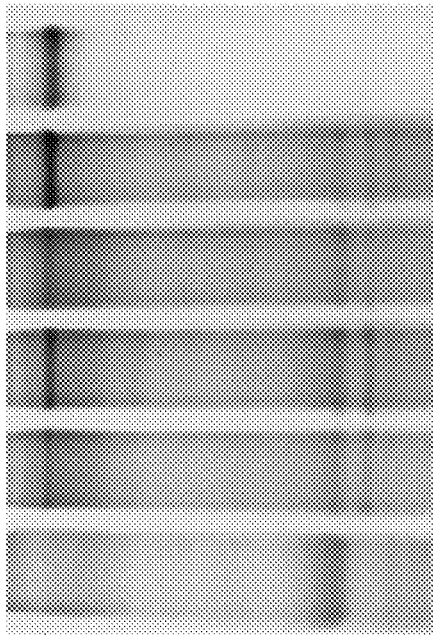

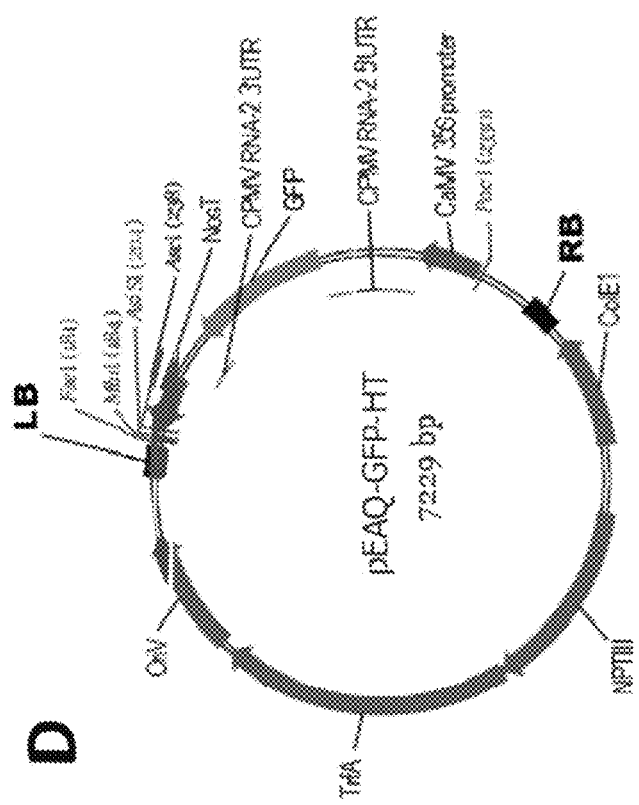
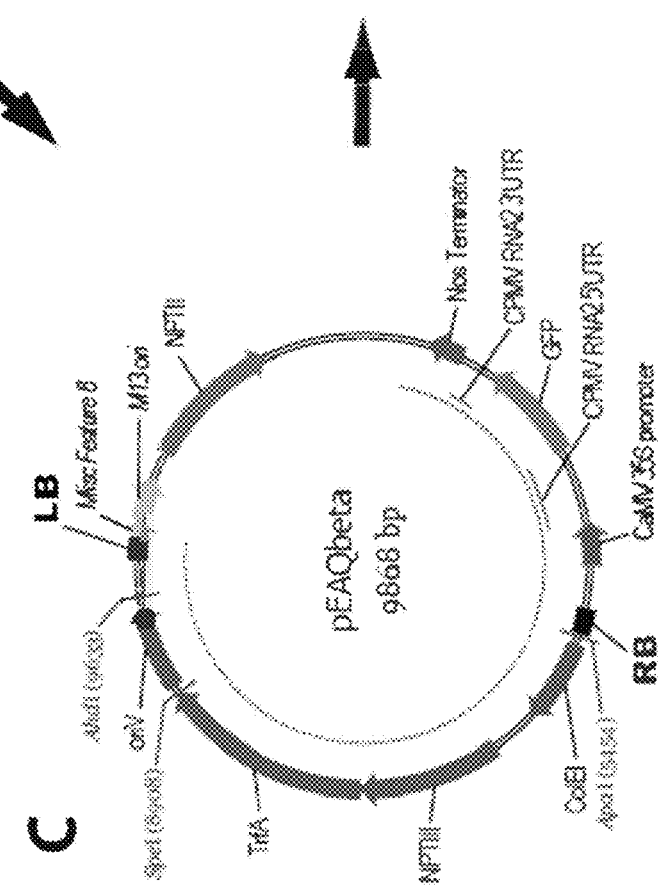
Figure 9 CONT'D

PROTEIN EXPRESSION SYSTEMS

CROSS-REFERENCE TO RELATED APPLICATIONS

This is a divisional of U.S. patent application Ser. No. 14/172,301, filed on Feb. 4, 2014, abandoned, which is a continuation of U.S. patent application Ser. No. 12/812,165, filed on Jul. 8, 2010, now U.S. Pat. No. 8,674,084, which is a U.S. national stage entry of International Patent Application No. PCT/GB2009/000060, filed on Jan. 8, 2009, which claims priority to United Kingdom Patent Application No. 0800272.7, filed on Jan. 8, 2008, the entire contents of all of which are fully incorporated herein by reference.

FIELD OF THE INVENTION

The present invention relates generally to methods and materials, and particularly viral derived sequences, for boosting gene expression in plants and other eukaryotic cells, for example of heterologous genes encoding proteins of interest.

BACKGROUND OF THE INVENTION

Comoviruses (CPMV)

Comoviruses are RNA viruses with a bipartite genome. The segments of the comoviral RNA genome are referred to as RNA-1 and RNA-2. RNA-1 encodes the VPg, replicase and protease proteins (Lomonossoff & Shanks, 1983). The replicase is required by the virus for replication of the viral genome. The RNA-2 of the comovirus cowpea mosaic virus (CPMV) encodes a 58K and a 48K protein, as well as two viral coat proteins L and S.

Initiation of translation of the RNA-2 of all comoviruses occurs at two different initiation sites located in the same triplet reading frame, resulting in the synthesis of two carboxy coterminal proteins. This double initiation phenomenon occurs as a result of 'leaky scanning' by the ribosomes during translation.

The 5' terminal start codons (AUGs) in RNA-2 of CPMV occur at positions 115, 161, 512 and 524. The start codons at positions 161 and 512 are in the same triplet reading frame. Initiation at the start codon at position 161 results in the synthesis of a 105K polyprotein while initiation at the start codon at position 512 directs the synthesis of a 95K polyprotein. As the synthesis of both polyproteins is terminated at the same stop codon at position 3299, the 105K and the 95K proteins are carboxy coterminal. The AUG codon at position 524 can serve as an initiator if the AUG at 512 is deleted. However, in the presence of the AUG 512 it does not serve this function and simply codes for the amino acid methionine (Holness et al., 1989; Wellink et al., 1993). The start codon at position 115 is not essential for virus replication (Wellink et al., 1993).

The 105K and 95K proteins encoded by CPMV RNA-2 genome segment are primary translation products which are subsequently cleaved by the RNA1-encoded proteolytic activity to yield either the 58K or the 48K protein, depending on whether it is the 105K or 95K polyprotein that is being processed, and the two viral coat proteins, L and S. Initiation of translation at the start codon at position 512 in CPMV is more efficient than initiation at position 161, resulting in the production of more 95K polyprotein than 105K polyprotein.

The start codon at position 115 in CPMV RNA-2 lies upstream of the initiation sites at positions 161 and 512 and is in a different reading frame. As this start codon is in-phase with a stop codon at position 175, initiation at this site could result in the production of a 20 amino acid peptide. However, production of such a peptide has not been detected to date.

Necessity of Maintaining the Frame Between AUGs

Mutagenesis experiments have shown that maintenance of the frame between the initiation sites at positions 161 and 512 in CPMV RNA-2 is essential for efficient replication of RNA-2 by the RNA-1-encoded replicase (Holness et al., 1989; van Bokhoven et al., 1993; Rohll et al., 1993; Wellink et al., 1993). This requirement restricts the length of sequences which can be inserted upstream of the 512 start codon in expression vectors based on CPMV RNA-2 (see below), making the cloning of foreign genes into such vectors more difficult than would be ideal. For example it precludes the use of polylinkers as their use will often alter the open reading frame (ORF) between these initiation sites.

CPMV Vectors

CPMV has served as the basis for the development of vector systems suitable for the production of heterologous polypeptides in plants (Liu et al., 2005; Sainsbury et al., 2007). These systems are based on the modification of RNA-2 but differ in whether full-length or deleted versions are used. In both cases, however, replication of the modified RNA-2 is achieved by co-inoculation with RNA-1. Expression systems based on a full-length version of RNA-2 involve the fusion of the foreign protein to the C-terminus of the RNA-2-derived polyproteins. Release of the N-terminal polypeptide is mediated by the action of the 2A catalytic peptide sequence from foot-and-mouth-disease virus (Gopinath et al., 2000). The resulting RNA-2 molecules are capable of spreading both within and between plants. This strategy has been used to express a number of recombinant proteins, such as the Hepatitis B core antigen (HBcAg) and Small Immune Proteins (SIPs), in cowpea plants (Mechtcheriakova et al., 2006; Monger et al., 2006; Alamillo et al., 2006). Though successful, the use of a full-length viral vector has disadvantages in terms of size constraints of inserted sequences and concerns about biocontainment.

To address these, a system based on a deleted version of CPMV RNA-2 has recently been developed (Cañizares et al., 2006). In this system the region of RNA-2 encoding the movement protein and both coat proteins has been removed. However, the deleted molecules still possess the cis-acting sequences necessary for replication by the RNA-1-encoded replicase and thus high levels of gene amplification are maintained without the concomitant possibility of the modified virus contaminating the environment. With the inclusion of a suppressor of gene silencing, such as HcPro from PVY, (Brigneti et al., 1998) in the inoculum in addition to RNA-1, the deleted CPMV vector can be used as a transient expression system (WO/2007/135480) Bipartite System, Method And Composition For The Constitutive And Inducible Expression Of High Levels Of Foreign Proteins In Plants; also Sainsbury et al., 2009). However, in contrast to the situation with a vector based on full-length RNA-2, replication is restricted to inoculated leaves. These CPMV vectors have been used to express multi-chain complexes consisting of a single type of polypeptide.

Multiple copies of vectors based on either full-length or deleted versions of CPMV RNA-2 have also been shown to be suitable for the production of heteromeric proteins in plants (Sainsbury et al., 2008). Co-infiltration of two full-length RNA-2 constructs containing different marker genes into *Nicotiana benthamiana* in the presence of RNA-1 has been used to show that two foreign proteins can be efficiently expressed within the same cell in inoculated tissue. Furthermore, the proteins can be co-localised to the same sub-cellular compartments, which is an essential prerequisite for heteromer formation.

The suitability of different CPMV RNA-2 vectors for the expression of heteromeric proteins in plants has also been investigated. Insertion of the heavy and light chains of an IgG into full-length and deleted versions of RNA-2 showed that both approaches led to the accumulation of full-size IgG molecules in the inoculated tissue but that the levels were significantly higher when deleted RNA-2 vectors were used. The ability of full-length RNA-2 constructs to spread systemically therefore seems to be irrelevant to the production of heteromeric proteins and the use of deleted versions of RNA-2 is clearly advantageous, especially as they also offer the benefit of biocontainment.

Thus, known CPMV based vector systems represent useful tools for the expression of a heterologous gene encoding a protein of interest in plants. However, there is still a need in the art for optimised vector systems which improve, for example, the yield of the heterologous proteins expressed and the ease of use of the vector.

SUMMARY OF INVENTION

The present inventors have surprisingly found that mutation of the start codon at position 161 in a CPMV RNA-2 vector strongly increases the levels of expression of a protein encoded by a gene inserted after the start codon at position 512. The levels of protein expression were increased about 20-30 fold compared with expression of the same protein from a CPMV RNA-2 vector differing only in that the start codon at position 161 was intact (Sainsbury and Lomonossoff, 2008). The present invention allows the production of high levels of foreign proteins without the need for viral replication.

The inventors have also found that mutation of the start codon at position 161 negates the need for maintaining the frame between the position of the mutated start codon at position 161 and the start codon at position 512, thus allowing insertion of sequences of any length after the mutated start codon at position 161. This is particularly advantageous as it allows polylinkers of any length to be inserted into RNA-2 vectors after the mutated start codon, which can then be used to facilitate cloning of a gene of interest into the vector.

In addition, the inventors have found that despite the increase in protein expression, plants transformed with a CPMV RNA-2 vector comprising a mutated start codon at position 161 looked healthier, i.e. showed less necrosis, than plants transformed with known CPMV RNA-2 vectors. Plant health is an important factor in the expression of proteins from plants as healthy plants survive for longer periods of time. In addition, plant health is also important in the purification of proteins from plants as tannins released as a result of necrosis can interfere with protein purification (Sainsbury and Lomonossoff, 2008).

Thus the present invention relates to improved protein production systems and methods, based on modified bipartite virus sequences.

Thus in various aspects of the invention there is provided or utilised an expression enhancer sequence, which sequence is derived from (or shares homology with) the RNA-2 genome segment of a bipartite RNA virus, such as a comovirus, in which a target initiation site has been mutated The present invention further provides processes for increasing the expression or translational enhancing activity of a sequence derived from an RNA-2 genome segment of a bipartite virus, which processes comprise mutating a target initiation site therein.

Some particular definitions and embodiments of the invention will now be described in more detail.

"Enhancer" sequences (or enhancer elements), as referred to herein, are sequences derived from (or sharing homology with) the RNA-2 genome segment of a bipartite RNA virus, such as a comovirus, in which a target initiation site has been mutated. Such sequences can enhance downstream expression of a heterologous ORF to which they are attached. Without limitation, it is believed that such sequences when present in transcribed RNA, can enhance translation of a heterologous ORF to which they are attached.

A "target initiation site" as referred to herein, is the initiation site (start codon) in a wild-type RNA-2 genome segment of a bipartite virus (e.g. a comovirus) from which the enhancer sequence in question is derived, which serves as the initiation site for the production (translation) of the longer of two carboxy coterminal proteins encoded by the wild-type RNA-2 genome segment.

As described above, production of the longer of the two carboxy coterminal proteins encoded by CPMV RNA-2, the 105K protein, is initiated at the initiation site at position 161 in the wild-type CPMV RNA-2 genome segment. Thus, the target initiation site in enhancer sequences derived from the CPMV RNA-2 genome segment is the initiation site at position 161 in the wild-type CPMV RNA-2.

Mutations around the start codon at position 161 may have the same (or similar) effect as mutating the start codon at position 161 itself, for example, disrupting the context around this start codon may mean that the start codon is by-passed more frequently.

In one aspect of the present invention, a target initiation site may therefore be 'mutated' indirectly by mutating one or more nucleotides upstream and/or downstream of the target initiation site, but retaining the wild-type target initiation site, wherein the effect of mutating these nucleotides is the same, or similar, to the effect observed when the target initiation site itself is mutated.

As target initiation sites serve as the initiation site for the production of the longer of two carboxy coterminal proteins encoded by a wild-type RNA-2 genome segment, it follows that target initiation sites are in-frame (in phase) with a second initiation site on the same wild-type RNA-2 genome segment, which serves as the initiation site for the production of the shorter of two carboxy coterminal proteins encoded by the wild-type RNA-2. Two initiation sites are in-frame if they are in the same triplet reading frame.

The target initiation site in enhancer sequences derived from the wild-type CPMV RNA-2 genome segment, i.e. the initiation site at position 161, is in frame with the initiation site at position 512, which serves as the initiation site for the production of the shorter of the two carboxy coterminal proteins encoded by CPMV RNA-2 (the 95K protein) in the wild-type CPMV RNA-2 genome segment.

Thus, a target initiation site is located upstream (5') of a second initiation site in the wild-type RNA-2 genome segment from which the enhancer sequence is derived, which serves the initiation site for the production of the shorter of two carboxy coterminal polyproteins encoded by the wild-type RNA-2 genome segment. In addition, a target initiation site may also be located downstream (3') of a third initiation site in the wild-type RNA-2 genome from which the enhancer sequence is derived. In CPMV the target initiation site, i.e. the initiation site at position 161, is located upstream of a second initiation site at position 512 which serves as the initiation site for the production of the 95K protein and downstream of a third initiation site at position 115.

A target initiation site in an enhancer sequence derived from the RNA-2 genome segment of a bipartite virus is therefore the first of two initiation sites for the production of two carboxy coterminal proteins encoded by the wild-type RNA-2. 'First' in this context refers to the initiation site located closer to the 5' end of the wild-type RNA-2 genome segment.

More than one initiation site in the sequence may be mutated, if desired. For example the 'third' initiation site at (or corresponding to) position 115 may also be deleted or altered. It has been shown that removal of AUG 115 in addition to the removal of AUG 161, further enhances expression (Sainsbury and Lomonossoff, 2008).

The enhancer sequences of the present invention are based on modified sequences from the RNA-2 genome segments of bipartite RNA viruses.

A bipartite virus, or virus with a bipartite genome, as referred to herein may be a member of the Comoviridae family. All genera of the family Comoviridae appear to encode two carboxy-coterminal proteins. The genera of the Comoviridae family include Comovirus, Nepovirus, Fabavirus, Cheravirus and Sadwavirus. Comoviruses include Cowpea mosaic virus (CPMV), Cowpea severe mosaic virus (CPSMV), Squash mosaic virus (SqMV), Red clover mottle virus (RCMV), Bean pod mottle virus (BPMV). Preferably, the bipartite virus (or comovirus) is CPMV.

The sequences of the RNA-2 genome segments of these comoviruses and several specific strains are available from the NCBI database under the accession numbers listed in brackets: cowpea mosaic virus RNA-2 (NC_003550), cowpea severe mosaic virus RNA-2 (NC_003544), squash mosaic virus RNA-2 (NC_003800), squash mosaic virus strain Kimble RNA-2 (AF059533), squash mosaic virus strain Arizona RNA-2 (AF059532), red clover mottle virus RNA-2 (NC_003738), bean pod mottle virus RNA-2 (NC_003495), bean pod mottle virus strain K-Hopkins1 RNA-2 (AF394609), bean pod mottle virus strain K-Hancock1 RNA-2 (AF394607), Andean potato mottle virus (APMoV: L16239) and Radish mosaic virus (RaMV; AB295644). There are also partial RNA-2 sequences available from bean rugose mosaic virus (BRMV; AF263548) and a tentative member of the genus Comovirus, turnip ringspot virus (EF191015). Numerous sequences from the other genera in the family Comoviridae are also available.

To date, all comoviruses which have been investigated have been shown to have two alternative start codons for the expression of two carboxy coterminal polyproteins form their RNA-2 genome segments. In particular, the RNA-2 genome segments of CPMV, CPSMV, BPMV, SqMV and RCMV are known to comprise two alternative start codons for the expression of two carboxy coterminal polyproteins.

Target initiation sites in other comoviruses, which are equivalent to the initiation site at position 161 in the wild-type RNA-2 segment of CPMV (i.e. correspond to it) can therefore be identified by methods known in the art. For example, target initiation sites can be identified by a sequence alignment between the wild-type RNA-2 genome segment sequence of CPMV and the RNA-2 genome segment sequence of another comovirus. Such sequence alignments can then be used to identify a target initiation site in the comoviral RNA-2 genome segment sequence by identifying an initiation site which, at least in the alignment, is near, or at the same position as, the target initiation site at position 161 in the wild-type CPMV RNA-2.

Target initiation sites in other comoviruses may also be identified by determining the start codon which serves as the initiation site for the synthesis of the longer of two carboxy coterminal proteins encoded by the wild-type comoviral RNA-2 genome segment. This approach can also be used in combination with an alignment as described above, i.e. this approach can be used to confirm that a comoviral initiation site identified by means of an alignment with CPMV RNA-2 is a target initiation site.

Of course, the above methods can also be used for identifying initiation sites in other comoviral RNA-2 genome segments, which are equivalent to the initiation site at position 512 in the wild-type CPMV RNA-2 genome segment. However, instead of identifying the start codon which serves as the initiation site for the synthesis of the longer of two carboxy coterminal proteins encoded by the wild-type comoviral RNA-2 genome segment, the start codon which serves as the initiation site for the synthesis of the shorter of two carboxy coterminal proteins encoded by the wild-type comoviral RNA-2 genome segment, is identified.

Once two comoviral RNA-2 initiation sites which are likely to be equivalent to the initiation sites at positions 161 and 512 in CPMV RNA-2 have been identified, the identification of the target initiation site can be confirmed by checking that the two initiation sites are in the same frame, i.e. in the same triplet reading frame, as they can only serve as initiation sites for the production of two carboxy coterminal proteins if this is the case.

In one embodiment of the invention, the enhancer sequence comprises nucleotides 1 to 512 of the CPMV RNA-2 genome segment (see Table 2), wherein the target initiation site at position 161 has been mutated. In another embodiment of the invention, the enhancer sequence comprises an equivalent sequence from another comovirus, wherein the target initiation site equivalent to the start codon at position 161 of CPMV has been mutated. The target initiation site may be mutated by substitution, deletion or insertion. Preferably, the target initiation site is mutated by a point mutation.

In alternative embodiments of the invention, the enhancer sequence comprises nucleotides 10 to 512, 20 to 512, 30 to 512, 40 to 512, 50 to 512, 100 to 512, 150 to 512, 1 to 514, 10 to 514, 20 to 514, 30 to 514, 40 to 514, 50 to 514, 100 to 514, 150 to 514, 1 to 511, 10 to 511, 20 to 511, 30 to 511, 40 to 511, 50 to 511, 100 to 511, 150 to 511, 1 to 509, 10 to 509, 20 to 509, 30 to 509, 40 to 509, 50 to 509, 100 to 509, 150 to 509, 1 to 507, 10 to 507, 20 to 507, 30 to 507, 40 to 507, 50 to 507, 100 to 507, or 150 to 507 of a comoviral RNA-2 genome segment sequence with a mutated target initiation site. In other embodiments of the invention, the enhancer sequence comprises nucleotides 10 to 512, 20 to 512, 30 to 512, 40 to 512, 50 to 512, 100 to 512, 150 to 512, 1 to 514, 10 to 514, 20 to 514, 30 to 514, 40 to 514, 50 to 514, 100 to 514, 150 to 514, 1 to 511, 10 to 511, 20 to 511, 30 to 511, 40 to 511, 50 to 511, 100 to 511, 150 to 511, 1 to 509, 10 to 509, 20 to 509, 30 to 509, 40 to 509, 50 to 509, 100 to 509, 150 to 509, 1 to 507, 10 to 507, 20 to 507, 30 to 507, 40 to 507, 50 to 507, 100 to 507, or 150 to 507 of the CPMV RNA-2 genome segment sequence shown in Table 2, wherein the target initiation site at position 161 in the wild-type CPMV RNA-2 genome segment has been mutated.

In further embodiments of the invention, the enhancer sequence comprises nucleotides 1 to 500, 1 to 490, 1 to 480, 1 to 470, 1 to 460, 1 to 450, 1 to 400, 1 to 350, 1 to 300, 1 to 250, 1 to 200, or 1 to 100 of a comoviral RNA-2 genome segment sequence with a mutated target initiation site.

In alternative embodiments of the invention, the enhancer sequence comprises nucleotides 1 to 500, 1 to 490, 1 to 480, 1 to 470, 1 to 460, 1 to 450, 1 to 400, 1 to 350, 1 to 300, 1 to 250, 1 to 200, or 1 to 100 of the CPMV RNA-2 genome segment sequence shown in Table 2, wherein the target initiation site at position 161 in the wild-type CPMV RNA-2 genome segment has been mutated.

Enhancer sequences comprising at least 100 or 200, at least 300, at least 350, at least 400, at least 450, at least 460, at least 470, at least 480, at least 490 or at least 500 nucleotides of a comoviral RNA-2 genome segment sequence with a mutated target initiation site are also embodiments of the invention.

In addition, enhancer sequences comprising at least 100 or 200, at least 300, at least 350, at least 400, at least 450, at least 460, at least 470, at least 480, at least 490 or at least 500 nucleotides of the CPMV RNA-2 genome segment sequence shown in Table 2, wherein the target initiation site at position 161 in the wild-type CPMV RNA-2 genome segment has been mutated, are also embodiments of the invention.

Alternative embodiments of the invention are enhancer sequences having at least 99%, 98%, 97%, 96%, 95%, 90%, 85%, 80%, 75%, 70%, 65%, 60%, 55%, or 50% identity to the CPMV RNA-2 genome segment sequence shown in Table 2, wherein the target initiation site at position 161 in the wild-type CPMV RNA-2 genome segment has been mutated.

The terms "percent similarity", "percent identity" and "percent homology" when referring to a particular Sequence are used as set forth in the University of Wisconsin GCG software program. Enhancer sequences may thus specifically hybridise with the complementary sequence of the CPMV RNA-2 genome segment sequence shown in Table 2, with the proviso that the target initiation site corresponding to position 161 in the wild-type CPMV RNA-2 genome segment has been mutated.

The phrase "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. "Complementary" refers to the natural association of nucleic acid sequences by base-pairing (A-G-T pairs with the complementary sequence T-C-A). Complementarity between two single-stranded molecules may be partial, if only some of the nucleic acids pair are complementary; or complete, if all bases pair are complementary. The degree of complementarity affects the efficiency and strength of hybridization and amplification reactions.

A target initiation site in an enhancer sequence of the invention may be mutated by deletion, insertion or substitution, such that it no longer functions as a translation initiation site. For example, a point mutation may be made at the position of the target initiation site in the enhancer sequence. Alternatively, the target initiation site in the enhancer sequence may be deleted either partially or in its entirety. For example, a deletion spanning the target initiation site in the enhancer sequence may be made. Deletions spanning the initiation site may be up to 5, up to 10, up to 15, up to 20, up to 25, up to 30, up to 35, up to 40, up to 45, or up to 50 nucleotides in length, when compared with the sequence of the wild-type RNA-2 genome segment from which the enhancer sequence is derived.

Without wishing to be bound by theory, mutation of the start codon at position 161 in CPMV is thought to lead to the inactivation of a translational suppressor, which results in enhanced initiation of translation from start codons located downstream of the inactivated translational suppressor.

Thus, the present invention further provides an enhancer sequence derived from an RNA-2 genome segment of a bipartite virus, wherein the enhancer sequence comprises an inactivated translational suppressor sequence.

The present invention further provides a process for increasing the expression or translational enhancing activity of a sequence derived from an RNA-2 genome segment of a bipartite virus, which process comprises inactivating a translational suppressor sequence therein.

As already mentioned above, mutation of the initiation site at position 161 in the CPMV RNA-2 genome segment is thought to lead to the inactivation of a translation suppressor normally present in the CPMV RNA-2.

A translational suppressor sequence, as referred to herein, is a sequence in the wild-type RNA-2 genome segment of the bipartite virus (e.g. a comovirus) from which the enhancer sequence in question is derived, which comprises, or consists of, the initiation site for the production (translation) of the longer of two carboxy coterminal proteins encoded by the wild-type RNA-2 genome segment.

Translational suppressor sequences in enhancer sequences derived from the CPMV RNA-2 genome segment, are sequences comprising, or consisting of, the target initiation site described above. Thus, translational suppressor sequences comprise, or consist of, a target initiation site as defined above, and may be inactivated by mutagenesis as described above.

The enhancer sequences defined above may be used in various aspects and embodiments of the invention as follows.

Thus in one aspect of the present invention there is provided or utilised an isolated nucleic acid consisting, or consisting essentially of, an expression enhancer sequence as described above.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" Is sometimes used. This term, when applied to DNA, refers to a DNA molecule that is separated from sequences with which it is immediately contiguous in the naturally occurring genome of the organism in which it originated.

For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

The nucleic acid may thus consist or consist essentially of a portion, or fragment, of the RNA-2 genome segment of the bipartite RNA virus from which the enhancer is derived. For example, in one embodiment the nucleic acid does not comprise at least a portion of the coding region of the RNA-2 genome segment from which it is derived. The coding region may be the region of the RNA-2 genome segment encoding the shorter of two carboxy coterminal proteins. The nucleic acid may consist or consist essentially of the portion of an RNA-2 genome segment of a bipartite virus extending from the 5' end of the wild-type RNA-2 genome segment to the initiation site from which production (translation) of the shorter of two carboxy coterminal proteins encoded by the wild-type RNA-2 genome segment is initiated.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence. For example, when used in reference to a nucleic acid, the phrase includes the sequence per se and minor changes and\or extensions that would not affect the enhancer function of the sequence, or provide further (additional) functionality.

The invention further relates to gene expression systems comprising an enhancer sequence of the invention.

Thus, in another aspect the present invention provides a gene expression system comprising an enhancer sequence as described above.

The gene expression system may also comprise a gene encoding a protein of interest inserted downstream of the enhancer sequence. Inserted sequences encoding a protein of interest may be of any size.

In a further aspect the present invention therefore provides a gene expression system comprising:
(a) an enhancer sequence as described above; and (b) a gene encoding a protein of interest, wherein the gene is located downstream of the enhancer sequence.

The gene and protein of interest may be a heterologous i.e. not encoded by the wild-type bipartite RNA virus from which the enhancer sequence is derived.

Gene expression systems may be used to express a protein of interest in a host organism. In this case, the protein of interest may also be heterologous to the host organism in question i.e. introduced into the cells in question (e.g. of a plant or an ancestor thereof) using genetic engineering, i.e. by human intervention. A heterologous gene in an organism may replace an endogenous equivalent gene, i.e. one which normally performs the same or a similar function, or the inserted sequence may be additional to the endogenous gene or other sequence.

Persons skilled in the art will understand that expression of a gene of interest will require the presence of an initiation site (AUG) located upstream of the gene to be expressed. Such initiation sites may be provided either as part of an enhancer sequence or as part of a gene encoding a protein of interest.

The host organism may be a plant. However, as translational mechanisms are well conserved over eukaryotes, the gene expression systems may also be used to express a protein of interest in eukaryotic host organisms other than plants, for example in insect cells as modified baculovirus vectors, or in yeast or mammalian cells.

Gene expression systems may be operably linked to promoter and terminator sequences.

Thus, gene expression systems may further comprise a termination sequence and the gene encoding a protein of interest may be located between the enhancer sequence and the termination sequence, i.e. downstream (3') of the enhancer sequence and upstream (5') of the termination sequence.

Thus the invention further provides an expression cassette comprising:
(i) a promoter, operably linked to
(ii) an enhancer sequence as described above
(iii) a gene of interest it is desired to express
(iv) a terminator sequence.

Preferably the promoter used to drive the gene of interest will be a strong promoter. Examples of strong promoters for use in plants include:
(1) p35S: Odell et al., 1985
(2) Cassava Vein Mosaic Virus promoter, pCAS, Verdaguer et al., 1996
(3) Promoter of the small subunit of ribulose biphosphate carboxylase, pRbcS: Outchkourov et al., 2003.

Other strong promoters include pUbi (for monocots and dicots) and pActin.

In a preferred embodiment, the promoter is an inducible promoter.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus.

The termination (terminator) sequence may be a termination sequence derived from the RNA-2 genome segment of a bipartite RNA virus, e.g. a comovirus. In one embodiment the termination sequence may be derived from the same bipartite RNA virus from which the enhancer sequence is derived. The termination sequence may comprise a stop codon. Termination sequence may also be followed by polyadenylation signals.

Gene expression cassettes, gene expression constructs and gene expression systems of the invention may also comprise an untranslated region (UTR). The UTR may be located upstream of a terminator sequence present in the gene expression cassette, gene expression construct or gene expression system. Where the gene expression cassettes, gene expression constructs or gene expression systems comprises a gene encoding a protein of interest, the UTR may be located downstream of said gene. Thus, the UTR may be located between a gene encoding a protein of interest and a terminator sequence. The UTR may be derived from a bipartite RNA virus, e.g. from the RNA-2 genome segment of a bipartite RNA virus. The UTR may be the 3' UTR of the same RNA-2 genome segment from which the enhancer sequence present in the gene expression cassette, gene expression construct or gene expression system is derived.

Preferably, the UTR is the 3' UTR of a comoviral RNA-2 genome segment, e.g. the 3' UTR of the CPMV RNA-2 genome segment.

As described above, it was previously shown to be essential for efficient replication of CPMV RNA-2 by the CPMV RNA-1-encoded replicase that the frame between the initiation sites at positions 161 and 512 in the RNA-2 was maintained, i.e. that the two initiation sites remained in the same triple reading frame (Holness et al., 1989; van Bokhoven et al., 1993; Rohll et al., 1993). This requirement limited the length of sequences which could be inserted upstream of the initiation site at position 512 in expression vectors based on CPMV. In particular, it precluded the use of polylinkers as their use often altered the open reading frame (ORF) between the two initiation sites.

The present inventors have shown that maintenance of the reading frame between the initiation sites at positions 161 and 512 in CPMV RNA-2 is also required for efficient initiation of translation at the initiation site at position 512, i.e. it is required for efficient expression of the shorter of the two carboxy coterminal proteins encoded by CPMV (the 95K protein).

However, the present inventors have also demonstrated that mutation of the initiation site at position 161 in CPMV RNA-2 allows insertion of sequences upstream of the initiation site at position 512, which alter the frame between the mutated start codon and the initiation site at position 512, without any negative effect on the level of expression of the 95K protein. Consequently, mutation of the initiation site at position 161 means that there is no longer any restriction on the length of sequences that can be inserted upstream of the initiation site at position 512.

Where maintenance of the reading frame between initiation sites coding for two carboxy-coterminal proteins is also required in other bipartite viruses, this requirement may also be overcome by mutating the AUG which serves as the initiation site for productions of the longer of the two carboxy-coterminal proteins encoded by the viral RNA-2 genome segment. Thus, in another aspect the present invention provides a gene expression construct comprising:
(a) an enhancer sequence as described above; and
(b) a heterologous sequence for facilitating insertion of a gene encoding a protein of interest into the gene expression system, wherein the heterologous sequence is located downstream of the mutated target initiation site in the enhancer sequence.

The heterologous sequence may be located upstream of the start codon from which production of the shorter of two carboxy coterminal proteins is initiated in the wild-type RNA-2 genome segment from which the enhancer sequence of the gene expression system is derived. Alternatively, the heterologous sequence may be provided around the site of the start codon, or replace the start codon, from which production of the shorter of two carboxy coterminal proteins is initiated in the wild-type RNA-2 genome segment from which the enhancer sequence of the gene expression system is derived. In a gene expression system with an enhancer sequence derived from the RNA-2 of CPMV, the heterologous sequence may be provided upstream of, around the site of, or replace, the start codon which is at position 512 in the wild-type RNA-2 CPMV genome segment.

The heterologous sequence may be a polylinker or multiple cloning site, i.e. a sequence which facilitates cloning of a gene encoding a protein of interest into the expression system.

For example, as described hereinafter, the present inventors have provided constructs including a polylinker between the 5' leader and 3' UTRs of a CPMV-based expression cassette. As described below, any polyinker may optionally encode one or more sets of multiple x Histidine residues to allow the fusion of N- or C terminal His-tags to facilitate protein purification.

Preferably the expression constructs above are present in a vector, and preferably it comprises border sequences which permit the transfer and integration of the expression cassette into the organism genome.

Preferably the construct is a plant binary vector. Preferably the binary transformation vector is based on pPZP (Hajdukiewicz, et al. 1994). Other example constructs include pBin 19 (see Frisch, D. A., L. W. Harris-Haller, et al. (1995). "Complete Sequence of the binary vector Bin 19." Plant Molecular Biology 27: 405-409).

As described herein, the invention may be practiced by moving an expression cassette with the requisite components into an existing pBin expression cassette, or in other embodiments a direct-cloning pBin expression vector may be utilised.

For example, as described hereinafter, the present inventors have modular binary vectors designed for (but not restricted to) use with the enhancer sequences described herein. These are based on improvements to the pBINPLUS vector whereby it has been shown that it is possible to drastically reduce the size of the vector without compromising performance in terms of replication and TDNA transfer. Furthermore, elements of the enhancer system (as exemplified by the so-called "CPMV-HT" system) have been incorporated into the resulting vector in a modular fashion such that multiple proteins can be expressed from a single T-DNA. These improvements have led to the creation of a versatile, high-level expression vector that allows efficient direct cloning of foreign genes.

These examples represent preferred binary plant vectors. Preferably they include the ColE1 origin of replication, although plasmids containing other replication origins that also yield high copy numbers (such as pRi-based plasmids, Lee and Gelvin, 2008) may also be preferred, especially for transient expression systems.

If desired, selectable genetic markers may be included in the construct, such as those that confer selectable phenotypes such as resistance to antibiotics or herbicides (e.g. kanamycin, hygromycin, phosphinotricin, chlorsulfuron, methotrexate, gentamycin, spectinomycin, imidazolinones and glyphosate).

Most preferred vectors are the pEAQ vectors described below which permit direct cloning version by use of a polylinker between the 5' leader and 3' UTRs of an expression cassette including a translational enhancer of the invention, positioned on a T-DNA which also contains a suppressor of gene silencing and an NPTII cassettes. The polylinker also encodes one or two sets of 6× Histidine residues to allow the fusion of N- or C terminal His-tags to facilitate protein purification.

An advantage of pEAQ-derived vectors is that each component of a multi-chain protein such as an IgG can automatically be delivered to each infected cell.

The present invention also provides methods of expressing proteins, e.g. heterologous proteins, in host organisms such as plants, yeast, insect or mamalian cells, using a gene expression system of the invention.

The present invention further provides a method of enhancing the translation of a heterologous protein of interest from a gene or ORF encoding the same which is operably linked to an RNA2-derived sequence as described above, the method comprising mutating a target initiation site in the RNA2-derived sequence.

The enhancer sequences described herein may also be used with bipartite expression systems as described in WO/2007/135480. The invention therefore also relates to gene expression systems based on truncated RNA-2 gene segments, optionally further comprising a second gene construct encoding a suppressor of gene silencing operably linked to promoter and terminator sequences.

In a further aspect the present invention therefore relates to a gene expression system comprising:
(a) a first gene construct comprising a truncated RNA-2 of a bipartite virus genome carrying at least one foreign gene encoding a heterologous protein of interest operably linked to promoter and terminator sequences, wherein the gene construct comprises a mutated target initiation site upstream of the foreign gene; and optionally
(b) a second gene construct comprising RNA-1 of said bipartite virus genome operably linked to promoter and terminator sequences; and optionally
(c) a third gene construct, optionally incorporated within said first gene construct, said second gene construct or both, comprising a suppressor of gene silencing operably linked to promoter and terminator sequences.

The presence of a suppressor of gene silencing in a gene expression system (including any of those described above) of the invention is preferred but not essential. Thus, a gene expression system, as defined above, preferably comprises a third gene construct, optionally incorporated within said first gene construct, said second gene construct or both, comprising a suppressor of gene silencing operably linked to promoter and terminator sequences.

Thus, in another aspect the present invention provides a method of expressing a protein in a plant comprising the steps of:
(a) introducing a gene expression construct of the invention into a plant cell; and optionally
(b) introducing a second gene construct comprising RNA-1 of said bipartite virus genome operably linked to promoter and terminator sequences into the plant cell; and optionally
(c) introducing a third gene construct, optionally incorporated within said first gene construct, said second gene construct or both, comprising a suppressor of gene silencing operably linked to promoter and terminator sequences into the plant cell.

Preferably, a method of expressing a protein in a plant, as defined above, comprises the step of introducing a third gene construct, optionally incorporated within said first gene construct, said second gene construct or both, comprising a suppressor of gene silencing operably linked to promoter and terminator sequences into the plant cell.

The present invention also provides methods comprising introduction of such a construct into a plant cell.

The present inventors have shown very high expression levels by incorporating both a gene of interest and a suppressor of silencing onto the same T-DNA as the translational enhancer. Preferred embodiments may therefore utilise all these components are present on the same T-DNA.

Additionally it should be understood that the RNA-1 is not required for high level expression in the systems described herein, and indeed the "CPMV-HT" system described herein is not by the action of RNA-1.

Thus in a further aspect the present invention therefore relates to a gene expression system comprising:
(a) a first gene construct comprising a truncated RNA-2 of a bipartite virus genome carrying at least one foreign gene encoding a heterologous protein of interest operably linked to promoter and terminator sequences, wherein the gene construct comprises a mutated target initiation site upstream of the foreign gene; and optionally
(b) a second gene construct optionally incorporated within said first gene construct, a suppressor of gene silencing operably linked to promoter and terminator sequences.

Thus, in another aspect the present invention provides a method of expressing a protein in a plant comprising the steps of:
(a) introducing a gene expression construct of the invention into a plant cell; and optionally
(b) introducing a second gene construct optionally incorporated within said first gene construct, comprising a suppressor of gene silencing operably linked to promoter and terminator sequences into the plant cell.

Suppressors of gene silencing useful in these aspects are known in the art and described in WO/2007/135480. They include HcPro from Potato virus Y, He-Pro from TEV, P19 from TBSV, rgsCam, B2 protein from FHV, the small coat protein of CPMV, and coat protein from TCV. Most preferably, the RNA-2 of the system is truncated such that no infectious virus is produced.

A preferred suppressor when producing stable transgenic plants is the P19 suppressor incorporating a R43W mutation.

In a further aspect of the invention, there is disclosed a host cell containing a heterologous construct according to the present invention.

Gene expression vectors of the invention may be transiently or stably incorporated into plant cells.

For small scale production, mechanical agroinfiltration of leaves with constructs of the invention. Scale-up is achieved through, for example, the use of vacuum infiltration.

In other embodiments, an expression vector of the invention may be stably incorporated into the genome of the transgenic plant or plant cell.

In one aspect the invention may further comprise the step of regenerating a plant from a transformed plant cell.

Specific procedures and vectors previously used with wide success upon plants are described by Guerineau and Mullineaux (1993) (Plant transformation and expression vectors. In: Plant Molecular Biology Labfax (Croy RRD ed) Oxford, BIOS Scientific Publishers, pp 121-148). Suitable vectors may include plant viral-derived vectors (see e.g. EP-A-194809). If desired, selectable genetic markers may be included in the construct, such as those that confer selectable phenotypes such as resistance to antibiotics or herbicides (e.g. kanamycin, hygromycin, phosphinotricin, chlorsulfuron, methotrexate, gentamycin, spectinomycin, imidazolinones and glyphosate).

Nucleic acid can be introduced into plant cells using any suitable technology, such as a disarmed Ti-plasmid vector carried by *Agrobacterium* exploiting its natural gene transfer ability (EP-A-270355, EP-A-0116718, NAR 12(22) 8711-87215 1984; the floral dip method of Clough and Bent, 1998), particle or microprojectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614 Gelvin Debeyser) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, PNAS U.S.A. 87: 1228 (1990d) Physical methods for the transformation of plant cells are reviewed in Oard, 1991, *Biotech.*

*Adv.* 9: 1-11. Ti-plasmids, particularly binary vectors, are discussed in more detail below.

*Agrobacterium* transformation is widely used by those skilled in the art to transform dicotyledonous species. However there has also been considerable success in the routine production of stable, fertile transgenic plants in almost all economically relevant monocot plants (see e.g. Hiei et al. (1994) *The Plant Journal* 6, 271-282)). Microprojectile bombardment, electroporation and direct DNA uptake are preferred where *Agrobacterium* alone is inefficient or ineffective. Alternatively, a combination of different techniques may be employed to enhance the efficiency of the transformation process, eg bombardment with *Agrobacterium* coated microparticles (EP-A-486234) or microprojectile bombardment to induce wounding followed by co-cultivation with *Agrobacterium* (EP-A-486233).

The particular choice of a transformation technology will be determined by its efficiency to transform certain plant species as well as the experience and preference of the person practising the invention with a particular methodology of choice.

It will be apparent to the skilled person that the particular choice of a transformation system to introduce nucleic acid into plant cells is not essential to or a limitation of the invention, nor is the choice of technique for plant regeneration. In experiments performed by the inventors, the enhanced expression effect is seen in a variety of integration patterns of the T-DNA.

Thus various aspects of the present invention provide a method of transforming a plant cell involving introduction of a construct of the invention into a plant tissue (e.g. a plant cell) and causing or allowing recombination between the vector and the plant cell genome to introduce a nucleic acid according to the present invention into the genome. This may be done so as to effect transient expression.

Alternatively, following transformation of plant tissue, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol I, II and III, Laboratory Procedures and Their Applications*, Academic Press, 1984, and Weissbach and Weissbach, *Methods for Plant Molecular Biology*, Academic Press, 1989.

The generation of fertile transgenic plants has been achieved in the cereals such as rice, maize, wheat, oat, and barley plus many other plant species (reviewed in Shimamoto, K. (1994) *Current Opinion in Biotechnology* 5, 158-162; Vasil, et al. (1992) *Bio/Technology* 10, 667-674; Vain et al., 1995, *Biotechnology Advances* 13 (4): 653-671; Vasil, 1996, *Nature Biotechnology* 14 page 702).

Regenerated plants or parts thereof may be used to provide clones, seed, selfed or hybrid progeny and descendants (e.g. F1 and F2 descendants), cuttings (e.g. edible parts), propagules, etc.

The invention further provides a transgenic organism (for example obtained or obtainable by a method described herein) in which an expression vector or cassette has been introduced, and wherein the heterologous gene in the cassette is expressed at an enhanced level, The invention further comprises a method for generating the protein of interest, which method comprises the steps of performing a method (or using an organism) as described above, and optionally harvesting, at least, a tissue in which the protein of interest has been expressed and isolating the protein of interest from the tissue.

Specifically, the present invention therefore provides a transgenic plant or plant cell transiently transfected with an expression vector of the invention.

In a further aspect, the present invention also provides a transgenic plant or plant cell stably transformed with an expression vector of the invention.

The invention also provides a plant propagule from such plants, that is any part which may be used in reproduction or propagation, sexual or asexual, including cuttings, seed and so on. It also provides any part of these plants which includes the plant cells or heterologous DNA described above.

Thus in various aspects (and without limitation) the invention provides:

Nucleic acids consisting or consisting essentially of an enhancer sequence of the invention (which enhancer sequence may (for example) consist of nucleotides 1 to 512 of the CPMV RNA-2 genome segment, or be derived from that, or from another RNA-2 genome segment of a bipartite RNA virus, in each case in which the target initiation site corresponding to CPMV RNA-2 position 161 is mutated).

Gene expression systems comprising such enhancer sequences, for example upstream of an ORF encoding a protein of interest, or a polylinker, and optionally terminator.

Bipartite expression systems as described in WO/2007/135480 modified according to the present invention to use enhancer sequences described herein.

Expression cassettes comprising: (i) a promoter, operably linked to (ii) an enhancer sequence as described above (iii) a polylinker or gene of interest it is desired to express (iv) the cognate 3' UTR (i.e. from the 3' UTR of the CPMV RNA-2 genome segment), (v) a terminator sequence.

Methods of expressing proteins, e.g. heterologous proteins, in host organisms such as plants using gene expression systems or vectors of the invention.

Host cells and organisms (e.g. plants or yeasts) expressing proteins from the gene expression systems or vectors of the invention and methods of producing the same.

"Gene" unless context demands otherwise refers to any nucleic acid encoding genetic information for translation into a peptide, polypeptide or protein. Thus unless context demands otherwise it used interchangeably with "ORF".

The genes which it may be desired to express may be transgenes or endogenes.

Genes of interest include those encoding agronomic traits, insect resistance, disease resistance, herbicide resistance, sterility, grain characteristics, and the like. The genes may be involved in metabolism of oil, starch, carbohydrates, nutrients, etc. Thus genes or traits of interest include, but are not limited to, environmental- or stress-related traits, disease-related traits, and traits affecting agronomic performance. Target sequences also include genes responsible for the synthesis of proteins, peptides, fatty acids, lipids, waxes, oils, starches, sugars, carbohydrates, flavors, odors, toxins, carotenoids, hormones, polymers, flavonoids, storage proteins, phenolic acids, alkaloids, lignins, tannins, celluloses, glycoproteins, glycolipids, etc.

Most preferably the targeted genes in monocots and/or dicots may include those encoding enzymes responsible for oil production in plants such as rape, sunflower, soya bean and maize; enzymes involved in starch synthesis in plants such as potato, maize, cereals; enzymes which synthesise, or proteins which are themselves, natural medicaments such as pharmaceuticals or veterinary products.

Heterologous nucleic acids may encode, inter alia, genes of bacterial, fungal, plant or animal origin. The polypeptides may be utilised in planta (to modify the characteristics of the plant e.g. with respect to pest susceptibility, vigour, tissue differentiation, fertility, nutritional value etc.) or the plant may be an intermediate for producing the polypeptides which can be purified therefrom for use elsewhere. Such proteins include, but are not limited to retinoblastoma protein, p53, angiostatin, and leptin. Likewise, the methods of the invention can be used to produce mammalian regulatory proteins. Other sequences of interest include proteins, hormones, growth factors, cytokines, serum albumin, haemoglobin, collagen, etc.

Thus the target gene or nucleotide sequence preferably encodes a protein of interest which is: an insect resistance protein; a disease resistance protein; a herbicide resistance protein; a mammalian protein.

"Vector" is defined to include, inter alia, any plasmid, cosmid, phage, viral or *Agrobacterium* binary vector in double or single stranded linear or circular form which may or may not be self transmissible or mobilizable, and which can transform a prokaryotic or eukaryotic host either by integration into the cellular genome or exist extrachromosomally (e.g. autonomous replicating plasmid with an origin of replication). The constructs used will be wholly or partially synthetic. In particular they are recombinant in that nucleic acid sequences which are not found together in nature (do not run contiguously) have been ligated or otherwise combined artificially. Unless specified otherwise a vector according to the present invention need not include a promoter or other regulatory sequence, particularly if the vector is to be used to introduce the nucleic acid into cells for recombination into the genome.

"Binary Vector": as is well known to those skilled in the art, a binary vector system includes (a) border sequences which permit the transfer of a desired nucleotide sequence into a plant cell genome; (b) desired nucleotide sequence itself, which will generally comprise an expression cassette of (i) a plant active promoter, operably linked to (ii) the target sequence and\or enhancer as appropriate. The desired nucleotide sequence is situated between the border sequences and is capable of being inserted into a plant genome under appropriate conditions. The binary vector system will generally require other sequence (derived from *A. tumefaciens*) to effect the integration. Generally this may be achieved by use of so called "agro-infiltration" which uses *Agrobacterium*-mediated transient transformation. Briefly, this technique is based on the property of *Agrobacterium tumefaciens* to transfer a portion of its DNA ("T-DNA") into a host cell where it may become integrated into nuclear DNA. The T-DNA is defined by left and right border sequences which are around 21-23 nucleotides in length. The infiltration may be achieved e.g. by syringe (in leaves) or vacuum (whole plants). In the present invention the border sequences will generally be included around the desired nucleotide sequence (the T-DNA) with the one or more vectors being introduced into the plant material by agro-infiltration.

"Expression cassette" refers to a situation in which a nucleic acid is under the control of, and operably linked to, an appropriate promoter or other regulatory elements for transcription in a host cell such as a microbial or plant cell.

A "promoter" is a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter.

"Plant" species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*)), proso millet (*Panicum miliaceum*), foxtail millet (*Setaria italica*), finger millet, (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), *Nicotiana benthamiana*, potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers. The skilled person will appreciate that the tropism of the viral vectors disclosed herein varies. However, determining suceptibility to such viruses is well within the purview of the skilled person. Moreover, it may be possible to alter such specificity by recombinantly expressing receptors which facilitate viral entry into a plant cell.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

BRIEF DESCRIPTION OF THE DRAWINGS

FIG. 5 shows an initial comparison of Del-RNA-2 (expression vector 00 [FSC2-512] in FIG. 1) and HT (expression vector 01 [FSC2-512] in FIG. 1) for transient expression of the human anti-Human Immunodeficiency Virus antibody 2G12. The IgG Heavy chain was either in natural form (HL) or ER-retained (HEL) and infiltrated with the light chain and P19. (A) Expression of 2G12-HEL by del-RNA-2 leads to necrosis of infiltrated tissue whereas this does not occur for HT expression. (B) SDS-PAGE analysis of crude extracts of tissue infiltrated with the antibody heavy chains (delRNA-2 or HT) plus P19. For each sample crude extract from 5 mg of infiltrated tissue was loaded as was 1 µg of standard human IgG. A band corresponding to 2G12 is easily visible after coomassie staining. (C) Accumulation of antibody 2G12 after 5 days was measured by capture to protein A and surface plasmon resonance spectroscopy and represents the concentration following extraction in 2 volumes of buffer (PBS, 5 mM EDTA). Therefore, we can derive fresh weight concentrations approaching 150 mg/kg (for HT HEL) without any optimisation of plant incubation or extraction. Three samples were measured for each treatment.

EXAMPLES

Example 1

Figure 1:
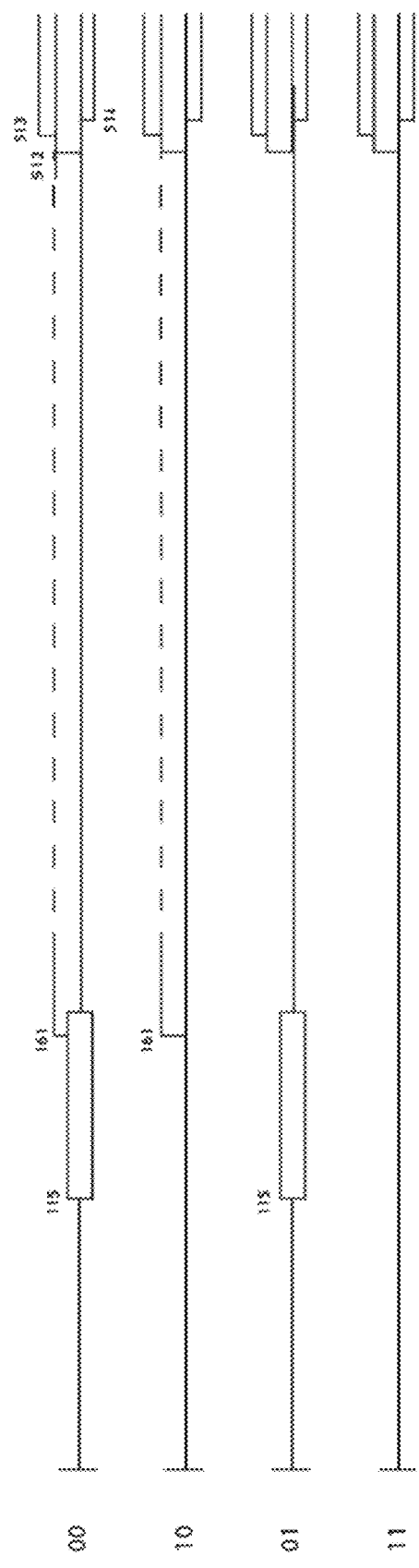
FIG. 1 shows a schematic diagram of CPMV expression vectors 00, 10, 01 and 11. In 00 expression vectors the initiation sites at positions 115 and 161 are intact. In 10 expression vectors the initiation site at positions 115 has been mutated but the initiation site at position 161 is intact. In 01 expression vectors the initiation site at positions 161 has been mutated but the initiation site at position 115 is intact. In 11 expression vectors the initiation sites at positions 115 and 161 are both mutated. CPMV expression vectors 00, 10, 01 and 11 also comprise an initiation site at either position 512 (FSC2-152), 513 (FSC2-513) or 514 (FSC2-514). Bars are used to indicate the initiation sites from which protein expression is expressed to occur.

1.1 Methods
Creation of Expression Vector FSC2 and its Derivatives

A useful cloning vector for the expression of foreign proteins from a pBinP-1-GFP-based plasmid (Cañizares et al., 2006) was created by excising the complete sequence of RNA-2 flanked by the Cauliflower mosaic virus (CaMV) 35S promoter and nopaline synthase (nos) terminator from pBinP-S2NT (Liu and Lomonossoff, 2002) and inserting it into mutagenesis plasmid pM81 W (Liu and Lomonossoff, 2006) as an AscI/PacI fragment. The resulting plasmid, pM81W-S2NT, was subjected to a single round of mutagenesis which simultaneously introduced four changes (see method in Liu and Lomonossoff, 2006) to give pM81B-S2NT-1. The mutagenesis removed two BspHI sites from the vector backbone and introduced a BspHI site (T/CATGA) around AUG 512 and a StuI site (AGG/CCT) after UAA 3299, the termination codon for the RNA-2-encoded polyprotein. Subsequently, the BamHI/AscI fragment was excised from pBinP-NS-1 (Liu et al., 2005) and ligated into similarly digested pM81B-S2NT-1, yielding pM81-FSC-1. This vector allows the whole of the RNA-2 ORF downstream of AUG 512 to be excised by digestion with BspHI and StuI and replaced with any sequence with BspHI and StuI (blunt)-compatible ends. The use of the BspHI site is important as it preserves the AUG at 512 and this initiator is used to drive translation of the inserted gene. To express the foreign gene in plants, the pM81-FSC-1-derived plasmid is digested with AscI and PacI and the fragment containing the expression cassette including the foreign sequences transferred to similarly digested pBIN-PLUS and the resulting plasmids are finally transformed into A. tumefaciens.

To improve the ease of cloning, expand the choice of applicable restriction enzymes, and to investigate the effect of reading frame on foreign gene expression, the whole RNA-2 ORF was replaced with a short polylinker. A combination of oligonucleotide insertion and site-directed mutagenesis resulted in pM81-FSC-2, which allows cloning with NruI (TCG/CGA) and either XhoI (C/TCGAG) or StuI. The terminal adenine of the NruI site lies at position 512 thereby preserving the AUG found here. The modifications altered nucleotides immediately 5' to the AUG at 512, however, a good context was maintained. Cloning GFP into pM81-FSC-2 such that its translation was initiated from an AUG at 512, 513, 514, or 515 gave the pM81-FSC-1 derived constructs pM81-FSC2-512, pM81-FSC2-513, pM81-FSC2-514, and pM81-FSC2-515. These pM81-based plasmids are the cloning vectors containing the expression cassettes which were then transferred into the binary vector to produce the expression vectors FSC2-512, FSC2-513 and FSC2-514 used in the Experiments shown in FIGS. 2 and 3. Differences between the sequence of the wt RNA-2 genome segment of CPMV and the pM81-FSC1 and pM81-FSC2 vectors are shown in Table 4.

Nucleotides altered in the vectors compared with the wt CPMV sequence are shown as capital letters.

Agrobacteria-mediated transient transformation following mobilisation into pBINPLUS (as outlined above for pM81-FSC-1) showed that lower protein levels are obtained when frame continuity between AUG 161 and the downstream AUG is not maintained. There was a significant decrease in the amount of GFP translated from the +1 and +2 positions relative to AUGs 161 and 512, whereas translation from the +3 position (that is, from 515 and back in frame) was as efficient as translation from an AUG at 512. To show that this was not due to weakened contexts of the AUGs at 513 and (to a lesser extent) 514, FSC2-515+ was created to initiate from +3 position but with the same poor context as FSC2-513. Expression from FSC2-515+ was as high as that achieved from FSC2-512 or 515, indicating that inferior context does not explain the reduction in expression from FSC2-513 and 514.

Given that the known mechanisms by which translation can escape the first-AUG rule are not known to require frame continuity, it is intriguing that efficient translation from a deleted RNA-2-based vector depends on frame continuity between AUG 161 and the downstream AUG. In order to understand, and hopefully overcome this phenomenon, a series of mutants were created with modifications to the 5' sequence of RNA-2. Complement pairs of oligonucleotides (see Table 3) were used in the site-directed mutagenesis of pM81-FSC2-512, 513, and 514. The mutations removed either AUG 115 (the start codon for the uORF), AUG 161 (without changing the amino acid sequence of the uORF), or both of these upstream initiation sites. Double mutations were made by mutagenizing the A115G mutants with the U162C oligos (Table 3).

Transient expression from these mutant transcripts was carried out as described for previous pM81-FSC-2 constructs. Analysis of expression of GFP from these mutants using coomassie-stained SDS-PAGE (FIG. 2) or UV light to visualise whole leaves (FIG. 3) shows a strong increase in expression in the absence of the AUG at 161. Furthermore, the removal of AUG 161 alone or both AUGs 115 and 161 alleviates the dependence on frame continuity between AUG 161 and the downstream AUG. In contrast, removal of just AUG 115 appears to enhance this dependency as well as generally inhibit translation. In conclusion, the uORF appears to function to down-regulate translation from AUG 161, which is both generally inhibitory and confers dependence on frame continuity.

Electron Microscopy of Sap Containing HBcAg Particles

Figure 6:
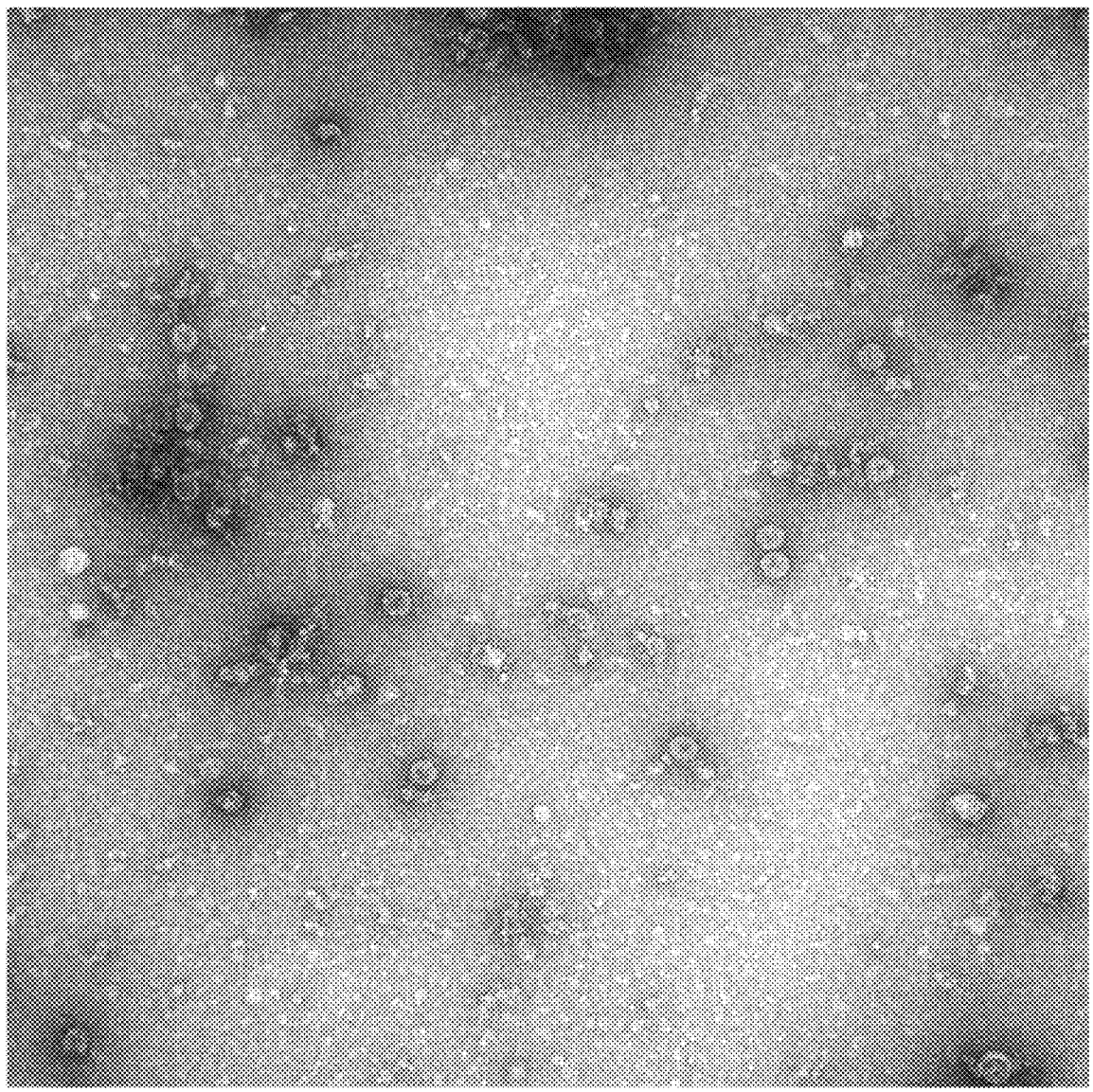
FIG. 6 shows an electron micrograph of assembled HBcAg particles, which were expressed using the HT (expression vector 01 [FSC2-512] in FIG. 1) expression system described herein. The assembled HBcAg particles appear as hollow spheres, about 30 nm in diameter. The sap containing the HBcAg particles was not concentrated before the electron micrograph was taken, although unwanted salts were removed. Therefore, the electron micrograph represents the concentration of HBcAg particles in the sap.

The sap used for the electron micrograph of the assembled HBcAg particles shown in FIG. 6 was prepared as follows. Leaf tissue was extracted in 2 volumes of Tris/NaCl buffer and exchanged for TE without concentration on a 100 kDa MWCO column. The final concentration of HBcAg was approximately 0.2 mg/ml as judged by comparison to standard on a coomassie stained SDS-PAGE gel.

1.2 Results (1) Effect of Altering Relative Phases of the Initiation Sites at Position 161 (AUG161) and 512 (AUG512).

Figure 2:
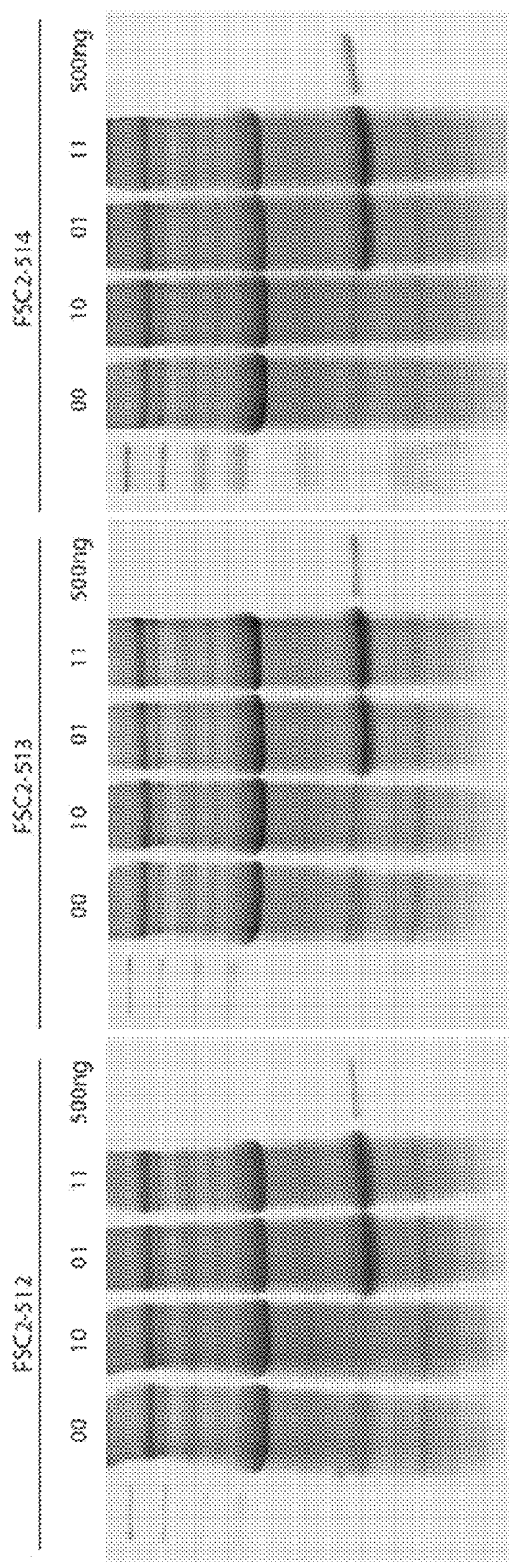
FIG. 2 shows the level of soluble green fluorescent protein (GFP) expressed in plants transfected with the CPMV expression vectors schematically illustrated in FIG. 1. In expression vectors FSC2-512, FSC2-513 and FSC2-514, the gene encoding GFP was inserted after the initiation codon at position 512, 513 and 514, respectively. The lanes of the SDS-PAGE gels are marked 00, 10, 01 and 11, depending on which of the initiation sites in the CPMV vector, at positions 115 and 161, are intact or mutated. The lane marked '500 ng' shows the position of a band corresponding to 500 ng of GFP protein and thus indicates the expected position of GFP protein expressed from the CPMV expression vectors. The left hand lane of each SDS-PAGE gel shows the position of protein size markers.

To achieve this extra nucleotides were inserted immediately upstream of AUG512 (FSC2-512) to move the AUG to position 513, 514 and 515 (FSC2-513, FSC2-514 and FSC2-515) (FIG. 1). Putting AUG512 out-of-phase with AUG 161 (FSC2-513 and FSC2-514) gave less GFP expression as judged by fluorescence (FIG. 3) and Coomassie-stained gels (FIG. 2). Restoring the phase (FSC2-515) brought expression back to levels seen with the natural situation (FSC2-512). The conclusion is that when AUG161 is present, initiation at a downstream AUG is most efficient when it is in-phase with the AUG at position 161.

(2) Removal of the Initiation Site at Position 115 (AUG115) Coupled with Altering Relative Phases of the Initiation Sites at Position 161 (AUG161) and 512 (AUG512).

Figure 3:
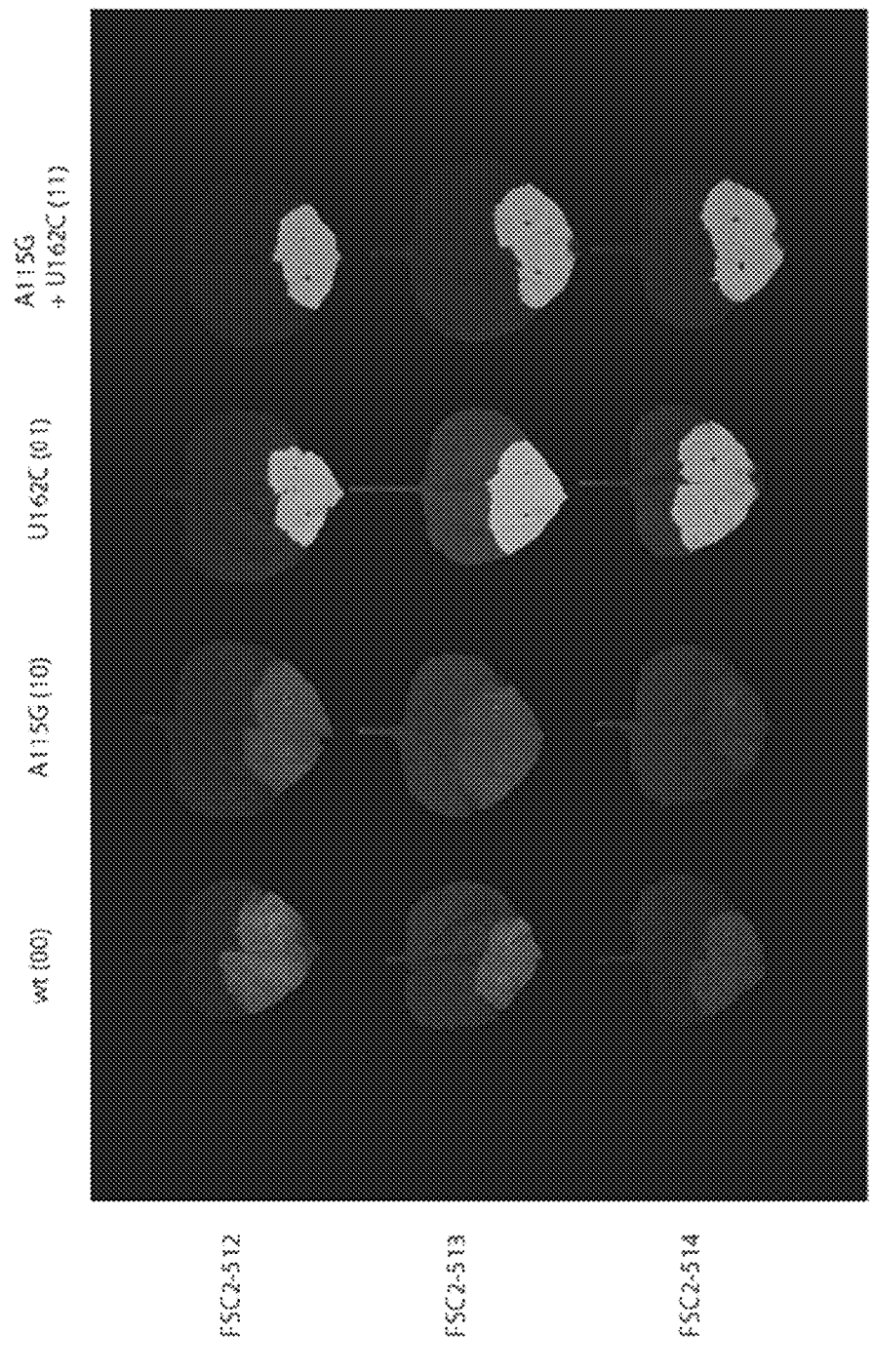
FIG. 3 shows the level of GFP expression in *Nicotiana benthamiana* leaves transfected with the same CPMV expression vectors used in the experiment illustrated in FIG. 2. The pale regions at the tips of the leaves correspond to regions of GFP expression. Mutations made in order to inactivate the initiation sites at positions 115 and/or 161 in expression vectors 10, 01 and 11 are also indicated.
Figure 4:
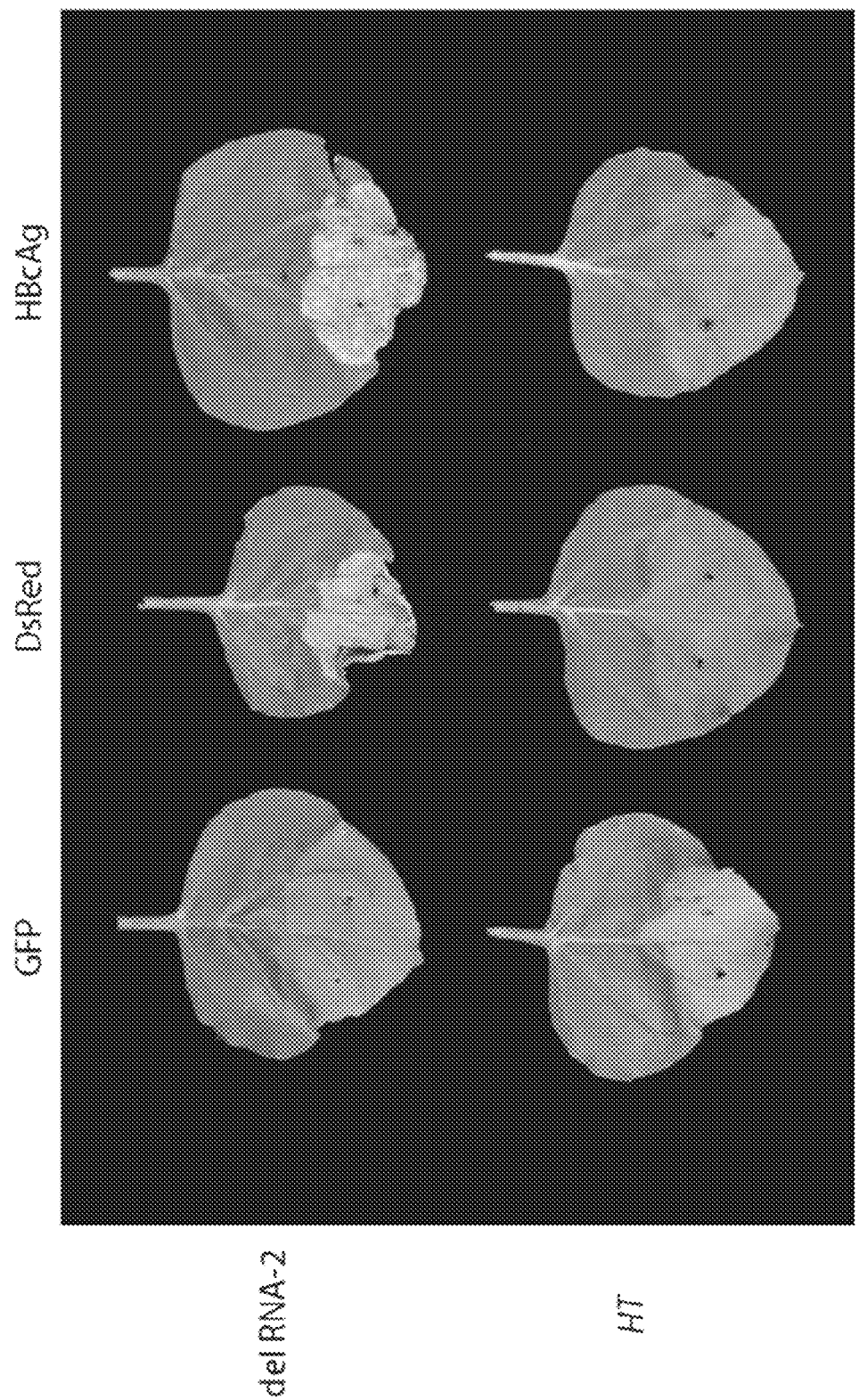
FIG. 4 shows a comparison of Del-RNA-2 (expression vector 00 [FSC2-512] in FIG. 1) and HT (expression vector 01 [FSC2-512] in FIG. 1) for transient expression of green fluorescent protein (GFP), Discosoma red fluorescent protein (DsRed), and the hepatitis B core antigen (HBcAg). delRNA-2 or HT clones for each protein were infiltrated with the silencing suppressor P19. (A) Tissue 7 days after infiltration with delRNA-2 constructs becomes necrotic when DsRed or HBcAg is expressed whereas this is not the case for HT driven expression. In fact, tissue expressing DsRed by HT looks visibly red under day light conditions. (B) Coomassie-stained SDS-PAGE analysis of protein expression. The prominent bands corresponding to recombinant proteins as indicated were confirmed by western blotting. 1-marker, 2-uninfiltrated tissue, 3-delRNA-2 construct, 4-HT construct, 5-commercial standard where available. Crude extracts from approximately 5 mg of infiltrated tissue were loaded per lane as was 2 µg of GFP standard and 2 µg of HBcAg standard. No standard for DsRed was available at the time.

Removal of AUG115 has little or no effect when GFP expression is driven from AUG512 i.e. when this second AUG is in phase with AUG161 (see lanes labelled 10 in FIGS. 2 and 3). However, deletion of AUG115 when the second AUG is out-of-phase with AUG161 (513, 514) results in virtually no GFP expression (see lanes labelled 10 in FIGS. 2 and 3). Conclusion: AUG115 is somehow involved in the ability of ribosomes to by-pass AUG161 and reach AUG512. However, this requires the downstream AUG to be in the correct phase.

(3) Effect of Removal of the Initiation Site at Position 161 (AUG161)

The effect of this mutation is incredibly dramatic with GFP expression levels reaching 20-30 times the amount found when AUG161 is present (see lanes labelled 01 in FIGS. 2 and 3). Furthermore, it no longer appears to matter which phase AUG512 is in, though in the absence of AUG161, the idea of phase does not mean much. In addition the presence or absence of AUG115 makes no difference (see lanes labelled 11 in FIGS. 2 and 3).

When using the delRNA-2 (expression vector 00 [FSC2-512] in FIG. 1) constructs for DsRed and HBcAg expression, within 5 days infiltrated patches have lost turgor pressure and become chlorotic (pale). By 7 days the tissue appears grey and is completely dead. When using HT (expression vector 01 [FSC2-512] in FIG. 1), the tissue remains turgid after 7 days and the only sign of stress is slight chlorosis of HBcAg expressing tissue. When the heavy chain of the 2G12 IgG is expressed by delRNA-2 and retained in the ER, chlorosis is evident after 7 days, whereas for HT this is not observed. The level of necrosis seen in plants when using HT to express a heterologous protein is thus much lower, despite the higher level of heterologous protein expression achieved, than when using delRNA-2 to express the heterologous protein.

Discussion

Very high levels of foreign gene expression can be expressed from the deRNA-2 constructs by deleting AUG161. At present, using GFP, we estimate the levels as 25-30% of total soluble protein (TSP) or approximately 1 gram expressed protein per Kg leaves. This is a tremendous level and the approach we use is extremely simple. The fact that we no longer need to preserve a reading frame means that user-friendly vectors with polylinkers can be produced.

Example 2

2.1 Background

As described in Example 1, to investigate the features necessary for the 5' untranslated region (UTR) of CPMC RNA-2 necessary for efficient expression, the present inventors addressed the role of two AUG codons found within the 5' leader sequence upstream of the main initiation start site. The inventors demonstrated that deletion of an in-frame start codon (161) upstream of the main translation initiation site (512) led to a massive increase in foreign protein accumulation.

Using this system the inventors have shown that by 6 d postinfiltration, a number of unrelated proteins, including a full-size IgG and a self-assembling virus-like particle, were expressed to >10% and 20% of total extractable protein, respectively. Thus, this system provides an ideal vehicle for high-level expression that does not rely on viral replication of transcripts.

This new system (as exemplified by expression vector 01 [FSC-512] in FIG. 1) has been called "CPMV-HT" for hyper-translatable Cow Pea Mosaic Virus protein expression system.

The HT-CPMV system shows dramatic increases in protein levels and thus is an excellent method for the rapid, high-level expression of foreign proteins in plants.

A growing array of binary vectors has been developed for plant transformation over the past 25 years (Hellens et al., 2000b; Veluthambi et al., 2003; Lee and Gelvin, 2008). The main aim of these developments has thus far focused on improving stable integration by, for example, expanding the host range for *Agrobacteria* (Hiei et al., 1994), the creation of a series of vectors that allow a choice of selectable markers, expression cassettes and fusion proteins (exemplified by the pCAMBIA range of open source binary vectors, or by developing systems for minimising extraneous DNA integration and marker-free transformation (for example pCLEAN; Thole et al., 2007).

Binary vectors have also been engineered to replicate at low copy numbers to reduce the frequency of multiple integration events of the same transgene, as this can lead to gene silencing (Johansen and Carrington, 2001).

However, for transient expression, ensuring efficient integration into the host nucleus and the presence of marker for in planta selection are not strictly required. Furthermore, upon agro-infiltration each cell is flooded with T-DNA molecules, which are thought to be transcriptionally competent in the nucleus even without genome integration (Janssen and Gardner, 1989; Narasimhulu et al., 1996). This suggests that transient expression could benefit from higher copy number binary plasmids.

Another area of improvement of binary vectors has been the reduction in size of the vector backbone. Two prominent examples that continue to demonstrate the benefits of smaller plasmids are pPZP (Hajdukiewicz et al., 1994) and pGREEN (Helens et al., 2000a). In addition to improving the efficiency of cloning procedures and bacterial transformation, these vectors have provided templates for expression systems that rely on multiple cassettes present on a single T-DNA (Tzfira et al., 2005; Thole et al., 2007).

The present example discloses non-obvious refinements of this vector which facilitates its practical use by permitting the cloning to be done in a single step, rather than requiring subcloning of expression cassettes between the cloning vector (e.g. pM81-FSC2) and expression systems (e.g. PBINPLUS). More specifically, the results herein show it was possible to drastically reduce the size of pBINPLUS without compromising performance in terms of replication and TDNA transfer. Furthermore, elements of the CPMV-HT system have been incorporated into the resulting vector in a modular fashion such that multiple proteins can be expressed from a single T-DNA. These improvements have led to the creation of a versatile, high-level expression vector that allows efficient direct cloning of foreign genes.

Figure 9:
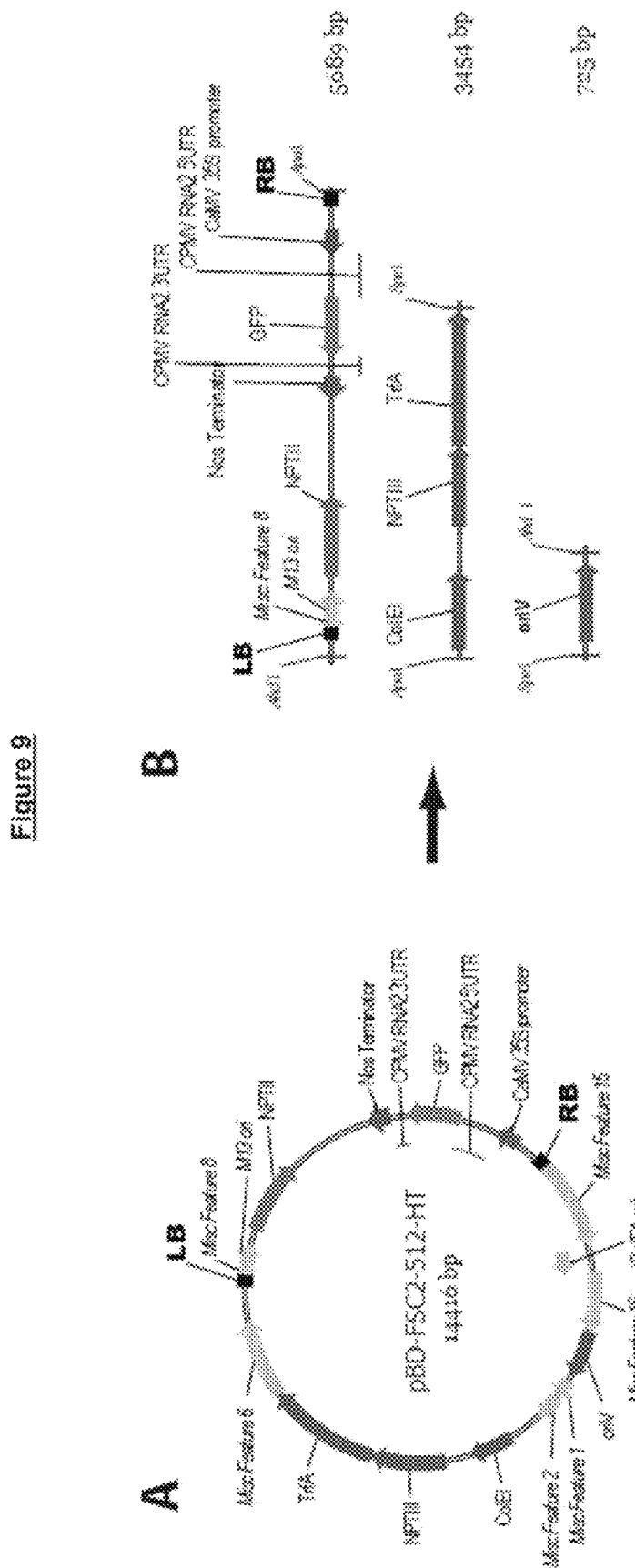
FIG. 9 shows a schematic representation of the construction of pEAQ. (A) Starting pBINPLUS-based plasmid with extraneous sequence shown in grey. (B) PCR products containing essential elements of the binary vector. (C) Intermediate plasmid following 3-part ligation of end-tailored PCR products. (D) Final plasmid following amplification and subsequent ligation of two fragments from the intermediate.

2.2 Materials and Methods pBD-FSC2-512-U162C (HT), contains the FSC2-512-U162C cassette (see Example 1) inserted into the PacI/AscI sites of pBINPLUS (van Engelen et al., 1995). The essential segments of this plasmid (see below) were amplified with the high fidelity polymerase, PHUSION (New England Biolabs) using oligonucleotides encoding unique restriction enzyme sites for re-ligation (Table 1). The T-DNA region was amplified with a sense primer homologous to sequence upstream of a unique Ahdl site (pBD-LB-F) and an antisense primer that included an ApaI site (pBD-RB-ApaI-R). A region including the ColE1 origin of replication, the NPTIII gene, and the TrfA locus was amplified with a sense primer that included an ApaI site (pBD-ColE1-ApaI-F), and an antisense primer that included a SpeI site (pBD-TrfA-SpeI-R). The RK2 origin of replication (OriV) was amplified with a sense primer that included a SpeI site (pBD-oriVSpeI-F) and an antisense primer that included an Ahdl site (pBD-oriV-Ahdl-R). Following purification, the products were digested according to the unique restriction sites encoded at their termini and mixed for a three-point ligation. This resulted in the plasmid pEAQbeta, for which the ligation junctions were verified by sequencing. A deletion of approximately 1.2 kb from the T-DNA which had removed a portion of the nos terminator of the CPMV-GFP-HT cassette was detected. Therefore, a portion of the terminator including the right border from pBD-FSC2-GFP-HT was re-amplified with primers pMini>pMicroBIN-F2 and pBD-RB-ApaI-R, as was the pEAQbeta backbone, including the right border, using primers pBD-ColE1-ApaI-F and pMini>pMicroBIN-R (Table 1). The purified products were digested with ApaI and FseI and ligated to give pEAQ (FIG. 9).

The P19 gene flanked by 35S promoter and 35S terminator was amplified from pBIN61-P19 (Voinnet et al., 2003) using either 35SP19-PacI-F and 35SP19-AscIR, or 35SP19-FseI-F and 35S-P19-FseI-R as primers (Table 1). The NPTII gene flanked by the nos promoter and terminator was amplified from pBD-FSC2-GFPHT using primers pBD-NPTII-FseI-F and pBD-NPTII-FseI-R (Table 1). Following A-tailing, the amplified cassettes were ligated into pGEM-T easy (Promega). The P19 cassette excised from pGEM-T easy with FseI was ligated into FseI-digested pEAQ-GFP-HT to give pEAQexpress-GFP-HT. The NPTII cassette excised with FseI was ligated into FseI-digested pEAQ-GFP-HT in both directions to give pEAQselectK-GFP-HT and pEAQselectK(rev)-GFP-HT. The NPTII cassette was also excised with PacI/AscI and ligated into the AsiSI/MluI sites of pEAQselectK-GFP-HT to give pEAQspecialK-GFP-HT. The P19 in pGEM-T was subjected to site-directed mutagenesis by the QUICKCHANGE method (Stratagene) to effect the conversion of Arginine43 to a tryptophan residue using primers P19-R43W-F and P19-R43W-R. The mutant P19 cassette was released with PacI/AscI digest and inserted into the AsiSI/MluI sites of pEAQselectK-GFP-HT to give pEAQspecialKm-GFP-HT.

Oligonucleotides encoding the sense and antisense strands of a short polylinker (Table 1) were annealed leaving the downstream half of an NruI site at the 5'end and an overhang matching that of XhoI at the 3' end. The annealed oligos were ligated with NruI/XhoI digested pM81-FSC2-A115G-U162C (see above) to give pM81-FSC2-POW. The NruI site was removed from the P19 cassette in pGEM-T by site-directed mutagenesis (QUICKCHANGE; Stratagene) with the primers P19-ΔNruI-F and P19-ΔNruI-R, and was re-inserted into the AsiSI/MluI sites of pEAQselectK-GFP-HT to give pEAQspecialKΔNruI-GFP-HT which showed no reduction in expression compared to pEAQspecialK-GFP-HT (data not shown). The PacI/AscI fragment from pM81-FSC2-POW was then released and inserted into similarly digested pEAQspecialKΔNruI-GFP-HT thereby replacing the GFP HT expression cassette and yielding pEAQ-HT. GFP was amplified from pBD-FSC2-GFP-HT with a set of four primers (Table 1) in three combinations for insertion into pEAQ-HT: GFP-Age-F and GFP-XhoI-R; GFP-Age-F and GFP-XmaI-R; and GFP-XmaI-F and GFP-XhoI-R. Purified PCR products were digested with the enzymes specified in their primers and inserted into appropriately digested pEAQ-HT to give pEAQ-HT-GFP, pEAQ-HT-GFPHis, and pEAQ-HT-HisGFP.

TABLE 1

Oligonucleotides used for amplification and mutagenesis. Restriction enzyme sites, or parts thereof, are shown in lower case, and mutations underlined in bold.

| SEQ ID NO: | Oligo | Sequence | Function |
|---|---|---|---|
| 14 | pBD-LB-F | GCCACTCAGCTTCCTCAGCGGCTTT | Sense primer for amplification of the region 6338-12085 of pBD-FSC2-GFP-HT |
| 15 | pBD-RB-ApaI-R | TATTAgggcccCCGGCGCCAGATCTGGGGAACCCTGTGG | Antisense primer for amplification of the region 6338-12085 of pBD-FSC2-GFP-HT with ApaI site |
| 16 | pBD-ColEI- | GACTTAgggcccGTCCATT | Sense primer for |

TABLE 1-continued

Oligonucleotides used for amplification and mutagenesis. Restriction enzyme sites, or parts thereof, are shown in lower case, and mutations underlined in bold.

| SEQ ID NO: | Oligo | Sequence | Function |
|---|---|---|---|
|  | ApaI-F | TCCGCGCAGACGATGACGTCACT | amplification of the region 1704-5155 of pBD-FSC2-GFP-HT with ApaI site |
| 17 | pBD-TrfA-SpeI-R | GCATTAactagtCGCTGGCTGCTGAACCCCCAGCCGGAACTGACC | Antisense primer for amplification of the region 1704-5155 of pBD-FSC2-GFP-HT with SpeI site |
| 18 | pBD-oriV-SpeI-F | GTAGCactagtGTACATCACCGACGAGCAAGGC | Sense primer for amplification of the region 14373-670 of pBD-FSC2-GFP-HT with SpeI site |
| 19 | pBD-oriV-AhdI-R | CAGTAgacaggctgtcTCGCGGCCGAGGGGCGCAGCCC | Antisense primer for amplification of the region 14373-670 of pBD-FSC2-GFP-HT with AhdI site |
| 20 | pMini > pMicroBIN-F2 | ggccggccacgcgtTATCTGCAGAgcgatcgcGAATTGTGAGCGGATAACAATTTCACACAGGAAACAGCTATGACC | Sense primer for amplification of the region 2969-85 of pEAQbeta with FesI-MluI-AsiSI sites |
| 21 | pMini > pMicroBIN-R | gcgatcgcTCTGCAGATAacgcgtggccggccCTCACTGGTGAAAAGAAAAACCACCCCAGTACATTAAAAACGTCC | Antisense primer for amplification of the region 2969-85 of pEAQbeta with AsiSI-MluI-FesI sites |
| 22 | 35SP19-PacI-F | ttaattaaGAATTCGAGCTCGGTACCCCCCTACTCC | Sense primer for amplification of the 35S-P19 cassette with PacI site |
| 23 | 35SP19-AscI-R | ggcgcgccATCTTTTATCTTTAGAGTTAAGAACTCTTTCG | Antisense primer for amplification of the 35S-P19 cassette with AscI site |
| 24 | 35SP19-FseI-F | ggccggccGAATTCGAGCTCGGTACCCCC | Sense primer for amplification of the 35S-P19 cassette with FseI site |
| 25 | 35SP19-FseI-R | ggccggccATCTTTTATCTTTAGAGTTAAG | Antisense primer for amplification of the 35S-P19 cassette with FseI site |
| 26 | pBD-NPTII-FseI-F | ggccggccTACAGTATGAGCGGAGAATTAAGGGAGTCACG | Sense primer for amplification of the NPTII cassette from pBD-FSC2-GFP-HT with FseI site |
| 27 | pBD-NPTII-FseI-R | ggccggccTACAGTCCCGATCTAGTAACATAGATGACACCGCGC | Antisense primer for amplification of the NPTII cassette from pBD-FSC2-GFP-HT with FseI site |
| 28 | P19-R43W-F | CGAGTTGGACTGAGTGGTGGCTACATAACGATGAG | Sense primer for mutagenesis of arginine 43 of P19 to a tryptophan residue |
| 29 | P19-R43W-R | CTCATCGTTATGTAGCCACCACTCAGTCCAACTCG | Antisense primer for mutagenesis of arginine 43 of P19 to a tryptophan residue |
| 30 | P19-ΔNruI-F | CCGTTTCTGGAGGGTCTCGAACTCTTCAGCATC | Sense primer for the silent mutagenesis of the NruI restriction site within P19 |

TABLE 1-continued

Oligonucleotides used for amplification and mutagenesis. Restriction enzyme sites, or parts thereof, are shown in lower case, and mutations underlined in bold.

| SEQ ID NO: | Oligo | Sequence | Function |
|---|---|---|---|
| 31 | P19-ΔNruI-R | GATGCTGAAGAGTTCGA GACCCTCCAGAAACGG | Antisense primer for the silent mutagenesis of the NruI restriction site within P19 |
| 32 | POW-F | cgaccggtATGCATCACCA TCACCATCATcccgggCAT CACCATCACCATCACTAGc | Sense oligo for polylinker, POW |
| 33 | POW-R | tcgagCTAGTGATGGTGA TGGTGATGcccgggATGA TGGTGATGGTGATGCAT accggttcg | Sense oligo for polylinker, POW |
| 34 | GFP-AgeI-F | atcggaccggtatgactagcaaag gagaagaac | Sense oligo for amplification of GFP with AgeI site |
| 35 | GFP-XmaI-F | atccgacccgggactagcaaagg agaagaactttttcac | Sense oligo for amplification of GFP with XmaI site and no start codon |
| 36 | GFP-XmaI-R | atccgacccgggtttgtatagttcat ccatgcc | Antisense oligo for amplification of GFP with XmaI site and no termination codon |
| 37 | GFP-XhoI-R | cgatcctcgagttatttgtatagtt catccatgcc | Antisense oligo for amplification of GFP with XhoI site |

2.3 Results 2.3.1 pBINPLUS Contains at Least 7.4 kb of Extraneous Sequence

Expression from CPMV-HT enables the production of extremely high levels of recombinant proteins. Nevertheless it was desired to further improve the system and its use for transient transformation.

The first area of improvement relates to the fact that small plasmids are more efficient than larger ones in ligation reactions and bacterial transformation procedures. Comparisons with the structures of smaller binary vectors indicated that pBINPLUS likely contains significant amounts of extraneous sequence. Four elements of pBINPLUS were determined to be essential for proper function as a binary vector: the T-DNA, the RK2 (OriV) broad host range replication origin, the NPTIII gene conferring resistance to kanamycin (Trieu-Cuot and Courvalin, 1983), and TrfA from RK2 that promotes replication (FIG. 9). Bioinformatic analysis of the remaining backbone sections show them to be artefacts of the construction of pBIN19, which relied on the presence of appropriate restriction sites within parent plasmids (Bevan, 1984). These observations are confirmed by a report on the complete sequencing of pBIN19 (Frisch et al., 1995). pBIN-PLUS includes the non-essential ColE1 replication origin for higher copy number in E. coli. Approximately 2.6 kb of superfluous DNA can be found within the T-DNA. This includes the NPTII selectable marker for plant transformation that is not required for transient expression. Overall, the total amount of extraneous sequence within pBINPLUS appears to be in excess of 7.2 kb.

2.3.2 pEAQ Series Construction

Figure 10:
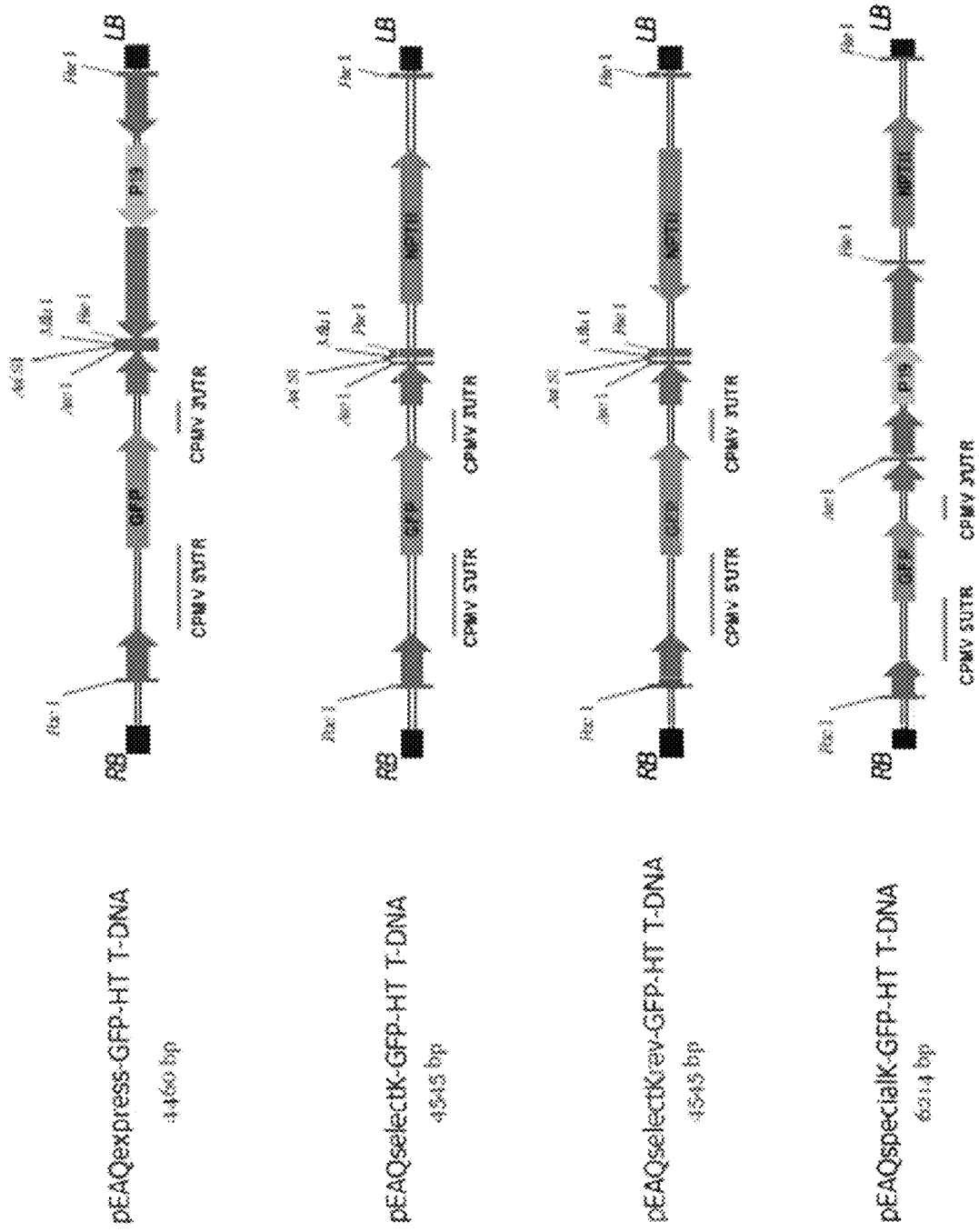
FIG. 10 shows a schematic representation of the T-DNAs of the main pEAQ derivatives. The T-DNAs contain either or both of the P19 and NPTII cassettes as indicated leaving possible cloning into restriction sites as indicated.

In order to monitor the effects on expression resulting from modifications to vector, we chose to start with the pBINPLUS-derived plasmid, pBD-FSC2-512-U162C(HT). Three regions, consisting of the T-DNA, the RK2 (OriV) replication origin, and a segment containing the ColE1 origin, NPTIII, and TrfA, were amplified by PCR from pBD-FSC2-GFP-HT. Ligation of these three fragments resulted in the plasmid pEAQbeta (FIG. 9), which is 4584 bp smaller than its parent plasmid. A further round of PCR amplification of pEAQbeta removed 2639 bp of non-essential sequence from the T-DNA region and inserted three unique restriction sites, AsiSI, MluI, and FseI. AsiSI/MluI digestion is compatible with the insertion of PacI/AscI fragments, and is therefore, extremely useful for cloning multiple cassettes from all previous CPMV cloning vectors. FseI provides a unique 8-base recognition site useful for interchanging different selection markers or silencing suppressor cassettes. The resulting pEAQGFP-HT plasmid is less than half the size of pBINPLUS and without the CPMVHT expression cassette would be only 5137 bp, making it one of the smallest known binary vectors (FIG. 9). The entire pEAQ plasmid was sequenced and it was discovered that the RK2 origin of replication was in the reverse orientation to that previously reported (Frisch et al., 1995) and is therefore indicated in the correct orientation in pEAQ-GFP-HT.

pEAQ-GFP-HT was used as a starting point for the inclusion of various additional features into the T-DNA (FIG. 10). The NPTII cassette from pBINPLUS was reinserted into the FseI site of pEAQ in both the forward and reverse orientations relative to the GFP-HT cassette to give pEAQselectK-GFP-HT and pEAQselectK(rev)-GFP-HT. The 35S-P19 cassette was inserted into the FseI site to give pEAQexpress-GFP-HT. Finally, the 35S-P19 cassette was inserted into the MluI/AsiSI sites of pEAQselectK-GFP-HT to give pEAQspecialK-GFP-HT. Thus, a series of small binary vectors for easy and quick transient expression were constructed.

2.3.3 Reduction in Size does not Compromise Transient Expression from pEAQ

Figure 11:
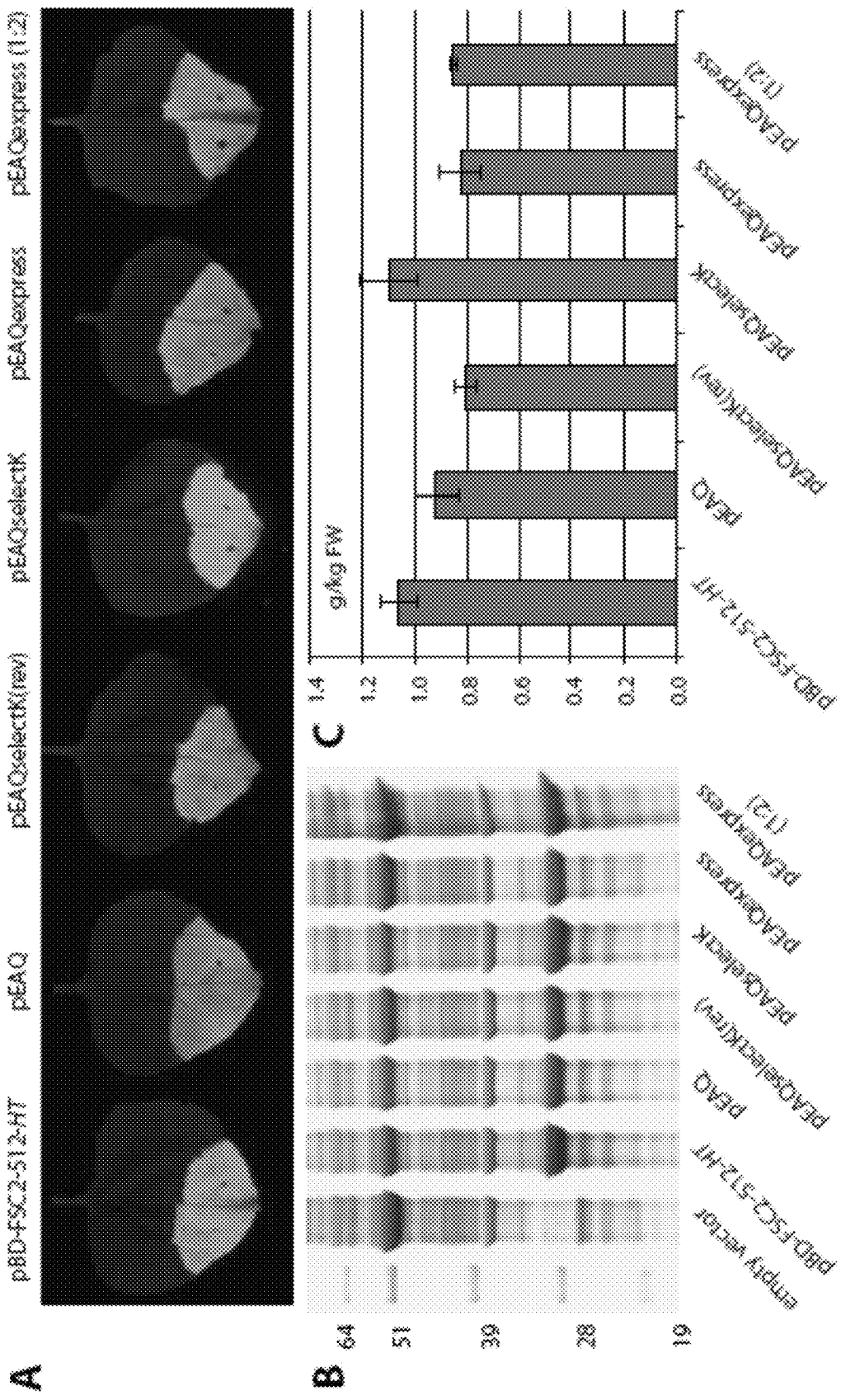
FIG. 11 shows expression levels of GFP generated by pEAQ vectors compared to its parent plasmid pBB-FSC2-512-HT. Tissue was analysed 6 days after infiltration with P19 and the vector indicated except for pEAQexpress, which was infiltrated alone at the standard OD, or at a two-fold dilution. (A) Leaves visualised under UV light, (B) coomassie-stained 12% SDS-PAGE, and (C) spectrofluorometric analysis.

Agro-infiltration of the pEAQ series of vectors shows that the large reduction in size does not significantly compromise expression levels in transient assays. Coinfiltration of pEAQ-GFP-HT, and pEAQselectK(rev)-GFP-HT with P19 provided by pBIN61-P19, resulted in levels of expression not significantly different to the co-infiltration of pBD-FSC2-512-HT and P19. This can be seen under UV illumination (FIG. 11A), SDS-PAGE (FIG. 11), and spectrofluorescence measurements of GFP in protein extracts (FIG. 11C). Interestingly, the orientation of the NPTII cassette within the T-DNA appears to affect expression level. pEAQselectK shows a marked improvement compared to the otherwise identical pEAQselectK(rev), which results in a reduction in GFP accumulation.

Figure 7:
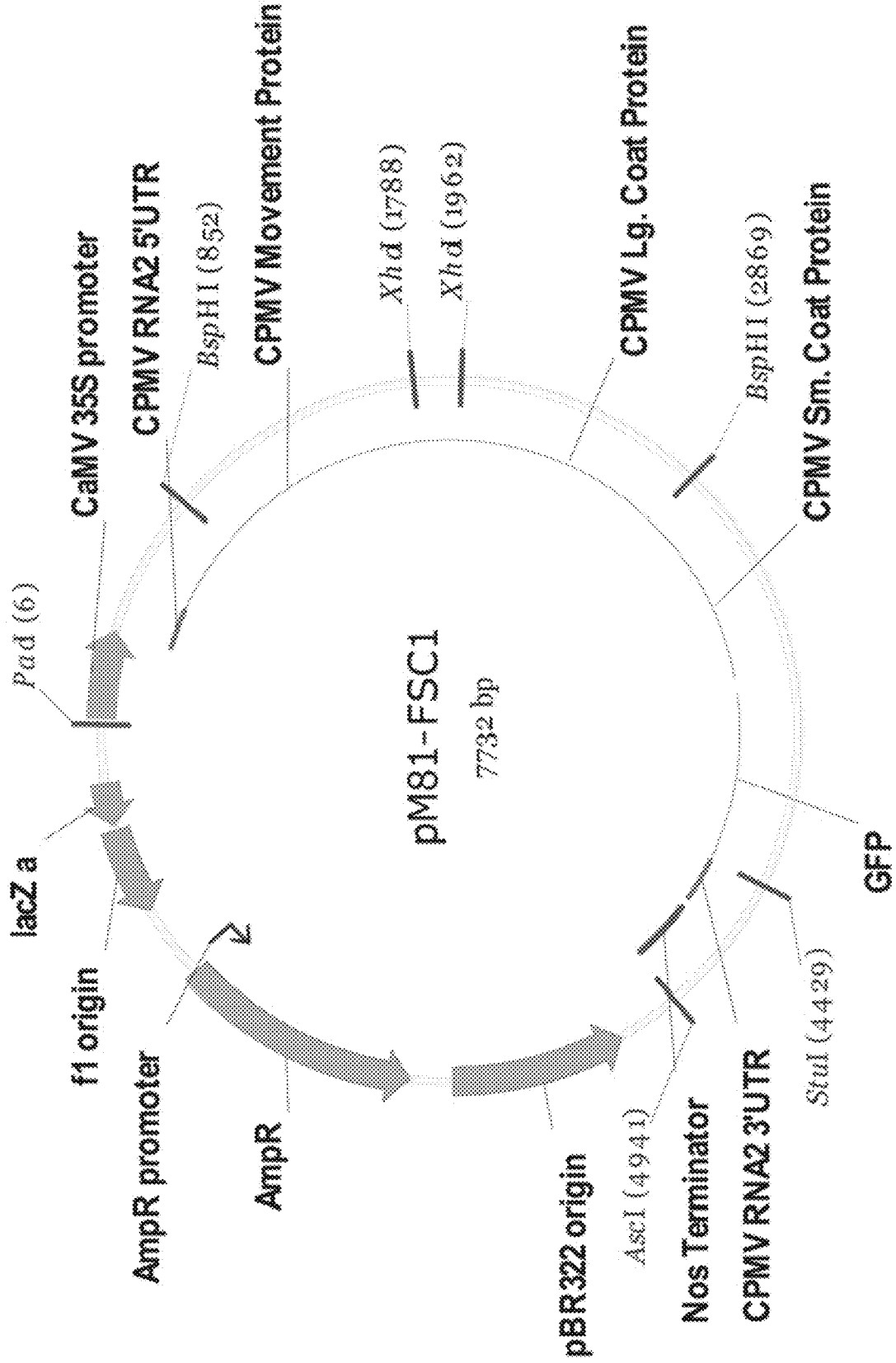
FIG. 7 shows the vector pM81-FSC1.
Figure 8:
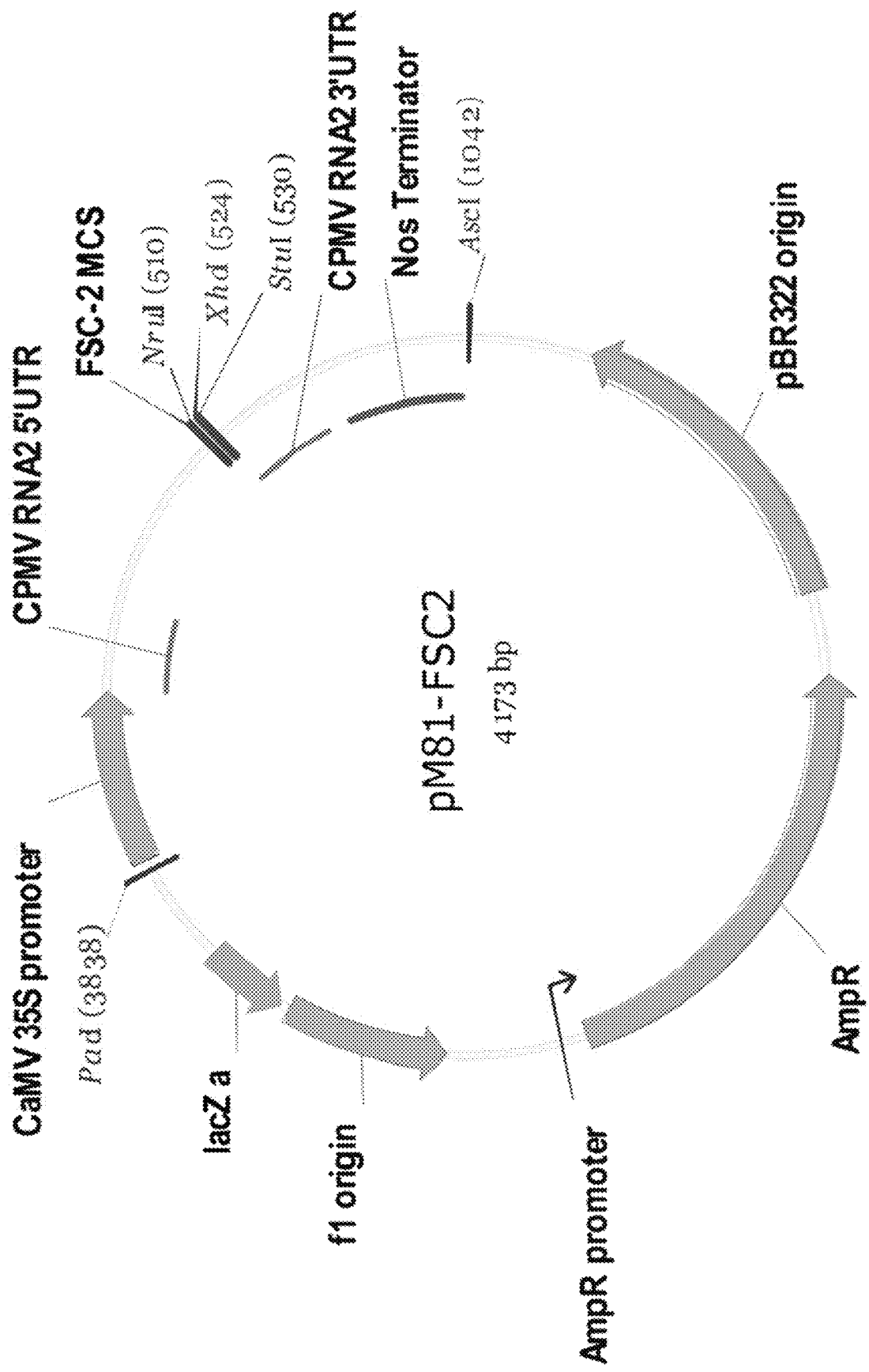
FIG. 8 shows the vector pM81-FSC2.

Theoretically, the incorporation of a suppressor of silencing cassette into pEAQ should not affect its ability to improve transient expression level from a foreign gene to be expressed from the same T-DNA. Indeed, the infiltration of pEAQexpress-GFP-HT alone also resulted in expression levels similar to, or better than, pBD-FSC2-GFP-HT (FIG. 7.3). Furthermore, to test the efficiency of pEAQexpress, the Agrobacterium culture was diluted two-fold, such that the final optical density (OD) was that of each individual culture of the coinfiltrations.

As expected, this resulted in similarly high expression levels and demonstrates that incorporating both the gene of interest and the suppressor of silencing onto the same T-DNA allows the use of half the amount of Agrobacteria (FIG. 11). Therefore, CPMV-HT may be used to express high levels of foreign protein when all components are present on the same T-DNA.

2.3.4 Mutant P19 can Suppress Silencing of a Transgene in a Transient Assay

Figure 12:
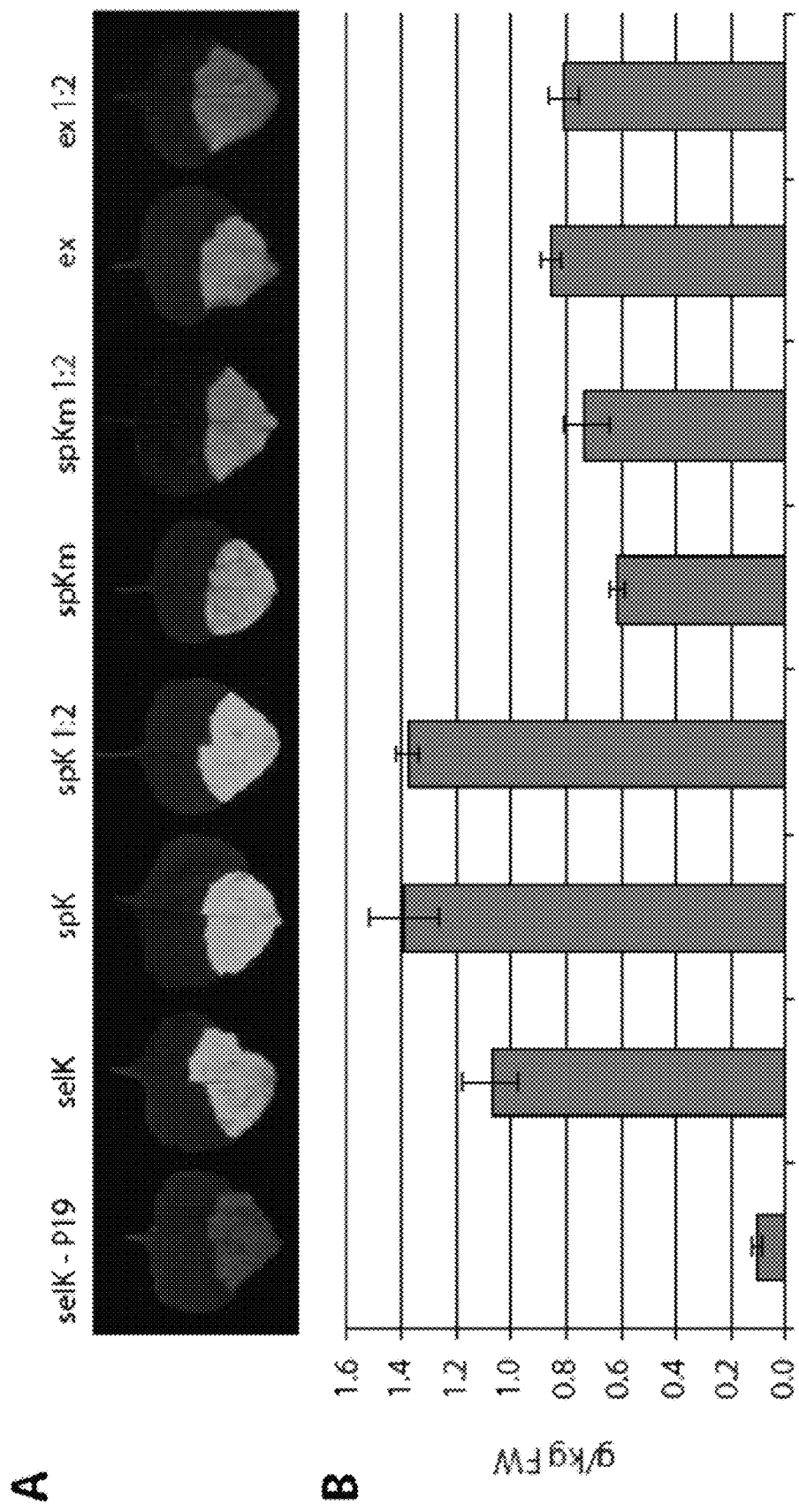
FIG. 12 shows the ability of P19(R43W) to enhance GFP expression compared to wild type P19. Tissue was analysed 6 days after infiltration with pEAQselectK at two-fold dilution (selK-P19), pEAQselectK and P19 (selK), pEAQspecialK (spK), pEAQspecialK at two-fold dilution (spK 1:2), pEAQspecialKm (spKm), pEAQspecialKm at two-fold dilution (spKm 1:2), pEAQexpress (ex), and pEAQexpress at two-fold dilution (ex 1:2). (A) Leaves visualised under UV light and (B) spectrofluorometric analysis.

In order to take advantage of the increase in expression afforded by the forward orientation of the NPTII cassette within the T-DNA, the P19 cassette was inserted between the AsiSI and MluI sites in pEAQselectK-GFP-HT to give pEAQspecialK-GFP-HT (FIG. 10). The presence of P19 on the same T-DNA as the sequence of GFP results in similar levels of expression to pEAQselectK-GFPHT co-infiltrated with P19 (FIG. 12). This is more than the expression generated by pEAQexpress-GFP-HT, and appears to be due to the presence of the NPTII cassette (FIG. 12). On the other hand, the lower expression from pEAQexpress could be due to the different position and orientation of the P19 cassette within the T-DNA. Nevertheless, as with pEAQexpress, pEAQspecialK vectors give high-level expression with Agrobacteria suspensions at half the final OD of that used when two cultures must be co-infiltrated.

Combining the foreign gene expression cassette with a P19 cassette and a selectable marker makes it possible to test the performance of CPMV-HT in transgenic plants. However, the constitutive expression of suppressors of silencing like P19 can result in severe phenotypes due to their interference with endogenous gene silencing associated with developmental processes (Silhavy and Burgyan, 2004). A recently characterised mutation of P19 (R43W) has been proposed to have a reduced activity towards endogenous gene silencing and therefore may be a better candidate for the suppression of transgene silencing in stable transformants (Scholthof, 2007). To investigate the feasibility of stable transformation with the CPMV-HT system, both wt and the mutant P19 were inserted into the T-DNA of pEAQselectK-GFP-HT to assay the variants transiently. As shown by, UV illumination of infiltrated leaves, SDS-PAGE of protein extracts, and spectrofluorometric measurements of GFP levels, the mutant P19 in pEAQspecialKm is approximately half as effective in improving foreign gene expression as the wt P19 in pEAQspecialK (FIG. 12). This represents the first study on the effect of the R43W mutation in P19 on the ability to suppress silencing of a transgene.

Example 3

High Level IgG Expression from a Single Plasmid

Figure 13:
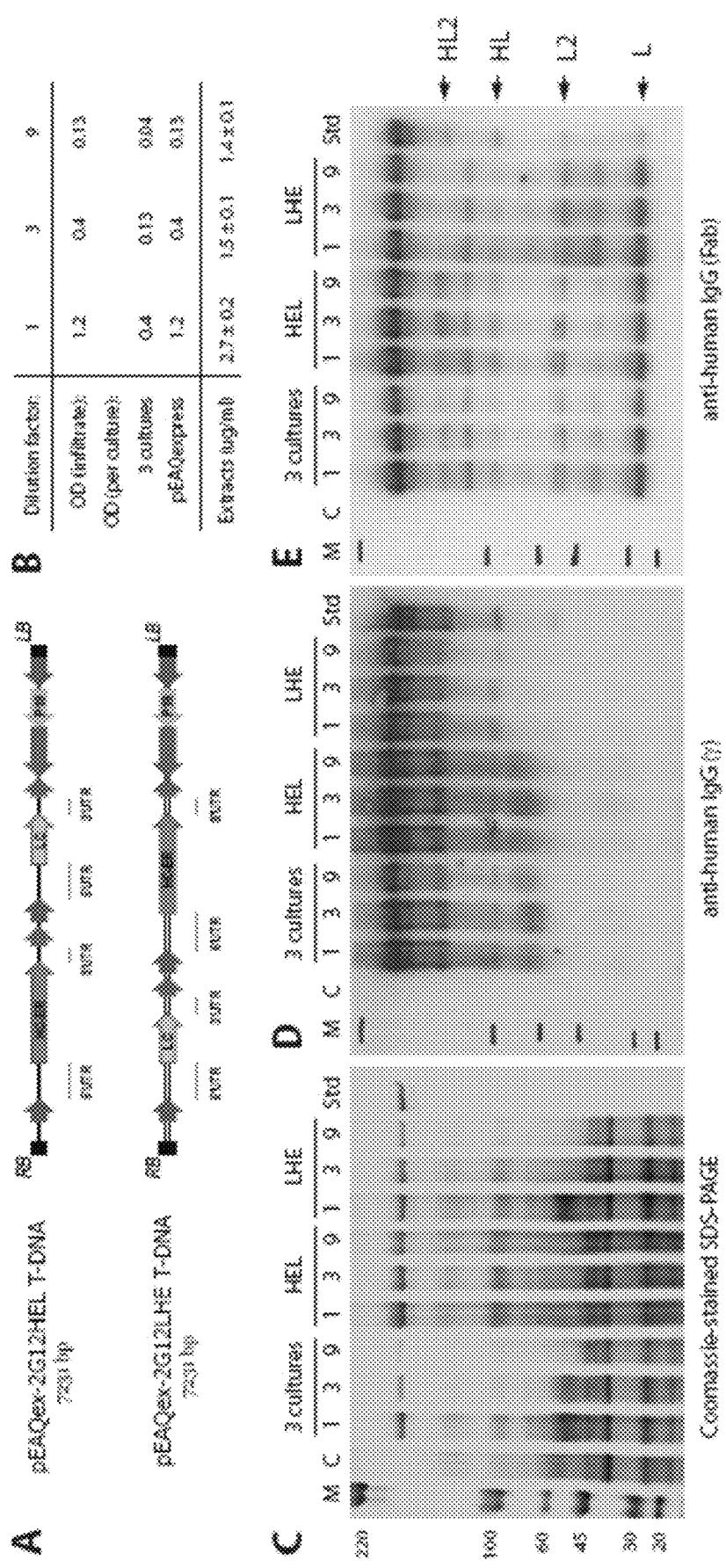
FIG. 13 shows expression of the full size IgG, 2G12, with a single pEAQ plasmid. (A Schematic representation of the two pEAQexpress-derived plasmids constructed to express 2G12. (B) Infiltration scheme indicating dilutions and their respective ODs for each plasmid combination, and the concentration of protein extracts made after infiltrations at each OD (SD). (C) Coomassie-stained 12-4% SDS-PAGE analysis and (D) immunological detection of 2G12 heavy (y) and (E) immunological detection of 2G12 Fab region (Fab) chain 8 days after infiltration. M, marker with sizes indicated; C, control extract; Std, CHO-produced 2G12. For coomassie-staining, protein from the equivalent of 3 mg of infiltrated tissue is loaded in each lane with 1 µg of CHO2G12 and for western blotting the equivalent of 0.75 mg of tissue in each lane with 250 ng of CHO2G12. Estimated assembly/degradation products are indicated.

In order to take advantage of the modular nature of the pEAQ series, CPMV-HT expression cassettes containing the ER-retained heavy chain (HE) and light chain (L) of the human anti-HIV IgG, 2G12 were inserted into the PacI/AscI and AsiSI/MluI sites of pEAQexpress. To determine whether the site of insertion influences expression levels, the L and HE chains were inserted into both positions yielding pEAQex-2G12HEL and pEAQex-2G12LHE (FIG. 13A). Infiltration of N. benthamiana with single Agrobacterium cultures containing the above plasmids resulted in the formation of fully assembled 2G12 antibodies identical in size to 2G12 produced by mixing three Agrobacterium cultures which each expressed the individual components, L, HE and P19 (FIG. 13C). The protein loaded in each lane represents 1/30 of the extract obtained from 90 mg of infiltrated tissue or 1/333 of the protein potentially obtainable from 1 g of tissue. The maximum amount of assembled IgG produced from the 3-strain mixture corresponds to 1 g of CHO-produced 2G12 on the coomassie-stained non-reduced SDS-PAGE gel. This suggests an expression level of 2G12 in excess of 325 mg/kg of fresh weight tissue, which is in agreement with the SPR-measured concentrations. The use of pEAQex-2G12HEL appears to surpass this already high-level of antibody accumulation.

An advantage of pEAQ-derived vectors is that each component of a multi-chain protein such as an IgG can automatically be delivered to each infected cell. Therefore, high expression levels should be maintained at higher dilutions of Agrobacteria suspensions than if multiple cultures have to be used. To test if this is the case in practice, cultures that were initially resuspended to OD 1.2, and mixed where necessary, were subjected to two serial three-fold dilutions (FIG. 13B). This resulted in final ODs of each individual culture in the three-culture mix being 0.4, 0.13, and 0.04. Single cultures harbouring the pEAQexpress constructs were infiltrated at ODs of 1.2, 0.4, and 0.13. When three separate cultures were used, the level of assembled 2G12 decreases markedly on serial dilution. In contrast, 2G12 expression from pEAQex-2G12HEL and pEAQex-2G12LHE, was maintained at a consistently high level, with any reduction on dilution being very modest (FIG. 13C-E). The lack of sensitivity to dilution confirms the improved efficiency afforded by placing all three expression cassettes on the same T-DNA. Interestingly, the amount of total protein extracted from the infiltrated tissue was almost halved when the OD of the infiltrate was reduced from 1.2 to 0.4. This suggests that a significant fraction of the protein in extracts from tissue in which the higher OD suspension has been infiltrated can consist of Agrobacteria-derived protein or plant proteins produced in response to the higher concentrations of *Agrobacteria*.

Inspection of FIG. 13C suggests that the relative position of a cassette within the T-DNA can affect the expression levels. The overall expression from pEAQex-2G12LHE was slightly lower than from pEAQex-2G12HEL. This was confirmed by western blotting of the non-reduced samples, which also indicated some differences in the abundance of degradation products and unincorporated immunoglobulin chains (FIG. 13C-E). Tissue infiltrated with pEAQex-2G12LHE appears to lack a heavy chain-specific degradation product of approximately 70 to 80 kDa (FIG. 13D). Also, there appears to be much less of the HL2 assembly intermediate, as well as more free light chain (FIG. 13E). Since, the heavy chain is known to be limiting in 2G12 assembly in plants (Markus Sack, pers. comm., RWTH, Aachen, Germany), which is confirmed by the lack of discernable free heavy chain in all samples, these results indicate that pEAQex-2G12LHE produces less heavy chain than pEAQex-2G12HEL. This could be due to reduced expression from the CPMV-HT cassette closer to the left border of the T-DNA.

In other experiments (data not shown) the CPMV-HT system has also been successfully used in the transient format in *N. benthamiana* to express:
 Bluetongue Virus (serotype 10) VP2, VP3, VP5, VP7 and NS1.
 Rotavirus NSP5.
 Calmodulin from *Medicago truncatula* (which was subsequently purified).
 The difficult-to-express ectodomain of human Fc gamma receptor 1 (CD64)—which has been purified and shown to be functional in antibody binding studies.
 The CPMV Small (S) and Large (L) coat proteins were co-expressed and shown to assemble into virus-like particles (data not shown)

Example 4

Direct Cloning into a CPMV-HT Expression Vector

Figure 14:
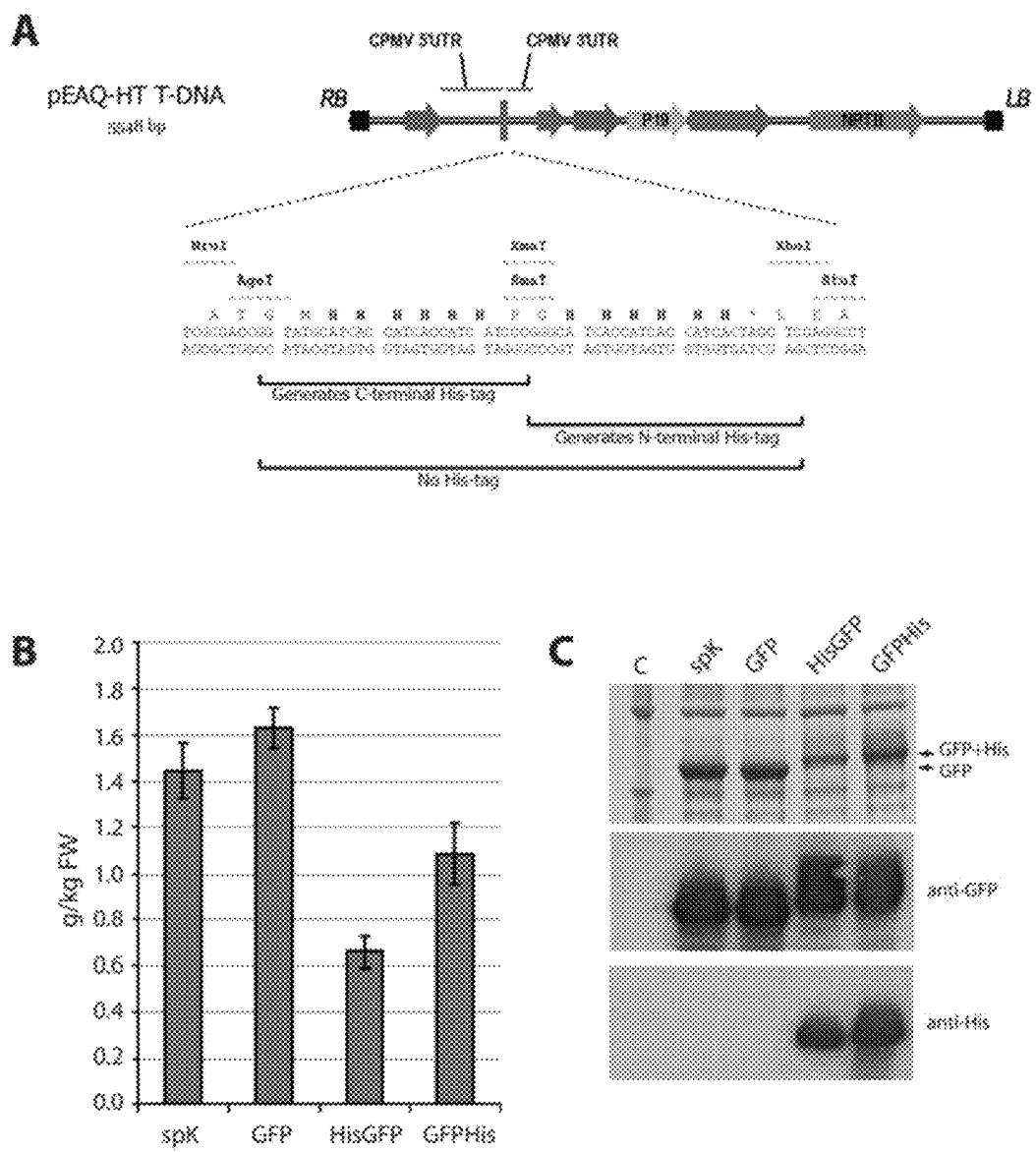
FIG. 14 shows the cloning and expression of GFP from pEAQ-HT in native and his-tagged variants. (A) Schematic representation of the pEAQ-HT T-DNA with polylinker detail. (B) Spectrofluorometric analysis of GFP expression. spK=pEAQspecialK-GFP-HT, GFP, HisGFP, and GFPHis=pEAQ-HT clones. (C) 12% SDS-PAGE and western analysis of GFP expression. C=control extract.

Although combining elements of the system on to a single plasmid, the vectors described hereinbefore still required a two-step cloning procedure to introduce a sequence to be expressed into the binary plasmid. The present example provides a binary plasmid into which a gene of interest could be directly inserted. The plasmid incorporates a polylinker that not only permits direct insertion into the pEAQ-based plasmid, but also permits the fusion of a C- or N-terminal histidine tag if desired (pEAQ-HT; FIG. 14A). The polylinker was first inserted as annealed oligonucleotides into pM81-FSC2-512(A115G)(U162C) giving pM81-FSC-POW. This construct can still be used for the standard two-step cloning procedure for the generation pEAQ-based constructs for the expression of multiple polypeptides. Furthermore, use of the double mutated 5' leader may enable even higher expression levels to be obtained than is possible with the single mutation. The CPMV-HT cassette was then transferred into pEAQspecialK via the PacI/AscI sites to give pEAQ-HT. Insertion of GFP into all three positions within the polylinker of pEAQ-HT resulted in an un-tagged GFP, and 5' (HisGFP) and 3' (GFPHis) His-tag fusions.

As expected, untagged GFP was expressed to a level even higher than that obtained with pEAQspecialK-GFP-HT and in excess of 1.6 g/kg FW tissue (FIG. 14B). This is likely due to the fact that the CPMV 5' leader of pEAQ-HT contains the extra mutation which removes AUG 115 which, when removed in addition to AUG 161, further enhances expression.

The presence of the His-tag as detected by western blotting confirmed the correct fusion at both the N- and C-terminus of the amino acid residues encoded by the polylinker. All three GFP variants were detectable with anti-GFP antibodies whereas only HisGFP and GFPHis were detectable with anti-His antibodies (FIG. 14C), and the presence of the His-tag reduced the mobility of the GFP band in SDS-PAGE by the expected amount. The tag also reduced the amount of GFP detected by the analysis of fluorescence (FIG. 14B). This effect was more pronounced for N-terminal His tag. The intensity of the coomassie-stained bands suggests that this represents a reduction in tagged GFP accumulation (FIG. 14C), rather than interference with the fluorogenic properties of GFP. Nevertheless, the levels of the His-tagged proteins were still very high yielding in excess of 0.6 and 1.0 g of GFP per kg FW tissue.

Discussion of Examples 2-4

To improve the ease of use and performance of the CPMV-HT expression system, a modular set of vectors has been created for easy and quick plant expression.

Removing more than half of the plasmid backbone from the binary vector, pBINPLUS, and some of the T-DNA region not essential for transient expression resulted in one of the smallest binary Ti plasmids known with no compromise on expression levels.

A similar proportion of the backbone had previously been removed from pBIN19 without a loss of performance (Xiang et al., 1999). However, pBINPLUS possesses two significant improvements over pBIN19 (van Engelen et al., 1995); an increased copy number in *E. coli* owing to the addition of the ColE1 origin of replication and a reoriented T-DNA ensuring the gene of interest is further from the left border that can suffer extensive deletions in planta (Rossi et al., 1996). While the smaller size of pEAQ plasmids had no noticeable effect on their copy number, they give greatly improved yields during cloning procedures using commercial plasmids extraction kits as these are most efficient for plasmids below 10 kb (data not shown).

The modular nature of the pEAQ binary vector adds functionality to CPMV-HT expression by allowing any silencing suppressor and/or marker gene, if required, to be co-expressed with one or two CPMV-HT cassettes. For example, insertion of a second HT cassette containing a heterologous sequence into the AsiSI/MluI sites of pEAQ-express-GFP-HT would allow tracking of expression with GFP fluorescence.

Furthermore, the flexibility of the vectors simplifies the system for transient expression by only requiring the infiltration of a single *Agrobacterium* construct, and improves efficiency by reducing the amount of infiltrate required in proportion to the number of expression cassettes present within the T-DNA. With P19 occupying the FseI site, the presence of two cloning sites for accepting HT cassettes from cloning vectors (such as pM81-FSC2-U162C) also allows even more efficient expression of multi-subunit proteins such as full-size antibodies.

The effect of P19 on enhancing expression levels of transgenes is well characterised (Voinnet et al., 2003). However, this study presents the first demonstration of its effectiveness when co-delivered to each cell on the same TDNA. A previous study has reported the co-delivery of P19 from a separate TDNA within the same *Agrobacterium* as the transgene-containing T-DNA (Hellens et al., 2005). However, there was no effect of P19 until 6 days after infiltration, suggesting inefficient transfer of T-DNA. The present study also demonstrates the first use of the R43W mutant P19 to enhance the expression of a transgene. The finding that the mutant was about half as effective in enhancing the expression of GFP as wt P19 agrees with its known reduction in activity, which compromises both the infectivity of TBSV (Chu et al., 2000), and the ability of the protein to bind the smaller class (21-22 nts) of short interfering RNAs (Omarov et al., 2006). However, it is possible that this feature potentially makes the R43W mutant more suitable for applications involving stable transformation. The micro RNAs associated with development are also in the smaller size class (Vaucheret, 2006; Zhang et al., 2006) and, therefore, developmental processes may not be as severely affected by the presence of the mutant P19 as they would by the wt version (Scholthof, 2007). Furthermore, the mutant may provide a way of controlling the transient expression of potentially cytotoxic foreign proteins.

The expression of 2G12 from a single plasmid represents the highest reported yield of an antibody from plant tissue infiltrated with a single Agrobacterium culture. Apart from using 3 Agrobacterium cultures for CPMV-HT expression, the only way of achieving similar levels with another system involved the infiltration of 6 separate cultures and a virus vector approach (Giritch et al., 2006). Furthermore, the use of a single plasmid affords a reduction in the amount of bacteria needed to ensure co-delivery of multiple expression cassettes, which would provide a significant cost saving at industrial production levels. The infiltration process is also physically easier to carry out with more dilute cultures due to less clogging of the intercellular spaces of leaf tissue. In addition, the dilution to a total OD of 0.4 reduced the amount of infiltration-derived protein contaminants. Analysis of nine separate infiltrations at each OD showed a reduction in the protein concentrations of the extracts from 2.7±0.2 to 1.5±0.1 mg/ml when the OD of the cultures was reduced from 1.2 to 0.4. Since the use of pEAQexpress generates as much 2G12 at OD 0.4 as the three-culture system does at an infiltrate OD of 1.2, the recombinant target protein must be purified from only half the amount of contaminating protein using pEAQexpress. This provides a very useful and unexpected advantage for downstream processing. Expression of 2G12 from pEAQexpress also indicates an effect of position of an expression cassette within the T-DNA of pEAQ vectors on the level of expression obtained. The increase in free light chain accumulation from pEAQex-2G12LHE suggests that less heavy chain is expressed with this construct, which appears to result in less assembled antibody. This could be due to the arrangement of expression cassettes on the T-DNA. Alternatively, a proportion of the T-DNAs are susceptible to nucleolytic degradation at the left border (Rossi et al., 1996). The reinsertion of the NPTII cassette within the T-DNA appeared to have a marked effect on expression depending on its orientation. During cloning manipulations it became apparent that pEAQselectK-GFP-HT reached a plasmid copy number in E. coli of approximately 1.5 times that of pEAQselectK(rev)-GFP-HT (determined from yield measurements of three separate plasmid preparations performed with the QIAprep kit, QIAGEN). This loosely correlates to the difference in expression levels observed between the two vectors. It is not known what contributes to the increased copy number, or indeed whether the difference also exists when the plasmids are transferred to Agrobacteria. However, these observations suggest that plasmid copy number may be an important for efficient Agrobacterium mediated transient expression. In this respect, the use of the RK2 origin (oriV in FIG. 9) by pBIN19 and its derivatives makes it a good choice for transient expression as RK2 plasmids are known to accumulate to 7 to 10 copies in Agrobacterium (Veluthambi et al., 1987). This is similar to the pVS1 origin utilised by pPZP and about 2-5 times higher than is generated by the pSa origin (Lee and Gelvin, 2008), which is present in the widely used pGREEN binary vector (Helens et al., 2000). Plasmids containing replication origins that yield higher copy numbers such as pRi-based plasmids (Lee and Gelvin, 2008) may be even better suited to transient expression.

To make high-level expression with pEAQ vectors easily accessible for labs with no previous experience with CPMV-based expression or indeed, plant-based expression in general, a direct cloning version of pEAQ was created. This was achieved by inserting a polylinker between the 5' leader and 3' UTRs of a CPMVHT expression cassette, which was the positioned on a T-DNA which also contained P19 and NPTII cassettes. The NPTII cassette was included because its presence appeared to appreciably enhance expression (see above). The polylinker also encodes two sets of 6× Histidine residues to allow the fusion of N- or C terminal His-tags to facilitate protein purification. The resulting constructs also benefit from the second mutation in the 5' leader which enhances expression relative to HT.

These enhanced expression cassettes may also be subcloned from the cloning vector pM81-FSC-POW into any pEAQ plasmid. The use of pEAQHT led to increased GFP expression compared with pEAQspecialK, which contains just the single mutation (U162C). Furthermore, the polylinker design also allowed the expression of His-tagged variants using a one step cloning procedure. The modular binary vectors presented here are specifically designed for, but not restricted to, use with CPMV-HT expression. Extremely high-level expression has been coupled with improved cloning efficiency and ease of use. The system provides the most effective and straightforward method for transient expression of value-added proteins in plants without the complications of viral amplification. It allows milligram quantities of recombinant protein within two weeks of sequence identification in any molecular biology lab with access to plant growth facilities. Therefore, it is anticipated that it will provide an extremely valuable tool in both academic and industrial settings.

Example 5

Stable Integration with pEAQ Plasmids and Transgenic Plants

Although the pEAQ vector series was designed with transient expression in mind, the reinsertion of the NPTII cassette into the T-DNA to provides a selectable marker for genome integration. This potentially allows these smaller and more useful binary vectors to be used for stable plant and plant cell culture transformation. When used to transform N. benthamiana leaf discs, pEAQ vectors containing the NPTII cassette within the T-DNA were able to induce callus formation under selection with the same efficiency as pBINPLUS-based constructs. Furthermore, GFP expression was detectable in these tissues under UV light (data not shown). This demonstrates that multi-cassette T-DNA molecules from pEAQ vectors can stably integrate into the plant genome and drive the expression of foreign genes.

Fluorescent plants have also been regenerated. The leaves of the primary transformants (T0) were fluorescent under uv light indicating high levels of GFP expression. The seed

Example 6

Use of the CPMV-Based HT System with Baculovirus Vectors

Figure 15:
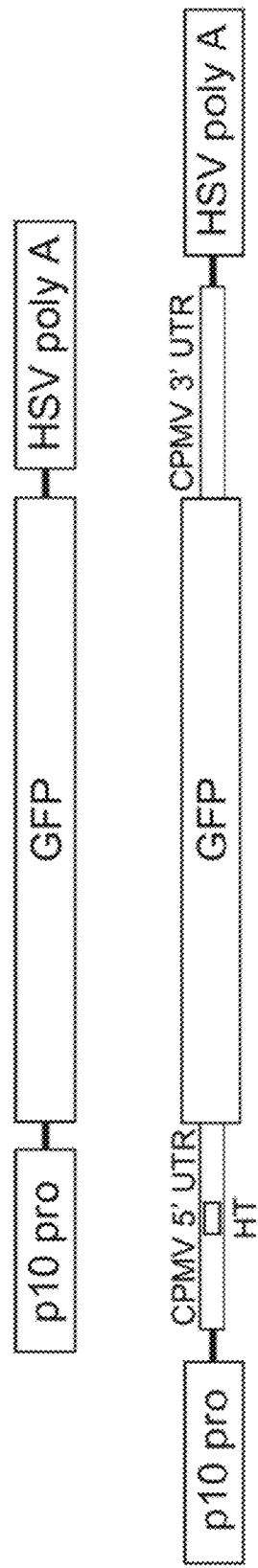
FIG. 15 shows a nucleic construct of the present invention which is suitable for use in insect cells as part of a baculovirus vector.

FIG. 15 shows a construct suitable for utilising the CPMV-based HT system with baculovirus vectors in insect cells. Under control of the p10 promoter, the HyperTrans CPMV RNA-2 UTRs also enhance the expression of GFP in insect cells using the Baculovirus expression system. An approximately 5-fold enhancement of fluorescence levels in baculovirus-infected sf21 cells, as measured by flow cytometry, was obtained in comparison to a construct without the CPMV-HT cassette.

REFERENCES

Alamillo, J. M., Monger, W., Sola, I., Garcia, B., Perrin, Y., Bestagno, M., Burrone, O. R., Plana-Duran, J., Enjuanes, L., Lomonossoff, P. G. and Garcia, J. A. (2006) Use of virus vectors for the expression in plants of active full-length and single chain anticoronavirus antibodies. *Biotechnol. J.* 1, 1103-1111.

Brigneti, G., Voinnet, O., Li, W. X., Ji, L. H., Ding, S. W and Baulcombe, D. C. (1998) Viral pathogenicity determinants are suppressors of transgene silencing in *Nicotiana benthamiana*. *EMBO Journal* 17: 6739-6746.

Cañizares, M. C., Liu, L., Perrin, Y., Tsakiris, E. and Lomonossoff, G. P. (2006). A bipartite system for the constitutive and inducible expression of high levels of foreign proteins in plants. *Plant Biotechnol. J.* 4, 183-193.

Gopinath, K., Wellink, J., Porta, C., Taylor, K. M., Lomonossoff, G. P. and van Kammen, A. (2000) Engineering cowpea mosaic virus RNA-2 into a vector to express heterologous proteins in plants. Virology 267: 159-173.

Holness, C. L., Lomonossoff, G. P., Evans, D. and Maule, A. J. (1989). Identification of the initiation codons for translation of cowpea mosaic virus middle component RNA using site directed mutagenesis of an infectious cDNA clone. Virology 172, 311320.

Liu, L. and Lomonossoff, G. P. (2002) Agroinfection as a rapid method for propagating Cowpea mosaic virus-based constructs. *J. Virol. Methods* 105, 343-348.

Liu, L. and Lomonossoff, G. P. (2006) A site-directed mutagenesis method utilising large double-stranded DNA templates for the simultaneous introduction of multiple changes and sequential multiple rounds of mutation: Application to the study of whole viral genomes. *J. Virol. Methods* 137, 63-71.

Liu, L., Canizares, M. C., Monger, W., Perrin, Y., Tsakiris, E., Porta, C., Shariat, N., Nicholson, L. and Lomonossoff, G. P. (2005). Cowpea mosaic virus-based systems for the production of antigens and antibodies in plants. *Vaccine* 23, 1788-1792.

Lomonossoff, G. P. & Shanks, M. (1983). The nucleotide sequence of cowpea mosaic virus B RNA. *EMBO Journal* 2, 2253-2258.

Mechtcheriakova, I. A., Eldarov, M. A., Nicholson, L., Shanks, M., Skryabin, K. G. and Lomonossoff, G. P. (2006) The use of viral vectors to produce hepatitis B virus core particles in plants. *J. Virol. Methods* 131, 10-15.

Monger, W., Alamillo, J. M., Sola, I., Perrin, Y., Bestagno, M., Burrone, O R., Sabella, P., Plana-Duran, J., Enjuanes, L., Garcia, J. A. and Lomonossoff, G. P. (2006) An antibody derivative expressed from viral vectors passively immunizes pigs against transmissible gastroenteritis virus infection when supplied orally in crude plant extracts. *Plant Biotechnol. J.* 4, 623-631.

Rohll, J. B., Holness, C. L., Lomonossoff, G. P. and Maule, A. J. (1993). 3' terminal nucleotide sequences important for the accumulation of cowpea mosaic virus M-RNA. Virology 193, 672-679.

Sainsbury, F., Lavoie, P-O., D'Aoust, M-A., Vezina, L-P. and Lomonossoff, G. P. (2008). Expression of Multiple Proteins Using Full-Length and Deleted Versions of Cowpea Mosaic Virus RNA-2. *Plant Biotechnology Journal*, 6: 82-92.

Sainsbury, F., Cañizares, M. C. and Lomonossoff, G. P. (2007) Cowpea mosaic virus-based expression vectors. In: *Virus Expression Vectors* (Hefferon, K. ed), pp. 339-555. Kerala, India: Transworld Research Network.

Sainsbury, F. and Lomonossoff, G. P. (2008). Extremely high-level and rapid transient protein production in plants without the use of viral replication. *Plant Physiology* 148, 1212-1218.

Sainsbury, F., Liu, L. and Lomonossoff G. P. (2009) Cowpea mosaic virus-based expression of antigens and antibodies in plants. In: *Methods in Molecular Biology* Vol. 483: *Recombinant Pharmaceutical Proteins from Plants* (Faye, L. and Gomord, V. eds), pp 25-39, NY: Humana Press.

van Bokhoven, H., Le Gall, O, Kasteel, D., Verver, J., Wellink, J. and van Kammen, A. (1993). Cis- and Trans-acting Elements in Cowpea Mosaic Virus RNA Replication. Virology 195, 377-386.

Wellink J, Verver J, van Kammen A. (1993). Mutational analysis of AUG codons of cowpea mosaic virus M RNA. Biochimie. 75(8):741-7.

ADDITIONAL REFERENCES

Lee L Y, Gelvin S B (2008) T-DNA binary vectors and systems. Plant Physiology 146: 325-332

Hajdukiewicz P, Svab Z, Maliga P (1994) The small, versatile pPZP family of *Agrobacterium* binary vectors for plant transformation. Plant Molecular Biology 25: 989-994

Hellens R, Mullineaux P, Klee H (2000b) A guide to *Agrobacterium* binary Ti vectors. Trends in Plant Science 5: 446-451

Hiei Y, Ohta S, Komari T, Kumashiro T (1994) Efficient transformation of rice (*Oryza-sativa* L) mediated by *Agrobacterium* and sequence-analysis of the boundaries of the T-DNA. Plant Journal 6: 271-282

Veluthambi K, Jayaswal R K, Gelvin S B (1987) Virulence genes-a, gene-G, and gene-D mediate the double-stranded border cleavage of T-DNA from the *Agrobacterium* Ti plasmid. Proceedings of the National Academy of Sciences of the United States of America 84: 1881-1885

Thole V, Worland B, Snape J W, Vain P (2007) The pCLEAN dual binary vector system for *Agrobacterium*-Mediated plant transformation. Plant Physiology 145: 1211-1219

Johansen L K, Carrington J C (2001) Silencing on the spot. Induction and suppression of RNA silencing in the *Agrobacterium*-mediated transient expression system. Plant Physiology 126: 930-938

Janssen B J, Gardner R C (1989) Localized transient expression of Gus in leaf-disks following cocultivation with *Agrobacterium*. Plant Molecular Biology 14: 61-72

Narasimhulu S B, Deng X, Sarria R, Gelvin S B (1996) Early transcription of *Agrobacterium* T-DNA genes in tobacco and maize. Plant Cell 8: 873-886

Hellens R P, Edwards E A, Leyland N R, Bean S, Mullineaux P M (2000a) pGreen: a versatile and flexible binary Ti vector for *Agrobacterium*-mediated plant transformation. Plant Molecular Biology 42: 819-832

Tzfira T, Tian G W, Lacroix B, Vyas S, Li J X, Leitner-Dagan Y, Krichevsky A, Taylor T, Vainstein A, Citovsky V (2005) pSAT vectors: a modular series of plasmids for autofluorescent protein tagging and expression of multiple genes in plants. Plant Molecular Biology 57: 503-516

Voinnet O, Rivas S, Mestre P, Baulcombe D (2003) An enhanced transient expression system in plants based on suppression of gene silencing by the p19 protein of tomato bushy stunt virus. Plant Journal 33: 949-956

Frisch D A, Harrishaller L W, Yokubaitis N T, Thomas T L, Hardin S H, Hall T C (1995) Complete sequence of the binary vector BIN-19. Plant Molecular Biology 27: 405-409

Trieu-cuot P, Courvalin P (1983) Nucleotide-sequence of the *Streptococcus-faecalis* plasmid gene encoding the 3'5"-Aminoglycoside phosphotransferase type-III. Gene 23: 331-341

Bevan M (1984) Binary *Agrobacterium* vectors for plant transformation. Nucleic Acids Research 12: 8711-8721

Silhavy D, Burgyan J (2004) Effects and side-effects of viral RNA silencing suppressors on short RNAs. Trends in Plant Science 9: 76-83

Scholthof H B (2007) Heterologous expression of viral RNA interference suppressors: RISC management. Plant Physiology 145: 1110-1117 van Engelen F A, Molthoff J W, Conner A J, Nap J P, Pereira A, Stiekema W J (1995) pBINPLUS—an improved plant transformation vector based on pBIN19. Transgenic Research 4: 288-290

Rossi L, Hohn B, Tinland B (1996) Integration of complete transferred DNA units is dependent on the activity of virulence E2 protein of *Agrobacterium tumefaciens*. Proceedings of the National Academy of Sciences of the United States of America 93: 126-130

Xiang C B, Han P, Lutziger I, Wang K, Oliver D J (1999) A mini binary vector series for plant transformation. Plant Molecular Biology 40: 711-717

Hellens R P, Allan A C, Friel E N, Bolitho K, Grafton K, Templeton M D, Karunairetnam S, Gleave A P, Laing W A (2005) Transient expression vectors for functional genomics, quantification of promoter activity and RNA silencing in plants. Plant Methods 1: 13

Chu M, Desvoyes B, Turina M, Noad R, Scholthof H B (2000) Genetic dissection of tomato bushy stunt virus p19-protein-mediated host-dependent symptom induction and systemic invasion. Virology 266: 79-87

Omarov R, Sparks K, Smith L, Zindovic J, Scholthof H B (2006) Biological relevance of a stable biochemical interaction between the tombusvirus-encoded P19 and short interfering RNAs. Journal of Virology 80: 3000-3008

Vaucheret H (2006) Post-transcriptional small RNA pathways in plants: mechanisms and regulations. Genes & Development 20: 759-771

Zhang B H, Pan X P, Cobb G P, Anderson T A (2006) Plant microRNA: A small regulatory molecule with big impact. Developmental Biology 289: 3-16

Giritch A, Marillonnet S, Engler C, van Eldik G, Botterman J, Klimyuk V, Gleba Y (2006) Rapid high-yield expression of full-size IgG antibodies in plants coinfected with noncompeting viral vectors. Proceedings of the National Academy of Sciences of the United States of America 103: 14701-14706

TABLE 2

SEQ ID NO: 1
The complete CPMV RNA-2 genome segment
(nucleotides 1 to 3481)

```
  1    tattaaaatc ttaataggtt ttgataaaag cgaacgtggg gaaacccgaa ccaaaccttc 61    ttctaaattc tctctcatct ctcttaaagc aaacttctct cttgtctttc ttgcatgagc 121    gatcttcaac gttgtcagat cgtgcttcgg caccagtaca atgttttctt tcactgaagc 181    gaaatcaaag atctctttgt ggacacgtag tgcggcgcca ttaaataacg tgtacttgtc 241    ctattcttgt cggtgtggtc ttgggaaaag aaagcttgct ggaggctgct gttcagcccc 301    atacattact tgttacgatt ctgctgactt tcggcgggtg caatatctct acttctgctt 361    gacgaggtat tgttgcctgt acttctttct tcttcttctt gctgattggt tctataagaa 421    atctagtatt ttctttgaaa cagagttttc ccgtggtttt cgaacttgga gaaagattgt 481    taagcttctg tatattctgc ccaaatttga aatggaaagc attatgagcc gtggtattcc 541    ttcaggaatt ttggaggaaa aagctattca gttcaaacgt gccaaagaag ggaataaacc 601    cttgaaggat gagattccca agcctgagga tatgtatgtg tctcacactt ctaaatggaa 661    tgtgctcaga aaaatgagcc aaaagactgt ggatctttcc aaagcagctg ctgggatggg 721    attcatcaat aagcatatgc ttacgggcaa catcttggca caaccaacaa cagtcttgga 781    tattcccgtc acaaaggata aaacacttgc gatggccagt gattttattc gtaaggagaa 841    tctcaagact tctgccattc acattggagc aattgagatt attatccaga gctttgcttc 901    ccctgaaagt gatttgatgg gaggcttttt gcttgtggat tctttacaca ctgatacagc 961    taatgctatt cgtagcattt ttgttgctcc aatgcgggga ggaagaccag tcagagtggt
```

TABLE 2-continued

SEQ ID NO: 1
The complete CPMV RNA-2 genome segment
(nucleotides 1 to 3481)

```
1021  gaccttccca aatacactgg cacctgtatc atgtgatctg aacaatagat tcaagctcat
1081  ttgctcattg ccaaactgtg atattgtcca gggtagccaa gtagcagaag tgagtgtaaa
1141  tgttgcagga tgtgctactt ccatagagaa atctcacacc ccttcccaat tgtatacaga
1201  ggaatttgaa aaggagggtg ctgttgttgt agaatactta ggcagacaga cctattgtgc
1261  tcagcctagc aatttaccca cagaagaaaa acttcggtcc cttaagtttg actttcatgt
1321  tgaacaacca agtgtcctga agttatccaa ttcctgcaat gcgcactttg tcaagggaga
1381  aagtttgaaa tactctattt ctggcaaaga agcagaaaac catgcagttc atgctactgt
1441  ggtctctcga aaggggctt ctgcggcacc caagcaatat gatcctattt tgggacgggt
1501  gctggatcca cgaaatggga atgtggcttt ccacaaatg gagcaaaact tgtttgccct
1561  ttctttggat gatacaagct cagttcgtgg ttctttgctt gacacaaaat tcgcacaaac
1621  tcgagttttg ttgtccaagg ctatggctgg tggtgatgtg ttattggatg agtatctcta
1681  tgatgtggtc aatggacaag attttagagc tactgtcgct tttttgcgca cccatgttat
1741  aacaggcaaa ataaaggtga cagctaccac caacatttct gacaactcgg gttgttgttt
1801  gatgttggcc ataaatagtg gtgtgagggg taagtatagt actgatgttt atactatctg
1861  ctctcaagac tccatgacgt ggaacccagg gtgcaaaaag aacttctcgt tcacatttaa
1921  tccaaaccct tgtggggatt cttggtctgc tgagatgata agtcgaagca gagttaggat
1981  gacagttatt tgtgtttcgg gatggacctt atctcctacc acagatgtga ttgccaagct
2041  agactggtca attgtcaatg agaaatgtga gcccaccatt taccacttgg ctgattgtca
2101  gaattggtta ccccttaatc gttggatggg aaaattgact tttccccagg gtgtgacaag
2161  tgaggttcga aggatgcctc tttctatagg aggcggtgct ggtgcgactc aagctttctt
2221  ggccaatatg cccaattcat ggatatcaat gtggagatat tttagaggtg aacttcactt
2281  tgaagttact aaaatgagct ctccatatat taaagccact gttacatttc tcatagcttt
2341  tggtaatctt agtgatgcct ttggttttta tgagagtttt cctcatagaa ttgttcaatt
2401  tgctgaggtt gaggaaaaat gtactttggt tttctcccaa caagagtttg tcactgcttg
2461  gtcaacacaa gtaaacccca gaaccacact tgaagcagat ggttgtccct acctatatgc
2521  aattattcat gatagtacaa caggtacaat ctccggagat tttaatcttg gggtcaagct
2581  tgttggcatt aaggattttt gtggtatagg ttctaatccg ggtattgatg gttcccgctt
2641  gcttggagct atagcacaag gacctgtttg tgctgaagcc tcagatgtgt atagcccatg
2701  tatgatagct agcactcctc ctgctccatt ttcagacgtt acagcagtaa cttttgactt
2761  aatcaacggc aaaataactc ctgttggtga tgacaattgg aatacgcaca tttataatcc
2821  tccaattatg aatgtcttgc gtactgctgc ttggaaatct ggaactattc atgttcaact
2881  taatgttagg ggtgctggtg tcaaaagagc agattgggat ggtcaagtct ttgtttacct
2941  gcgccagtcc atgaaccctg aaagttatga tgcgcggaca tttgtgatct cacaacctgg
3001  ttctgccatg ttgaacttct cttttgatat catagggccg aatagcggat ttgaatttgc
3061  cgaaagccca tgggccaatc agaccacctg gtatcttgaa tgtgttgcta ccaatcccag
3121  acaaatacag caatttgagg tcaacatgcg cttcgatcct aatttcaggg ttgccggcaa
3181  tatcctgatg cccccatttc cactgtcaac ggaaactcca ccgttattaa agtttaggtt
3241  tcgggatatt gaacgctcca agcgtagtgt tatggttgga cacactgcta ctgctgctta
```

TABLE 2-continued

SEQ ID NO: 1
The complete CPMV RNA-2 genome segment
(nucleotides 1 to 3481)

```
3301    actctggttt cattaaattt tctttagttt gaatttactg ttatttggtg tgcatttcta 3361    tgtttggtga gcggttttct gtgctcagag tgtgtttatt ttatgtaatt taatttcttt 3421    gtgagctcct gtttagcagg tcgtcccttc agcaaggaca caaaaagatt ttaattttat 3481    t
```

The start codons at positions 115, 161, 512 and 524 of the CPMV RNA-2 genome segment are shown in bold and underlined.

TABLE 3

Oligonucleotides used in the mutagenesis of the 5' region of pM81-FSC-2 clones

| SEQ ID NO: | Oligo-nucleotide | Sequence | Mutation |
|---|---|---|---|
| 2 | A115G-F | CTTGTCTTTCTT GCGTGAGCGATC TTCAACG | Removes AUG (→GUG) at 115 eliminating translation from uORF |
| 3 | A115G-R | CGTTGAAGATCG CTCACGCAAGAA AGACAAG | |
| 4 | U162C-F | GGCACCAGTACA ACGTTTTCTTTC ACTGAAGCG | Removes AUG (→ACG) at 161 eliminating translation from AUG 161 while maintaining amino acid sequence of uORF |
| 5 | U162C-R | CGCTTCAGTGAA AGAAAACGTTGT ACTGGTGCC | |

The mutant nucleotide of the oligonucleotides used in the mutagenesis of the 5' region of pM81-FSC-2 clones are shown in bold

TABLE 4

| SEQ ID NO: 6 | CPMV wt sequence from Table 1 | tatattctgc ccaaatttga aatggaaagc attatgagcc gtggtattcc |
| SEQ ID NO: 7 | Mutated sequence in pM81-FSC-1 | tatattctgc ccaaatttgT CatgAaaagc attatgagcc gtggtattcc 509 BspH1 |
| SEQ ID NO: 8 | Mutated sequence in pM81-FSC-2 | tatattctgc ccaaattCGC GACGATCGTA CTCTCGAGGC CT 507 Nru1 Xho1 |

Nucleotide differences between the sequence of the pM81-FSC-1 and pM81-FSC-2 vectors and the CPMV wt sequence from Table 2 are shown as capital letters.

Nucleotide Sequence of pM81-FSC-1

SEQ ID NO: 9

```
LOCUS       pM81-FSC1  7732 bp DNA circular
            10 Oct. 2007

FEATURES              Location/Qualifiers
     5'UTR            342..501
                      /vntifkey = "52"
                      /label = CPMV\RNA2\5'UTR
     promoter         27..341
                      /vntifkey = "29"
                      /label = CaMV\35S\promoter
     terminator       4669..4921
                      /vntifkey = "43"
                      /label = Nos\Terminator
     mat_peptide      3712..4422
                      /vntifkey = "84"
                      /label = GFP
     3'UTR            4432..4615
                      /vntifkey = "50"
                      /label = CPMV\RNA2\3'UTR
     CDS              complement(5944..6804)
                      /vntifkey = "4"
                      /label = AmpR
     misc_feature     complement(7391..7546)
                      /vntifkey = "21"
                      /label = lacZ_a
     promoter         complement(6846..6874)
                      /vntifkey = "30"
                      /label = AmpR\promoter
```

-continued

| Nucleotide Sequence of pM81-FSC-1 |
|---|

```
          rep_origin         complement(7067..7373)
                             /vntifkey = "33"
                             /label = f1_origin
          rep_origin         complement(5170..5789)
                             /vntifkey = "33"
                             /label = pBR322_origin
          mat_peptide        502..1878
                             /vntifkey = "84"
                             /label = CPMV\Movement\Protein
          mat_peptide        1879..2999
                             /vntifkey = "84"
                             /label = CPMV\Lg.\Coat\Protein
          mat_peptide        3000..3638
                             /vntifkey = "84"
                             /label = CPMV\Sm.\Coat\Protein BASE COUNT  2105 a 1682 c 1770 g 2175 t ORIGIN
   1      ttaattaaga attcgagctc caccgcggaa acctcctcgg attccattgc ccagctatct 61      gtcactttat tgagaagata gtggaaaagg aaggtggctc ctacaaatgc catcattgcg 121      ataaaggaaa ggccatcgtt gaagatgcct ctgccgacag tggtcccaaa gatggacccc 181      cacccacgag gagcatcgtg gaaaaagaag acgttccaac cacgtcttca aagcaagtgg 241      attgatgtga tatctccact gacgtaaggg atgacgcaca atcccactat ccttcgcaag 301      acccttcctc tatataagga agttcatttc atttggagag gtattaaaat cttaataggt 361      tttgataaaa gcgaacgtgg ggaaacccga accaaacctt cttctaaact ctctctcatc 421      tctcttaaag caaacttctc tcttgtcttt cttgcatgag cgatcttcaa cgttgtcaga 481      tcgtgcttcg gcaccagtac aatgttttct ttcactgaag cgaaatcaaa gatctctttg 541      tggacacgta gtgcggcgcc attaaataac gtgtacttgt cctattcttg tcggtgtggt 601      cttgggaaaa gaaagcttgc tggaggctgc tgttcagccc catacattac ttgttacgat 661      tctgctgact ttcggcgggt gcaatatctc tacttctgct tgacgaggta ttgttgcctg 721      tacttctttc ttcttcttct tgctgattgg ttctataaga aatctagtat tttctttgaa 781      acagagtttt cccgtggttt tcgaacttgg agaaagattg ttaagcttct gtatattctg 841      cccaaatttg tcatgaaaag cattatgagc cgtggtattc cttcaggaat tttggaggaa 901      aaagctattc agttcaaacg tgccaaagaa gggaataaac ccttgaagga tgagattccc 961      aagcctgagg atatgtatgt gtctcacact tctaaatgga atgtgctcag aaaaatgagc 1021      caaaagactg tggatctttc caaagcagct gctgggatgg gattcatcaa taagcatatg 1081      cttacgggca acatcttggc acaaccaaca acagtcttgg atattcccgt cacaaaggat 1141      aaaacacttg cgatggccag tgattttatt cgtaaggaga atctcaagac ttctgccatt 1201      cacattggag caattgagat tattatccag agctttgctt cccctgaaag tgatttgatg 1261      ggaggctttt tgcttgtgga ttctttacac actgatacag ctaatgctat tcgtagcatt 1321      tttgttgctc caatgcgggg aggaagacca gtcagagtgg tgaccttccc aaatacactg 1381      gcacctgtat tatgtgatct gaacaataga ttcaagctca tttgctcatt gccaaactgt 1441      gatattgtcc agggtagcca agtagcagaa gtgagtgtaa atgttgcagg atgtgctact 1501      tccatagaga aatctcacac cccttcccaa ttgtatacag aggaatttga aaaggagggt 1561      gctgttgttg tagaatactt aggcagacag acctattgtg ctcagcctag caatttaccc 1621      acagaagaaa aacttcggtc ccttaagttt gactttcatg ttgaacaacc aagtgtcctg 1681      aagttatcca attcctgcaa tgcgcacttt gtcaagggaa aaagtttgaa atactctatt
```

-continued

| Nucleotide Sequence of pM81-FSC-1 |
|---|
| 1741 | tctggcaaag aagcagaaaa ccatgcagtt catgctactg tggtctctcg agaaggggct |
| 1801 | tctgcggcac ccaagcaata tgatcctatt tgggacggg tgctggatcc acgaaatggg |
| 1861 | aatgtggctt ttccacaaat ggagcaaaac ttgtttgccc tttctttgga tgatacaagc |
| 1921 | tcagttcgtg gttcttgct tgacacaaaa ttcgcacaaa ctcgagtttt gttgtccaag |
| 1981 | gctatggctg gtggtgatgt gttattggat gagtatctct atgatgtggt caatggacaa |
| 2041 | gattttagag ctactgtcgc ttttttgcgc acccatgtta acaggcaa aataaaggtg |
| 2101 | acagctacca ccaacatttc tgacaactcg ggttgttgtt tgatgttggc cataaatagt |
| 2161 | ggtgtgaggg gtaagtatag tactgatgtt tatactatct gctctcaaga ctccatgacg |
| 2221 | tggaacccag ggtgcaaaaa gaacttctcg ttcacattta atccaaaccc ttgtggggat |
| 2281 | tcttggtctg ctgagatgat aagtcgaagc agagttagga tgacagttat ttgtgtttcg |
| 2341 | ggatggacct tatctcctac cacagatgtg attgccaagc tagactggtc aattgtcaat |
| 2401 | gagaaatgtg agcccaccat ttaccacttg gctgattgtc agaattggtt accccttaat |
| 2461 | cgttggatgg gaaaattgac ttttccccag ggtgtgacaa gtgaggttcg aaggatgcct |
| 2521 | cttttctatag gaggcggtgc tggtgcgact caagcttct tggccaatat gcccaattca |
| 2581 | tggatatcaa tgtggagata ttttagaggt gaacttcact ttgaagttac taaaatgagc |
| 2641 | tctccatata ttaaagccac tgttacattt ctcatagctt ttggtaatct tagtgatgcc |
| 2701 | tttggttttt atgagagttt tcctcataga attgttcaat ttgctgaggt tgaggaaaaa |
| 2761 | tgtactttgg ttttctccca acaagagttt gtcactgctt ggtcaacaca agtaaacccc |
| 2821 | agaaccacac ttgaagcaga tggttgtccc tacctatatg caattattca tgatagtaca |
| 2881 | acaggtacaa tctccggaga ttttatcttg gggtcaagct tgttggcatt aaggattttt |
| 2941 | gtggtatagg ttctaatccg ggtattgatg gttccgctt gcttggagct atagcacaag |
| 3001 | gacctgtttg tgctgaagcc tcagatgtgt atagcccatg tatgatagc agcactcctc |
| 3061 | ctgctccatt ttcagacgtc acagcagtaa acttttgact taatcaacgg caaaataact |
| 3121 | cctgttggtg atgacaattg gaatacgcac atttataatc ctccaattat gaatgtcttg |
| 3181 | cgtactgctg cttggaaatc tggaactatt catgttcaac ttaatgttag gggtgctggt |
| 3241 | gtcaaaagag cagattggga tggtcaagtc tttgtttacc tgcgccagtc catgaaccct |
| 3301 | gaaagttatg atgcgcggac atttgtgatc tcacaacctg gttctgccat gttgaacttc |
| 3361 | tcttttgata tcatagggcc gaatagcgga tttgaatttg ccgaaagccc atgggccaat |
| 3421 | cagaccacct ggtatcttga atgtgttgct accaatccca gacaaataca gcaatttgag |
| 3481 | gtcaacatgc gcttcgatcc taatttcagg gttgccggca atatcctgat gcccccatttt |
| 3541 | ccactgtcaa cggaaactcc accgttatta agtttaggt ttcgggatat tgaacgctcc |
| 3601 | aagcgtagtg ttatggttgg acacactgct actgctgcag cgcctgcaaa acagctctta |
| 3661 | aactttgacc tacttaagtt agcaggtgac gttgagtcca accctgggcc cagtaaagga |
| 3721 | gaagaacttt tcactggagt tgtcccaatt cttgttgaat tagatggtga tgttaatggg |
| 3781 | cacaaatttt ctgtcagtgg agagggtgaa ggtgatgcaa catacggaaa acttaccctt |
| 3841 | aaatttattt gcactactgg aaaactacct gttccatggc caacacttgt cactactttc |
| 3901 | tcttatggtg ttcaatgctt ttcaagatac ccagatcata tgaaacggca tgactttttc |
| 3961 | aagagtgcca tgcccgaagg ttatgtacag gaaagaacta tattttcaa ggatgacggg |
| 4021 | aactacaaga cacgtgctga agtcaagttt gaaggtgata cccttgttaa tagaatcgag |

Nucleotide Sequence of pM81-FSC-1

```
4081  ttaaaaggta ttgattttaa agaagatgga acattcttg gacacaaatt ggaatacaac
4141  tataactcac acaatgtata catcatggca gacaaacaaa agaatggaat caaagttaac
4201  ttcaaaatta gacacaacat tgaagatgga agcgttcaac tagcagacca ttatcaacaa
4261  aatactccaa ttggcgatgg ccctgtcctt ttaccagaca accattacct gtccacacaa
4321  tctgcccttt cgaaagatcc aacgaaaag agagaccaca tggtccttct tgagtttgta
4381  acagctgctg ggattacaca tggcatggat gaactataca aataaaggcc tttaactctg
4441  gtttcattaa attttcttta gtttgaattt actgttattc ggtgtgcatt tctatgtttg
4501  gtgagcggtt ttctgtgctc agagtgtgtt tattttatgt aatttaattt ctttgtgagc
4561  tcctgtttag caggtcgtcc cttcagcaag gacacaaaaa gatttttaatt ttattaaaaa
4621  aaaaaaaaaa aaagaccggg aattcgatat caagcttatc gacctgcaga tcgttcaaac
4681  atttggcaat aaagtttctt aagattgaat cctgttgccg gtcttgcgat gattatcata
4741  taatttctgt tgaattacgt taagcatgta ataattaaca tgtaatgcat gacgttattt
4801  atgagatggg ttttttatgat tagagtcccg caattataca tttaatacgc gatagaaaac
4861  aaaatatagc gcgcaaacta ggataaatta tcgcgcgcgg tgtcatctat gttactagat
4921  ctctagagtc tcaagcttgg cgcgccagct gcattaatga atcggccaac gcgcggggag
4981  aggcggtttg cgtattgggc gctcttccgc ttcctcgctc actgactcgc tgcgctcggt
5041  cgttcggctg cggcgagcgg tatcagctca ctcaaaggcg gtaatacggt tatccacaga
5101  atcaggggat aacgcaggaa agaacatgtg agcaaaaggc cagcaaaagg ccaggaaccg
5161  taaaaaggcc gcgttgctgg cgttttttcca taggctccgc cccctgacg agcatcacaa
5221  aaatcgacgc tcaagtcaga ggtggcgaaa cccgacagga ctataaagat accaggcgtt
5281  tccccctgga agctccctcg tgcgctctcc tgttccgacc ctgccgctta ccggatacct
5341  gtccgccttt ctcccttcgg gaagcgtggc gctttctcat agctcacgct gtaggtatct
5401  cagttcggtg taggtcgttc gctccaagct gggctgtgtg cacgaacccc ccgttcagcc
5461  cgaccgctgc gccttatccg gtaactatcg tcttgagtcc aacccggtaa gacacgactt
5521  atcgccactg gcagcagcca ctggtaacag gattagcaga gcgaggtatg taggcggtgc
5581  tacagagttc ttgaagtggt ggcctaacta cggctacact agaagaacag tatttggtat
5641  ctgcgctctg ctgaagccag ttaccttcgg aaaaagagtt ggtagctctt gatccggcaa
5701  acaaaccacc gctggtagcg gtggtttttt tgtttgcaag cagcagatta cgcgcagaaa
5761  aaaaggatct caagaagatc ctttgatctt ttctacgggg tctgacgctc agtggaacga
5821  aaactcacgt taagggattt tggttatgag attatcaaaa aggatcttca cctagatcct
5881  tttaaattaa aaatgaagtt ttaaatcaat ctaaagtata tatgagtaaa cttggtctga
5941  cagttaccaa tgcttaatca gtgaggcacc tatctcagcg atctgtctat ttcgttcatc
6001  catagttgcc tgactccccg tcgtgtagat aactacgata cgggagggct taccatctgg
6061  ccccagtgct gcaatgatac cgcgagaccc acgctcaccg gctccagatt tatcagcaat
6121  aaaccagcca gccggaaggg ccgagcgcag aagtggtcct gcaactttat ccgcctccat
6181  ccagtctatt aattgttgcc gggaagctag agtaagtagt tcgccagtta atagtttgcg
6241  caacgttgtt gccattgcta caggcatcgt ggtgtcacgc tcgtcgtttg gtatggcttc
6301  attcagctcc ggttcccaac gatcaaggcg agttacatga tcccccatgt tgtgcaaaaa
```

| Nucleotide Sequence of pM81-FSC-1 | |
|---|---|
| 6361 | agcggttagc tccttcggtc ctccgatcgt tgtcagaagt aagttggccg cagtgttatc |
| 6421 | actcatggtt atggcagcac tgcataattc tcttactgtc atgccatccg taagatgctt |
| 6481 | ttctgtgact ggtgagtact caaccaagtc attctgagaa tagtgtatgc ggcgaccgag |
| 6541 | ttgctcttgc ccggcgtcaa tacgggataa taccgcgcca catagcagaa ctttaaaagt |
| 6601 | gctcatcatt ggaaaacgtt cttcggggcg aaaactctca aggatcttac cgctgttgag |
| 6661 | atccagttcg atgtaaccca ctcgtgcacc caactgatct tcagcatctt ttactttcac |
| 6721 | cagcgtttct gggtgagcaa aaacaggaag gcaaaatgcc gcaaaaaagg gaataagggc |
| 6781 | gacacggaaa tgttgaatac tcatactctt cctttttcaa tattattgaa gcatttatca |
| 6841 | gggttattgt cttatgagcg gatacatatt tgaatgtatt tagaaaaata aacaaatagg |
| 6901 | ggttccgcgc acatttcccc gaaaagtgcc acctaaattg taagcgttaa tattttgtta |
| 6961 | aaattcgcgt taaattttg ttaaatcagc tcattttta accaataggc cgaaatcggc |
| 7021 | aaaatccctt ataaatcaaa agaatagacc gagatagggt tgagtgttgt tccagtttgg |
| 7081 | aacaagagtc cactattaaa gaacgtggac tccaacgtca agggcgaaa aaccgtctat |
| 7141 | cagggcgatg gcccactacg tgaaccatca ccctaatcaa gttttttggg gtcgaggtgc |
| 7201 | cgtaaagcac taaatcggaa ccctaaaggg agcccccgat ttagagcttg acggggaaag |
| 7261 | ccggcgaacg tggcgagaaa ggaagggaag aaagcgaaag gagcgggcgc tagggcgctg |
| 7321 | gcaagtgtag cggtcacgct gcgcgtaacc accacacccg ccgcgcttaa tgcgccgcta |
| 7381 | cagggcgcgt cccattcgcc attcaggctg cgcaactgtt gggaagggcg atcggtgcgg |
| 7441 | gcctcttcgc tattacgcca gctggcgaaa gggggatgtg ctgcaaggcg attaagttgg |
| 7501 | gtaacgccag gttttccca gtcacgacgt tgtaaaacga cggccagtga gtactttggc |
| 7561 | gtaatcatgg tcatagctgt ttcctgtgtg aaattgttat ccgctcacaa ttccacacaa |
| 7621 | catacgagcc ggaagcataa agtgtaaagc ctggggtgcc taatgagtga gctaactcac |
| 7681<br>// | attaattgcg ttgcgctcac tgcccgcttt ccagtcggga aacctggcgc gc |

| Nucleotide Sequence of pM81-FSC-2 | |
|---|---|
| | SEQ ID NO: 10 |
| LOCUS | pM81-FSC2 4173 bp DNA circular<br>10 Oct. 2007 |
| FEATURES | Location/Qualifiers |
| rep_origin | complement(1271..1890)<br>/vntifkey = "33"<br>/label = pBR322_origin |
| rep_origin | complement(3168..3474)<br>/vntifkey = "33"<br>/label = f1_origin |
| promoter | complement(2947..2975)<br>/vntifkey = "30"<br>/label = AmpR\promoter |
| misc_feature | complement(3492..3647)<br>/vntifkey = "21"<br>/label = lacZ_a |
| CDS | complement(2045..2905)<br>/vntifkey = "4"<br>/label = AmpR |
| 3'UTR | 533..716<br>/vntifkey = "50"<br>/label = CPMV\RNA2\3'UTR |
| terminator | 770..1022<br>/vntifkey = "43"<br>/label = Nos\Terminator |

| Nucleotide Sequence of pM81-FSC-2 |
|---|

```
            promoter        3859..4173
                            /vntifkey = "29"
                            /label = CaMV\35S\promoter
            5'UTR           1..160
                            /vntifkey = "52"
                            /label = CPMV\RNA2\5'UTR
            misc_feature    507..532
                            /vntifkey = "21"
                            /label = FSC-2\MCS BASE COUNT  1090 a 969 c 982 g 1132 t ORIGIN
    1   tattaaaatc ttaataggtt ttgataaaag cgaacgtggg gaaacccgaa ccaaaccttc
   61   ttctaaactc tctctcatct ctcttaaagc aaacttctct cttgtctttc ttgcatgagc
  121   gatcttcaac gttgtcagat cgtgcttcgg caccagtaca atgttttctt tcactgaagc
  181   gaaatcaaag atctctttgt ggacacgtag tgcggcgcca ttaaataacg tgtacttgtc
  241   ctattcttgt cggtgtggtc ttgggaaaag aaagcttgct ggaggctgct gttcagcccc
  301   atacattact tgttacgatt ctgctgactt tcggcgggtg caatatctct acttctgctt
  361   gacgaggtat tgttgcctgt acttctttct tcttcttctt gctgattggt tctataagaa
  421   atctagtatt ttctttgaaa cagagttttc ccgtggtttt cgaacttgga gaaagattgt
  481   taagcttctg tatattctgc ccaaattcgc gacgatcgta ctctcgaggc ctttaactct
  541   ggtttcatta aattttcttt agtttgaatt tactgttatt cggtgtgcat ttctatgttt
  601   ggtgagcggt tttctgtgct cagagtgtgt ttattttatg taatttaatt tctttgtgag
  661   ctcctgttta gcaggtcgtc ccttcagcaa ggacacaaaa agatttaat tttattaaaa
  721   aaaaaaaaaa aaagaccgg gaattcgata tcaagcttat cgacctgcag atcgttcaaa
  781   catttggcaa taaagttct taagattgaa tcctgttgcc ggtcttgcga tgattatcat
  841   ataattctg ttgaattacg ttaagcatgt aataattaac atgtaatgca tgacgttatt
  901   tatgagatgg gttttatga ttagagtccc gcaattatac atttaatacg cgatagaaaa
   61   caaaatatag cgcgcaaact aggataaatt atcgcgcgcg gtgtcatcta tgttactaga
 1021   tctctagagt ctcaagcttg gcgcgccagc tgcattaatg aatcggccaa cgcgcgggga
 1081   gaggcggttt gcgtattggg cgctcttccg cttcctcgct cactgactcg ctgcgctcgg
 1141   tcgttcggct gcggcgagcg gtatcagctc actcaaaggc ggtaatacgg ttatccacag
 1201   aatcagggga taacgcagga agaacatgt gagcaaaagg ccagcaaaag gccaggaacc
 1261   gtaaaaggc cgcgttgctg gcgtttttcc ataggctccg ccccctgac gagcatcaca
 1321   aaaatcgacg ctcaagtcag aggtggcgaa acccgacagg actataaaga taccaggcgt
 1381   ttccccctgg aagctccctc gtgcgctctc ctgttccgac cctgccgctt accggatacc
 1441   tgtccgcctt tctcccttcg ggaagcgtgg cgctttctca tagctcacgc tgtaggtatc
 1501   tcagttcggt gtaggtcgtt cgctccaagc tgggctgtgt gcacgaaccc ccgttcagc
 1561   ccgaccgctg cgccttatcc ggtaactatc gtcttgagtc aacccggta agacacgact
 1621   tatcgccact ggcagcagcc actggtaaca ggattagcag agcgaggtat gtaggcggtg
 1681   ctacagagtt cttgaagtgg tggcctaact acggctacac tagaagaaca gtatttggta
 1741   tctgcgctct gctgaagcca gttaccttcg gaaaaagagt tggtagctct tgatccggca
 1801   aacaaaccac cgctggtagc ggtggttttt tgtttgcaa gcagcagatt acgcgcagaa
 1861   aaaaggatc tcaagaagat cctttgatct tttctacggg gtctgacgct cagtggaacg
```

| Nucleotide Sequence of pM81-FSC-2 |
|---|
| 1921 aaaactcacg ttaagggatt ttggttatga gattatcaaa aaggatcttc acctagatcc |
| 1981 ttttaaatta aaaatgaagt tttaaatcaa tctaaagtat atatgagtaa acttggtctg |
| 2041 acagttacca atgcttaatc agtgaggcac ctatctcagc gatctgtcta tttcgttcat |
| 2101 ccatagttgc ctgactcccc gtcgtgtaga taactacgat acgggagggc ttaccatctg |
| 2161 gccccagtgc tgcaatgata ccgcgagacc cacgctcacc ggctccagat ttatcagcaa |
| 2221 taaaccagcc agccggaagg gccgagcgca gaagtggtcc tgcaacttta tccgcctcca |
| 2281 tccagtctat taattgttgc cgggaagcta gagtaagtag ttcgccagtt aatagtttgc |
| 2341 gcaacgttgt tgccattgct acaggcatcg tggtgtcacg ctcgtcgttt ggtatggctt |
| 2401 cattcagctc cggttcccaa cgatcaaggc gagttacatg atccccatg ttgtgcaaaa |
| 2461 aagcggttag ctccttcggt cctccgatcg ttgtcagaag taagttggcc gcagtgttat |
| 2521 cactcatggt tatggcagca ctgcataatt ctcttactgt catgccatcc gtaagatgct |
| 2581 tttctgtgac tggtgagtac tcaaccaagt cattctgaga atagtgtatg cggcgaccga |
| 2641 gttgctcttg cccggcgtca atacgggata ataccgcgcc acatagcaga actttaaaag |
| 2701 tgctcatcat tggaaaacgt tcttcggggc gaaaactctc aaggatctta ccgctgttga |
| 2761 gatccagttc gatgtaaccc actcgtgcac ccaactgatc ttcagcatct tttactttca |
| 2821 ccagcgtttc tgggtgagca aaaacaggaa ggcaaaatgc cgcaaaaaag gaataagggc |
| 2881 cgacacggaa atgttgaata ctcatactct ccttttttca atattattga agcatttatc |
| 2941 agggttattg tcttatgagc ggatacatat ttgaatgtat ttagaaaaat aaacaaatag |
| 3001 gggttccgcg cacatttccc cgaaaagtgc cacctaaatt gtaagcgtta atattttgtt |
| 3061 aaaattcgcg ttaaattttt gttaaatcag ctcattttt aaccataggg ccgaaatcgg |
| 3121 caaaatccct tataaatcaa agaatagac gagatagggg ttgagtgttg ttccagtttg |
| 3181 gaacaagagt ccactattaa agaacgtgga ctccaacgtc aaagggcgaa aaaccgtcta |
| 3241 tcagggcgat ggcccactac gtgaaccatc accctaatca gtttttttgg ggtcgaggtg |
| 3301 ccgtaaagca ctaaatcgga acctaaaagg gagcccccga tttagagctt gacggggaaa |
| 3361 gccggcgaac gtggcgagaa aggaagggaa gaaagcgaaa ggagcgggcg ctagggcgct |
| 3421 ggcaagtgta gcggtcacgc tgcgcgtaac caccacaccc gccgcgctta atgcgccgct |
| 3481 acagggcgcg tcccattcgc cattcaggct gcgcaactgt tgggaagggc gatcggtgcg |
| 3541 ggcctcttcg ctattacgcc agctggcgaa agggggatgt gctgcaaggc gattaagttg |
| 3601 ggtaacgcca gggttttccc agtcacgacg ttgtaaaacg acggccagtg agtactttgg |
| 3661 cgtaatcatg gtcatagctg tttcctgtgt gaattgtta tccgctcaca attccacaca |
| 3721 acatacgagc cggaagcata aagtgtaaag cctggggtgc ctaatgagtg agctaactca |
| 3781 cattaattgc gttgcgctca ctgcccgctt tccagtcggg aaacctggcc gcttaattaa |
| 3841 gaattcgagc tccaccgcgg aaacctcctc ggattccatt gcccagctat ctgtcacttt |
| 3901 attgagaaga tagtggaaaa ggaaggtggc tcctacaaat gccatcattg cgataaagga |
| 3961 aaggccatcg ttgaagatgc ctctgccgac agtggtccca agatgacc cccacccacg |
| 4021 aggagcatcg tggaaaaaga agacgttcca accacgtctt caaagcaagt ggattgatgt |
| 4081 gatatctcca ctgacgtaag ggatgacgca caatcccact atccttcgca agacccttcc |
| 4141 tctatataag gaagttcatt tcatttggag agg |
| // |

Example 7

Extremely High-Level and Rapid Transient Protein Production in Plants without the Use of Viral Replication

Plant-based overexpression of heterologous proteins has attracted much interest and development in recent years. To date, the most efficient vectors have been based on RNA virus-derived replicons. A system based on a disabled version of cowpea mosaic virus RNA-2 has been developed, which overcomes limitations on insert size and introduces biocontainment. This system involves positioning a gene of interest between the 5' leader sequence and 3' untranslated region (UTR) of RNA-2, thereby emulating a presumably stable mRNA for efficient translation. Thus far, the sequence of the 5' UTR has been preserved to maintain the ability of the modified RNA-2 to be replicated by RNA-1. However, high-level expression may be achieved in the absence of RNA-1-derived replication functions using *Agrobacterium*-mediated transient transformation. To investigate those features of the 5' UTR necessary for efficient expression, we have addressed the role of two AUG codons found within the 5' leader sequence upstream of the main initiation start site. Deletion of an in-frame start codon upstream of the main translation initiation site led to a massive increase in foreign protein accumulation. By 6 d postinfiltration, a number of unrelated proteins, including a full-size IgG and a self-assembling virus-like particle, were expressed to >10% and 20% of total extractable protein, respectively. Thus, this system provides an ideal vehicle for high-level expression that does not rely on viral replication of transcripts.

The production of eukaryotic proteins for academic and industrial purposes can present significant challenges in terms of solubility and posttranslational modifications. For this reason, a number of eukaryotic protein production systems have been developed (Aricescu et al., 2006; Yin et al., 2007). Plants and plant cells possess many advantages over other eukaryotic expression hosts, such as high biomass, ease of scale-up, cost effectiveness, and low risk of contamination (Ma et al., 2003; Twyman et al., 2003). Although much work has been carried out using stably transformed plants, the significantly reduced development and production timelines make transient plant-based expression a particularly attractive option for the production of proteins of both commercial and academic interest.

To date, the most efficient means of achieving high-level transient expression of foreign proteins in plants has involved the use of vectors based on RNA plant viruses (Giritch et al., 2006; Lindbo, 2007), including the bipartite comovirus Cowpea mosaic virus (CPMV; Sainsbury et al., 2007). These systems take advantage of the ability of RNA viruses to replicate to high titers within infected cells. However, virus-directed replication of RNA has a number of undesirable features, including restrictions on the size of insert that can be accommodated without affecting replication and compromised fidelity of transcripts due to the lack of proofreading by RNA-dependent RNA polymerases (Ahlquist et al., 2005; Castro et al., 2005). In addition, vectors based on full-length viral replicons, which can move throughout a plant, suffer from problems of biocontainment.

To address the issue of biocontainment and to overcome the problem of insert size, we recently developed a system based on a disabled version of CPMV RNA-2 (deRNA-2; Cañizares et al., 2006; Sainsbury et al., 2008b). In this approach, the majority of the coding region of RNA-2 was replaced by a gene of interest. The sequence to be expressed was fused to the AUG at position 512 of RNA-2 because sequences upstream of this site had previously been shown to be essential for replication of RNA-2 by the RNA-1-encoded replication complex (Rohll et al., 1993). In addition, it was positioned immediately upstream of the 3' untranslated region (UTR) to create a molecule that mimics RNA-2. Such constructs were shown to be capable of replication when agroinfiltrated into plants in the presence of RNA-1 and a suppressor of silencing and to direct the synthesis of substantial levels of heterologous proteins (Cañizares et al., 2006). Furthermore, it was demonstrated that the system was suitable for the production of heteromeric proteins, such as full-length antibodies (Sainsbury et al., 2008a).

Although the AUG at position 512 constitutes the major site of translation initiation on RNA-2 (Holness et al., 1989), the upstream sequence contains two additional AUGs at positions 115 and 161. Whereas the AUG at 115 is out of frame with that at 512 and has no known function (Wellink et al., 1993b), the AUG at position 161 is in-frame with AUG 512 and is functional as an initiation codon (Holness et al., 1989). Either deleting AUG 161 or disrupting its frame relationship with AUG 512 effectively eliminates RNA-2 replication (Holness et al., 1989; van Bokhoven et al., 1993). The need to preserve the frame relationship between AUG 161 and 512 to retain the replication ability of RNA-2-based constructs complicates the construction of vectors (Sainsbury et al., 2008b). However, whereas replication of the RNA-2-based constructs is essential to achieve high levels of expression when the mRNA is expressed from a transgene (Cañizares et al., 2006), it is less important with transient expression because large quantities of mRNA accumulate in agroinfiltrated tissue. This is particularly the case if a suppressor of silencing is coinfiltrated. We have therefore examined whether the upstream AUG codons can be eliminated without unduly compromising expression levels. Unexpectedly, the results obtained showed that expression can be greatly enhanced by eliminating the AUG at position 161. This observation has been used to design a simple and effective method for the production of high levels of proteins within plants.

Results

Figures 16A, 16B:
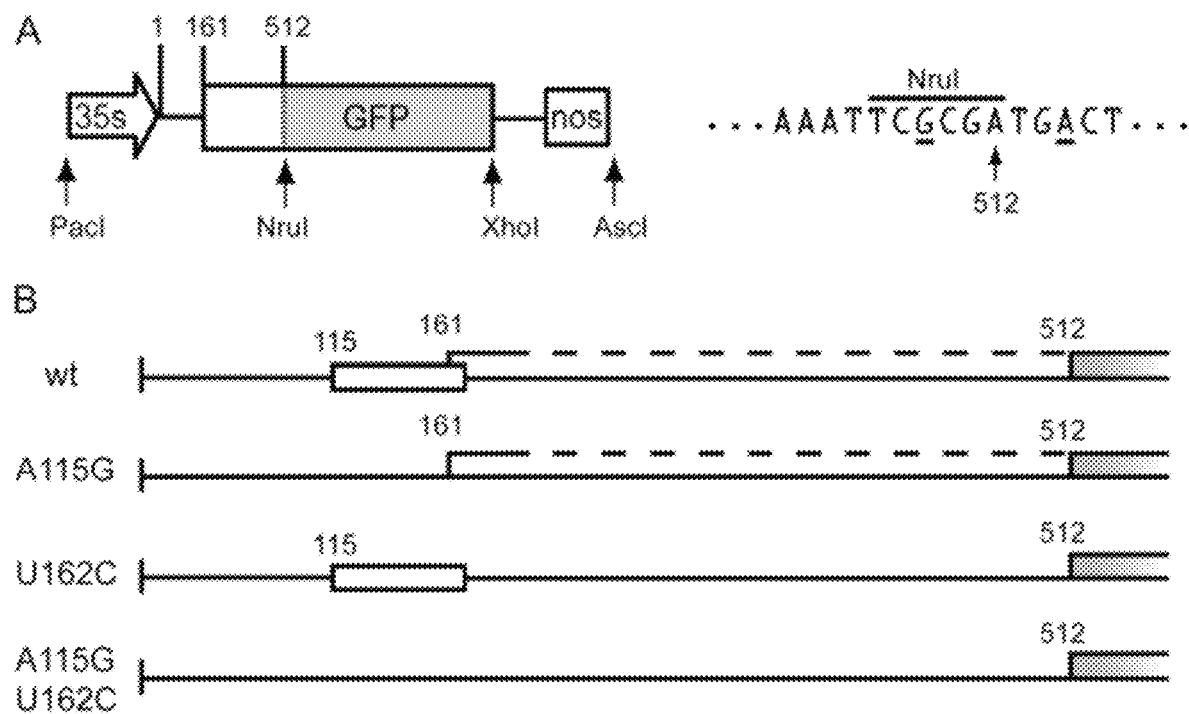
FIG. 16A-16B shows expression cassette used and mutations to the 5' leader sequence of CPMV RNA-2. (A) Schematic representation of the expression cassette from the cloning vector pM81-FSC2, with detail surrounding the AUG at position 512 showing the +4 and −3 Kozak consensus positions underlined. (B) Schematic diagram of the mutations made to the 5' leader (from nucleotides 1-512 in A). The positions of 5' AUGs are indicated and the GFP sequence is shown as gray.

Removal of Upstream AUG Codons Greatly Improves GFP Expression Levels in a Transient Assay To create a useful cloning vector, a derivative of the original deRNA-2 construct containing GFP (1-GFP; Cañizares et al., 2006), called pM81-FSC2, was created. This allows easy replacement of GFP by other sequences using unique NruI and XhoI restriction sites (FIG. 16A). Use of the NruI site allows the insert to be precisely aligned with AUG 512, where translation is expected to exclusively initiate (Cañizares et al., 2006). To examine the effect of the AUGs upstream of AUG 512 on GFP expression levels, mutations that removed one or both of AUG 115 and AUG 161 were introduced into pM81-FSC2 (FIG. 16B). Following transfer of the expression cassette into the binary vector pBINPLUS (van Engelen et al., 1995), the GFP constructs were agroinfiltrated into *Nicotiana benthamiana* leaves in the presence of the suppressor of silencing P19 (Voinnet et al., 2003) and the levels of GFP expression assessed.

Figures 17A, 17B, 17C:
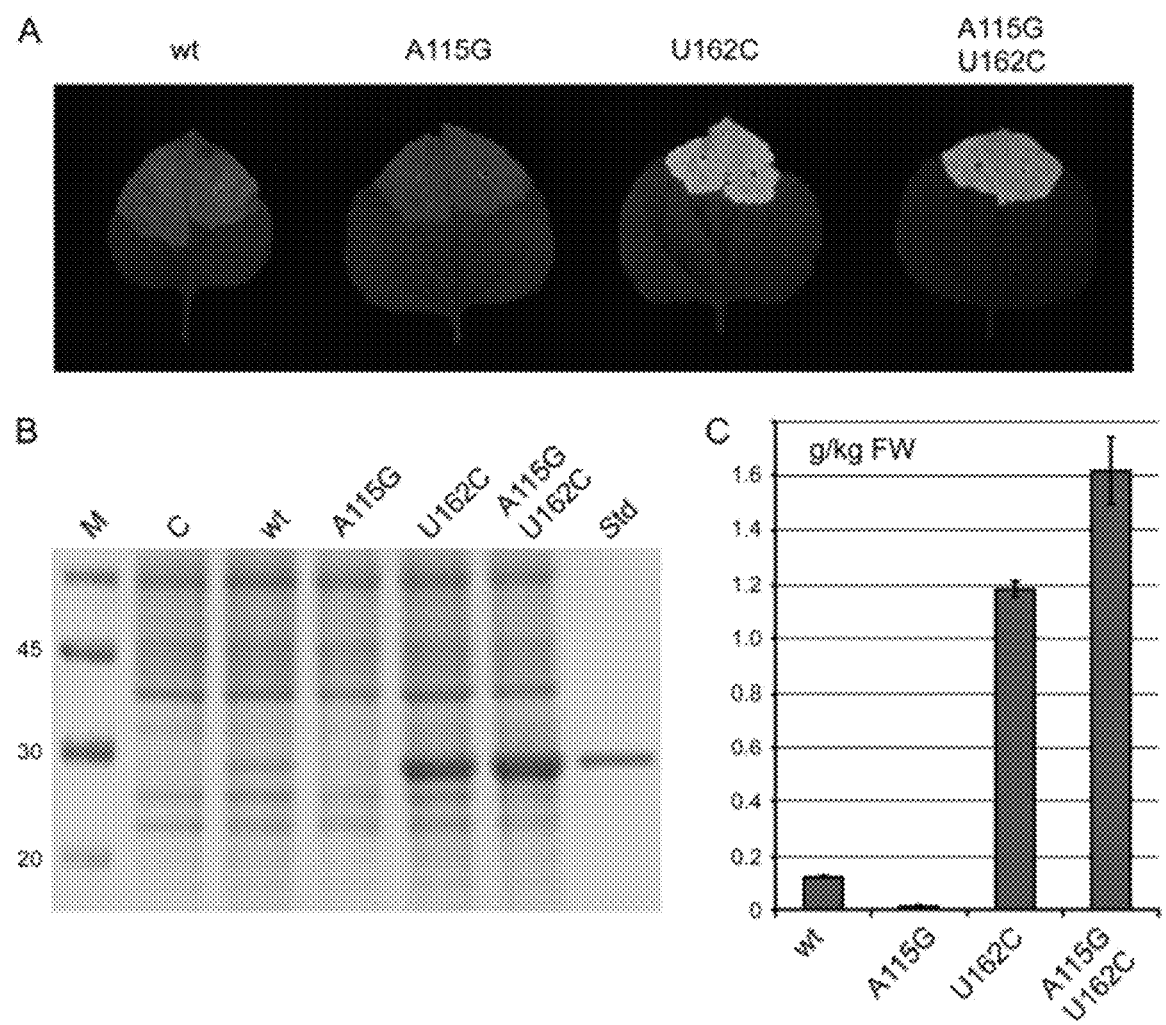
FIG. 17A-17C shows effect of the AUG 115 (A115G) and AUG 161 (U162C) mutations on GFP expression 5 d postinfiltration in *N. benthamiana* leaves. (A) GFP fluorescence as seen under UV light. (B) Coomassie-stained SDS-PAGE gel of approximately 25 µg of protein per lane extracted from infiltrated tissue. M, Marker with sizes indicated; (C) control extract; wt, wild type; Std, 1 µg of recombinant GFP. C, GFP accumulation in infiltrated tissue measured by spectrofluorometry. Values represent averages from three extracts SD.

Examination of infiltrated tissue under UV light indicated that removal of AUG 115 alone resulted in a decrease in GFP expression to barely detectable levels (FIG. 17A, A115G). By contrast, removal of the in-frame AUG at 161 appeared to result in a dramatic increase in GFP expression levels (FIG. 17A, U162C). A similar enhancement was found when both AUGs at 115 and 161 were removed (FIG. 17A, A115G, U162C). Analysis of protein extracts by SDS-PAGE confirmed these findings and indicated that GFP accumulates to 20% to 25% of the extractable protein when AUG 161 is deleted, whether or not the AUG at 115 is present (FIG. 17B). This high-level expression was confirmed by analysis of the GFP fluorescence extracted from leaves by spectrofluorometry and corresponds to a level approaching 1.2 g/kg GFP of fresh-weight tissue (FIG. 17C). This represents at least a 10-fold increase in the levels obtained when the unmodified 5' leader was used. The spectrofluorometric analysis also revealed that the maximum level of expression, 1.6 g/kg GFP of fresh-weight tissue, is obtained when both AUG 161 and AUG 115 are eliminated.

Increased Expression Levels are not Due to Increased mRNA Accumulation

To determine whether the increase in protein expression observed after removal of AUG 161 is due to increased levels of mRNA as a result of the mutations in the mutated 5' leaders, quantitative reverse transcription (RT)-PCR was performed on RNA extracted from leaf tissue infiltrated with the various constructs. The levels of GFP-specific mRNA did not vary significantly with the nature of the 5' leader sequence used.

Figure 18:
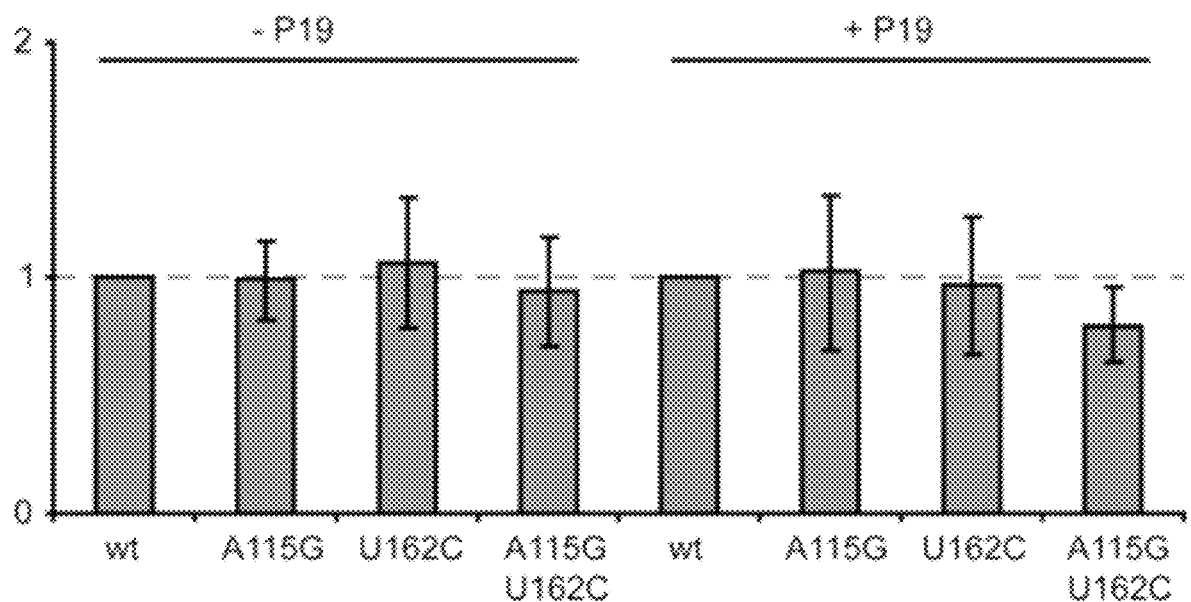
FIG. 18 shows analysis of RNA accumulation from the wild-type (wt) and mutant 5' leader sequences either in the absence or presence of P19. Values indicate the average proportion of transcripts relative to the wild-type leader from three extracts SE.

This lack of variation was found whether or not a construct expressing P19 was coinfiltrated (FIG. 18). These results indicate that the enhanced levels of protein expression found when AUG 161 is deleted are not due to enhanced levels of mRNA accumulation, but rather to the mRNA molecules being hyper-translated relative to the wild-type leader. For this reason, we refer to the RNA-2 leader lacking AUG 161 as the hypertranslatable (HT) leader.

The HT Leader is a General Enhancer of Protein Expression in Plants

Figures 19A, 19B, 19C, 19D:
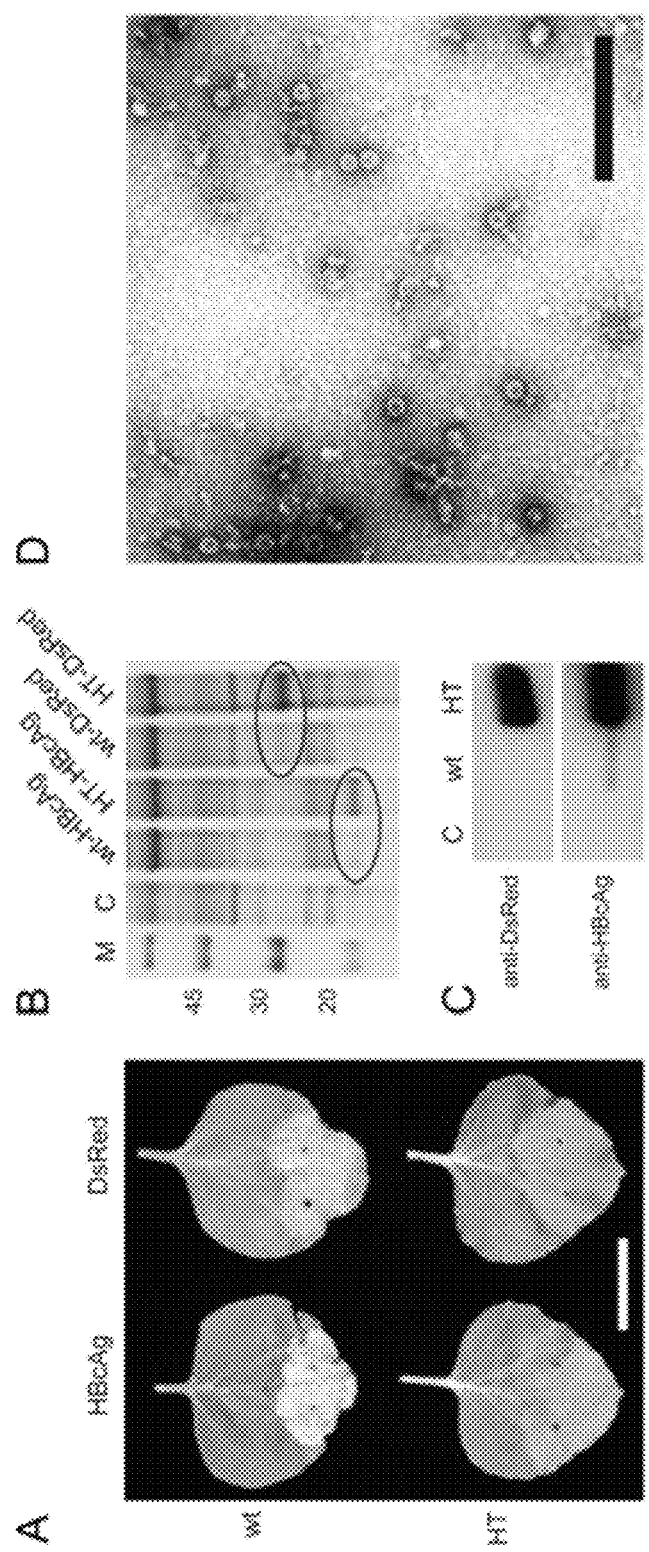
FIG. 19A-19D shows expression of DsRed and HBcAg cloned downstream of wild-type (wt) and HT (U162C) 5' leaders. (A) Leaves 6 d postinfiltration expressing HBcAg and DsRed downstream of either the wild-type or the HT 5' leader. Scale bar, 2.5 cm. (B) Coomassie-stained SDS-PAGE gel of approximately 25 µg of protein per lane extracted from tissue infiltrated with constructs as indicated. M, Marker with sizes indicated; (C) control extract. C, Immunological detection of DsRed (top) or HBcAg (bottom) expression using either the wild-type or the HT 5' leader. (D) Transmission electron microscopy of crude extracts of HT-HBcAg following buffer exchange and negative staining with 2% uranyl acetate. Scale bar, 250 nm.

To examine whether the HT leader is generally effective at increasing expression of heterologous proteins, the Discosoma red fluorescent protein (DsRed) and the Hepatitis B core antigen (HBcAg) were each inserted downstream of either the wild-type or the HT 5' leader. When infiltrated into N. benthamiana leaves, the HT-based constructs appeared to cause less necrosis in the infiltrated patches than the wild-type equivalent (FIG. 19A). Furthermore, infiltration with the DsRed construct gives a reddish hue to the infiltrated leaf patches, suggesting high levels of accumulation of this protein. SDS-PAGE of proteins extracted from infiltrated patches showed that, for both proteins, elimination of AUG 161 led to a substantial increase in accumulation over that obtained with the wild-type leader (FIG. 19B). In each case, the identity of the expressed proteins was confirmed by western blotting (FIG. 19C). DsRed appears to accumulate to similar levels to that of GFP (approximately 25% of the extractable protein; compare FIGS. 17B and 19B). The HBcAg accumulates to approximately 1 g/kg of fresh-weight tissue as determined by ELISA using anti-HBcAg antibodies (E. Thuenemann, personal communication), which corresponds to around 20% of the extractable protein. To confirm that the expressed HBcAg was assembly competent, samples of leaf tissue were extracted in 3 volumes of Tris-NaCl buffer and subject to buffer exchange into Tris-EDTA, without concentration, using a 100-kD molecular cutoff column. Transmission electron microscopy of this crude preparation showed the presence of many virus-like particles, which we estimate comprise about 50% of the remaining total protein in the sample (FIG. 19D).

Figures 20A, 20B, 20C:
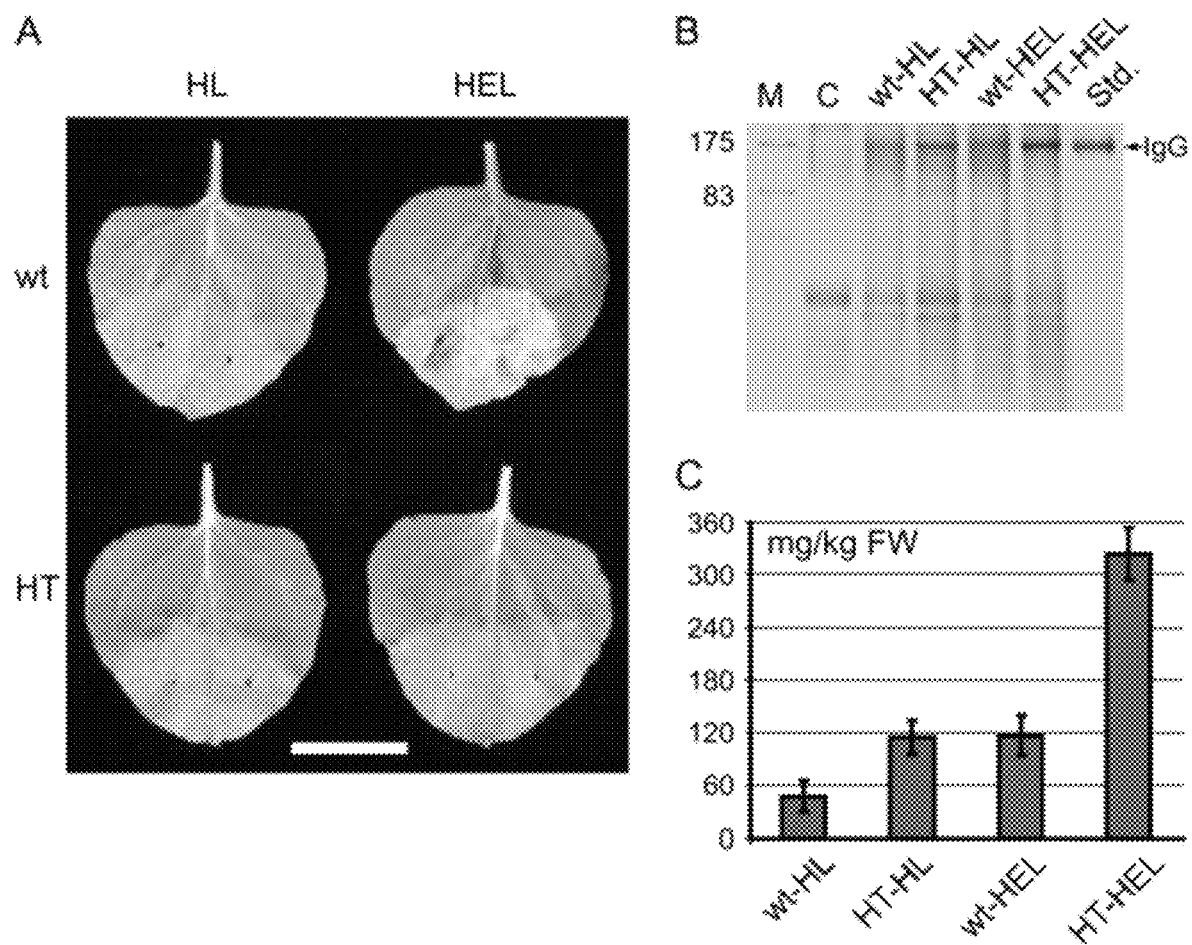
FIG. 20A-20C shows expression of the human anti-HIV IgG using wild-type (wt) and HT leaders. (A) Leaves 6-d post-infiltration expressing 2G12, with (HEL) or without (HL) ER retention of the heavy chain, downstream of either the wild-type or the HT 5' leader. Scale bar, 2.5 cm. (B) Coomassie-stained nonreducing SDS-PAGE gel of approximately 12.5 µg of protein per lane extracted from tissue infiltrated with constructs as indicated. M, Marker with sizes indicated; (C) control extract; Std, 1 µg of human IgG. C, 2G12 accumulation in extracts of 2G12 and HT-2G12 infiltrated tissue measured by SPR using a protein-A-coated surface. Values repre-sent averages from three extracts SD.

One of the advantages of CPMV expression systems over those based on other viruses is their ability to simultaneously express multiple polypeptides in the same plant cell (Sainsbury et al., 2008a). To test whether this ability is retained when the HT leader is used, the heavy (H) and light (L) chains of the human anti-HIV antibody 2G12 (Buchacher et al., 1994) were inserted downstream of either the wild-type or the HT 5' leader. In both cases, the immunoglobulin chains retained their native leader peptides and two forms of the H chain were constructed, with (HE) and without (H) an endoplasmic reticulum (ER) retention motif. To obtain expression of full-size antibody, a combination of the L and either of the H chain constructs was coinfiltrated with P19 into N. benthamiana leaves (FIG. 20A). Analysis of total protein extracts by SDS-PAGE on nonreducing gels again suggested that higher levels of assembled antibody accumulation were obtained when the HT leader was used (FIG. 20B). The benefit of the HT over the wild-type leader was seen regardless of ER retention, although overall levels were higher when the antibody was retained. Quantification of IgG levels showed that the ER-retained 2G12 expressed using the HT leader (HT-HEL) accumulated to a yield in excess of 325 mg/kg of fresh-weight tissue (FIG. 20C). Furthermore, we have found that purified 2G12 produced in this way is comparable to 2G12 from other plant-based systems or from the mammalian cell-produced control in terms of antigen binding and virus neutralization in vitro (M. Sack and F. Sainsbury, unpublished data).

DISCUSSION

The results presented here represent the highest reported level of plant-based protein production without the use of viral replication. We report the creation of an expression system based on a version of CPMV RNA-2 that is hyper-translatable relative to the wild-type version. By the removal of an upstream AUG that appears to inhibit translation, the system allows a variety of proteins to be produced to levels similar to that from state-of-the-art viral vectors in a matter of days, and without concomitant shortcomings of viral replication of transcripts. A recent study (Lindbo, 2007) showed 100-fold better expression for a single protein, GFP, from a tobacco mosaic virus (TMV)-based vector than when P19 was coinfiltrated with a cauliflower mosaic virus 35S promoter-driven construct. The HT constructs used in this study produced GFP levels in the same order of magnitude as the highest achieved with the TMV vector used in that study.

A significant disadvantage of vectors based on monopartite viruses, such as TMV, is their inability to coexpress multiple proteins. This limitation can be overcome by using vectors based on two different viruses that exist synergistically in nature, such as TMV and Potato virus X (Pruss et al., 1997). Using this noncompeting viral vector approach, Giritch et al. (2006) expressed the separate H and L chains of a tumor-specific IgG in TMV and potato virus X-based vectors. Depending on the vector-IgG combination used, yields of assembled antibody of 0.2 to 0.5 g/kg fresh-weight tissue were reported. In the case of the CPMV-HT system, levels of assembled 2G12 in excess of 0.3 g/kg fresh-weight tissue were obtained, a level comparable with the virus-based system. However, the viral vector-based system involved the coinfiltration of six Agrobacterium cultures took 10 d to reach maximum expression, and resulted in the production of infectious virus particles from the potato virus X construct used. In contrast, the HT expression required the coinfiltration of only three cultures, an incubation of only 6 d, and is fully biocontained, with no infectious virus being produced. Furthermore, the non-competing viral vector approach is likely to be limited to the coexpression of only two proteins, unless additional noncompeting viruses can be found. In contrast, there is no obvious limit on the number of CPMV RNA-2-based constructs that can be coinfiltrated, raising the possibility of the production of multichain complexes.

The question arises as to why deletion of AUG 161 enhances expression from AUG 512. Although translation does occur from AUG 161 on wild-type CPMV RNA-2, the massive increase in expression resulting from the removal of AUG 161 suggests that the presence of AUG 161 is inhibitory to overall translation. A possible mechanism for this is that the majority of ribosomes that do not initiate at AUG 161 are unable to proceed to the downstream AUG 512. If this is the case, it suggests a possible function for the short open reading frame (ORF), which begins at AUG 115 and overlaps AUG 161, in bypassing this start codon. Initiation is known to occur at AUG 115 in vitro (Wellink et al., 1993b) and a possible bypassing of AUG 161 would potentially permit efficient translation at AUG 512 following reinitiation. This hypothesis is supported by the observed reduction in expression from AUG 512 when AUG 115 is removed and AUG 161 is retained (FIG. 17). Examples of short ORFs regulating expression from the main ORF following reinitiation have been described for eukaryotic as well as virus genes (Morris and Geballe, 2000; Ryabova et al., 2006). Thus, removal of the AUG at 161 appears to free translation from inhibition imposed by the presence of this start codon. A possible reason for a deliberate reduction in translation is to allow 3' to 5' movement of the RNA-1-encoded replicase on at least some transcripts, which would require RNA relatively free of ribosomes (Gamarnik and Andino, 1998).

An unexpected benefit of the removal of AUG 161 was that the increase in foreign protein production was accompanied by a reduction in the amount of tissue necrosis previously observed with some constructs (FIGS. 19 and 20). Although an N-terminal fusion protein that would theoretically be produced by initiation at AUG 161 has not been detected (Cañizares et al., 2006), the N-terminal sequence of such a fusion may direct the polypeptide to the nucleus (Wellink et al., 1993a) with a potential toxic effect. Any such effect would therefore be alleviated by the prevention of initiation at AUG 161.

CONCLUSION

The results reported here show that it is possible to express very high levels of foreign proteins in plants without viral replication through the use of a modified version of the CPMV RNA-2 5' leader. CPMV-HT provides a quick, easy, and inexpensive eukaryotic expression system that will prove very useful for the production of large quantities of recombinant proteins. Expression levels are similar to the highest reported so far from systems relying on viral replication. In addition to the biological advantages over viral vectors, such as the absence of RNA-dependent RNA polymerases and restrictions on insert size, the use of CPMV-HT does not require a license for work with plant pathogens. Therefore, this system presents an extremely useful and accessible tool in the fields of plant biology and biotechnology.

Materials and Methods
Plasmid Constructs

A combination of oligonucleotide insertion and site-directed mutagenesis on pM81-FSC1 (Sainsbury et al., 2008b) resulted in the production of pM81-FSC2 (FIG. 16), which allows cloning with NruI and either XhoI or StuI. The terminal adenine of the NruI site lies at position 512, thereby allowing preservation of the AUG at this position. The modifications altered nucleotides immediately 5' to the AUG at 512; however, a good context was maintained. The GFP sequence was amplified by PCR from pBinP-NS-1 (Liu et al., 2005) with primers that incorporated a 5' NruI site and a 3' XhoI site. The resulting NruI/XhoI fragment was inserted into similarly digested pM81-FSC2 to give pM81-FSC2-GFP. Complementary pairs of oligonucleotides were used in the site-directed mutagenesis of pM81-FSC2-GFP (Quickchange; Stratagene). Oligos to remove the AUG at 115 were A115G-F, 5'-CTTGTCTTTCTTGC GTG-AGCGATCTTCAACG-3' and A115G-R, 5'-CGTT-GAAGATCGCTCACGCAA-GAAAGACAAG-3'. Oligos to remove the AUG at 161, while maintaining the sequence of the putative uORF were U162C-F, 5'-GGCACCAGTA-CAACG-TTTTCTTTCACTGAAGCG-3' and U162C-R, 5'-CGCTTCAGTGAAAGAAA-AC GTTGTACTGGTGCC-3'. The mutant nucleotide is underlined in bold. The double mutation was made by applying the mutagenesis of AUG 161 to the AUG 115 mutant. The pM81-FSC2-derived plasmids were digested with AscI and PacI and the fragment containing the expression cassette including the foreign sequences transferred to the similarly digested binary vector, pBINPLUS (van Engelen et al., 1995).

DsRed (CLONTECH), HBcAg (Mechtcheriakova et al., 2006), and the H and L chains of 2G12 (Buchacher et al., 1994) were initially cloned into pM81-FSC1 via BspHI/StuI sites. For expression with the wild-type leader, PacI/AscI fragments were transferred into similarly digested pBINPLUS. For expression with the modified leaders, DraIII/AscI fragments containing the gene of interest, the 3' UTR, and the nos terminator were transferred into a similarly digested FSC2-GFP-U162C expression cassette within pBINPLUS.

Agroinfiltration

Binary plasmid constructs were maintained in *Agrobacterium tumefaciens* strain LBA4404 and agroinfiltration into *Nicotiana benthamiana* was carried out as follows. Cultures grown to stable phase in Luria-Bertani medium supplemented with the appropriate antibiotics were pelleted by centrifugation at 2,000 g and resuspended in MMA (10 mM MES, pH 5.6, 10 mM $MgCl_2$, 100 M acetosyringone) to an OD600 of 1.2. After 2- to 4-h incubations at room temperature, CPMV-based expression constructs were coinfiltrated at a 1:1 ratio with pBIN61-P19 (Voinnet et al., 2003) and a mix of pBIN61-P19 and pBINPLUS was infiltrated as a control.

Protein Extractions and Electrophoresis

For the extraction of GFP, DsRed, and HBcAg infiltrated leaf tissue was homogenized in 3 volumes of protein extraction buffer (50 mM Tris-HCl, pH 7.25, 150 mM NaCl, 2 mM EDTA, 0.1% [v/v], Triton X-100). For the extraction of 2G12, infiltrated leaf tissue was homogenized in 3 volumes of phosphate-buffered saline with 5 mM EDTA, 3 mM β-mercaptoethanol, 0.05% Triton X-100). Lysates were clarified by centrifugation and protein concentrations determined by the Bradford assay. The protein concentrations of extracts were consistently 2 to 2.5 mg/mL. Approximately 20 g of GFP, DsRed, and HBcAg extracts were separated on 12% NuPage gels (Invitrogen) under reducing conditions and approximately 12.5 g of 2G12 protein extract was separated by Tris-Gly SDS-PAGE under nonreducing conditions. For western blotting, separated extracts were transferred to nitrocellulose membranes and probed with Living Colors DsRed monoclonal antibody (CLONTECH) or rabbit anti-HBcAg (AbD Serotec). Anti-mouse or anti-rabbit horseradish peroxidase-conjugated secondary antibodies were used as appropriate (Amersham Bio-sciences). Signals were generated by chemiluminescence and captured on Hyperfilm (Amersham Biosciences).

Plants and Photography

*N. benthamiana* plants were grown from November to March in green-houses maintained at 23° C. to 25° C. with 16 h of supplementary light per day. Infiltrated leaves were photographed with a Nikon D1x digital camera under visible light or, for the detection of GFP, under UV illumination from a Blak-Ray B-100AP UV lamp (Blak-Ray).

GFP Assay

GFP fluorescence measurements were made using a protocol modified from Richards et al. (2003). Soluble protein extracts were diluted in 0.1 M $Na_2CO_3$ and loaded in triplicate onto a fluorescently neutral black 96-well plate (Costar). Recombinant GFP from CLONTECH is the same variant of GFP as was used in this study and was, therefore, used to generate standard curves in a control plant extract at the same dilution as samples. Excitation (wavelength of 395 nm) and emission (509 nm) maxima were matched to CLONTECH's GFP and read using a SPECTRAmax spectrofluorometer (Molecular Devices).

Quantitative PCR

RNA extractions were performed using Ambion's RNAqueous kit with the plant RNA isolation aid (Ambion) according to the manufacturer's instructions. RNA concentration and quality was determined using a NanoDrop spectrophotometer (NanoDrop Technologies). cDNA was synthesized using the ProtoScript first-strand cDNA synthesis kit (New England BioLabs). RT quantification of target transcripts relative to actin transcripts was revealed by quantitative real-time PCR as measured by a Chromo 4 continuous fluorescence detector coupled to a PTC-200 peltier thermal cycler (MJ research) using SYBR Green JumpStart Taq ready mix (Sigma). Target transcripts were detected with the primers GFP-F, 5'-CTTGACTTCAG-CACGTGTCTTGTAG-TTCCC-3' and GFP-R, 5'-AGAGGGTGAAGGTGATGCAACATACGG-3'; and actin transcripts were detected with the primers NbActin-F, 5'-CAGAAA-GAGGCTACTCTTTTACCACCACGG-3' and NbActin-R, 5'-GTGGTTTCAT-GAATGCCAGCA-GCTTCC-3'. The amplification threshold was set and $C_t$ values were calculated by OpticonMONITOR and Microsoft Excel. Triplicate leaf extracts representing infiltrated tissue from six plants were assayed and relative abundance of GFP RNA was calculated by dividing $0.5^{Ct\text{-}GFP}$ by $0.5^{Ct\text{-}actin}$.

2G12 Measurements

Antibody concentrations were measured by surface plasmon resonance as described previously using a BIACORE 2000 (Biacore; GE Healthcare; Rademacher et al., 2008). 2G12 accumulation was measured from triplicate leaf extracts representing infiltrated tissue from six plants.

Transmission Electron Microscopy

Extraction buffer was exchanged for TE (10 mM Tris-HCl, pH 7.5, 1 mM EDTA) using a 100-kD molecular mass cutoff column and eluted in the same volume as the initial sample loaded onto the column. Droplets were placed onto carbon-coated electron microscopy grids and left to settle for 60 s. After drawing off excess liquid, grids were negatively stained by placing them upside down onto droplets of 2% uranyl acetate, then washed three times on droplets of water. Imaging was performed using a JEOL 1200 transmission electron microscope at 80 kV.

ACKNOWLEDGMENTS

We would like to thank Markus Sack for help with 2G12 measurements and Kim Findlay for assistance with electron microscopy.

Received Jul. 11, 2008; accepted Sep. 2, 2008; published Sep. 5, 2008.

LITERATURE CITED

Ahlquist P, Schwartz M, Chen J B, Kushner D, Hao L H, Dye B T (2005) Viral and host determinants of RNA virus vector replication and expression. Vaccine 23: 1784-1787

Aricescu A R, Assenberg R, Bill R M, Busso D, Chang V T, Davis S J, Dubrovsky A, Gustafsson L, Hedfalk K, Heinemann U, et al (2006) Eukaryotic expression: developments for structural proteomics. Acta Crystallogr D Biol Crystallogr 62: 1114-1124

Buchacher A, Predl R, Strutzenberger K, Steinfellner W, Trkola A, Purtscher M, Gruber G, Tauer C, Steindl F, Jungbauer A, et al (1994) Generation of human monoclonal antibodies against HIV-1 proteins; electrofusion and Epstein-Barr virus transformation for peripheral blood lymphocyte immortalization. AIDS Res Hum Retroviruses 10: 359-369

Cañizares MC, Liu L, Perrin Y, Tsakiris E, Lomonossoff G P (2006) A bipartite system for the constitutive and inducible expression of high levels of foreign proteins in plants. Plant Biotechnol J 4: 183-193

Castro C, Arnold J J, Cameron C E (2005) Incorporation fidelity of the viral RNA-dependent RNA polymerase: a kinetic, thermodynamic and structural perspective. Virus Res 107: 141-149

Gamarnik A V, Andino R (1998) Switch from translation to RNA replication in a positive-stranded RNA virus. Genes Dev 12: 2293-2304

Giritch A, Marillonnet S, Engler C, van Eldik G, Botterman J, Klimyuk V Gleba Y (2006) Rapid high-yield expression of full-size IgG antibodies in plants coinfected with noncompeting viral vectors. Proc Natl Acad Sci USA 103: 14701-14706

Holness C L, Lomonossoff G P, Evans D, Maule A J (1989) Identification of the initiation codons for translation of cowpea mosaic-virus middle component RNA using site-directed mutagenesis of an infectious cDNA clone. Virology 172: 311-320

Lindbo J A (2007) TRBO: a high-efficiency tobacco mosaic virus RNA-Based overexpression vector. Plant Physiol 145: 1232-1240

Liu L, Cañizares MC, Monger W, Perrin Y, Tsakiris E, Porta C, Shariat N Nicholson L, Lomonossoff G P (2005) Cowpea mosaic virus-based systems for the production of antigens and antibodies in plants. Vaccine 23: 1788-1792

Ma J K C, Drake P M W, Christou P (2003) The production of recombinant pharmaceutical proteins in plants. Nat Rev Genet 4: 794-805

Mechtcheriakova I A, Eldarov M A, Nicholson L, Shanks M, Skryabin K G, Lomonossoff G P (2006) The use of viral vectors to produce hepatitis B virus core particles in plants. J Virol Methods 131: 10-15

Morris D R, Geballe A P (2000) Upstream open reading frames as regulators of mRNA translation. Mol Cell Biol 20: 8635-8642

Pruss G, Ge X, Shi X M, Carrington J C, Vance V (1997) Plant viral synergism: the potyviral genome encodes a broad-range pathogenicity enhancer that transactivates replication of heterologous viruses. Plant Cell 9: 859-868

Rademacher T, Sack M, Arcalis E, Stadlmann J, Balzer S, Altmann F, Quendler H, Stiegler G, Kunert R, Fischer R, et al (2008) Recombinant antibody 2G12 produced in maize endosperm efficiently neutralizes HIV-1 and contains predominantly single-GcNAc N-glycans. Plant Biotechnol J 6: 189-201

Richards H A, Halfhill M D, Millwood R J, Stewart C N Jr (2003) Quantitative GFP fluorescence as an indicator of recombinant protein synthesis in transgenic plants. Plant Cell Rep 22:117-121

Rohll J B, Holness C L, Lomonossoff G P, Maule A J (1993) 3'-Terminal nucleotide sequences important for the accumulation of cowpea mosaic virus M-RNA. Virology 193: 672-679

Ryabova L A, Pooggin M M, Hohn T (2006) Translation reinitiation and leaky scanning in plant viruses. Virus Res 119: 52-62

Sainsbury F, Cañizares MC, Lomonossoff G P (2007) Cowpea mosaic virus-based expression vectors. In K Hefferon, ed, Virus Expression Vectors. Transworld Research Network, Kerala, India, pp 339-555

Sainsbury F, Lavoie P O, D'Aoust M A, Vezina L P, Lomonossoff G P (2008a) Expression of multiple proteins using full-length and deleted versions of cowpea mosaic virus RNA-2. Plant Biotechnol J 6: 82-92

Sainsbury F, Liu L, Lomonossoff G P (2008b) Cowpea mosaic virus-based expression of antigens and antibodies in plants. In L Faye, V Gomord, eds, Methods in Biotechnology: Recombinant Pharmaceutical Proteins from Plants. Humana Press, NY (in press)

Twyman R M, Stoger E, Schillberg S, Christou P, Fischer R (2003) Molecular farming in plants: host systems and expression technology. Trends Biotechnol 21: 570-578 van Bokhoven H, Le Gall O, Kasteel D, Verver J, Wellink J, van Kammen A B (1993) Cis- and trans-acting elements in cowpea mosaic virus RNA replication. Virology 195: 377-386 van Engelen F A, Molthoff J W, Conner A J, Nap J P, Pereira A, Stiekema W J (1995) pBINPLUS: an improved plant transformation vector based on pBIN19. Transgenic Res 4: 288-290

Voinnet O, Rivas S, Mestre P, Baulcombe D (2003) An enhanced transient expression system in plants based on suppression of gene silencing by the p19 protein of tomato bushy stunt virus. Plant J 33: 949-956

Wellink J, van Lent J W M, Verver J, Sijen T, Goldbach R W, van Kammen A B (1993a) The cowpea mosaic virus M RNA-encoded 48-kilodalton protein is responsible for induction of tubular structures in protoplasts. J Virol 67: 3660-3664

Wellink J, Verver J, van Kammen A (1993b) Mutational analysis of AUG codons of Cowpea Mosaic Virus-M RNA. Biochimie 75: 741-747

Yin J, Li G, Ren X, Herrer G (2007) Select what you need: a comparative evaluation of the advantages and limitations of frequently used expression systems for foreign genes. J Biotechnol 127:335-347

---

The invention claimed is:

1. A method for expressing a protein heterologous to Cowpea Mosaic Virus (CPMV) in a plant comprising: introducing a gene expression construct into a plant cell of the plant, said gene expression construct comprising from 5' to 3':
   (i) an enhancer sequence comprising a nucleic acid sequence comprising a mutated sequence of SEQ ID NO:1 starting with nucleotide 1 of SEQ ID NO:1 and up to target initiation site at positions 161-163, wherein the mutated sequence of SEQ ID NO:1 consists essentially of mutations at the initiation site of positions 115-117 and at the target initiation site at positions 161-163, and wherein neither of the two mutated initiation sites functions as a translational initiation site, and
   (ii) a coding sequence for the heterologous protein;
   wherein mutations at the initiation site of positions 115-117 and at the target initiation site at positions 161-163 comprise deletion, insertion, substitution or removal of the target initiation site, wherein the coding sequence is operably linked to a functional translation initiation site and is after the mutated target initiation site,
   wherein the heterologous protein is expressed in the plant, and wherein the expression of the heterologous protein is enhanced in comparison with expression of the heterologous protein from a construct comprising the unmutated nucleic acid sequence of SEQ ID NO:1 having a functional target initiation site at positions 161-163 and having a functional initiation site at positions 115-117.

2. The method of claim 1, wherein the codon of positions 115-117 of SEQ ID NO:1 is GUG.

3. The method of claim 2, further comprising introducing into the plant cell a heterologous suppressor of gene silencing.

4. The method of claim 3, further comprising harvesting the heterologous protein.

5. The method of claim 4 further comprising preparing an extract of the heterologous protein.

6. The method of claim 1, further comprising introducing into the plant cell a heterologous suppressor of gene silencing.

7. The method of claim 6, further comprising harvesting the heterologous protein.

8. The method of claim 7 further comprising preparing an extract of the heterologous protein.

9. The method of claim 1, further comprising harvesting the heterologous protein.

10. The method of claim 9 further comprising preparing an extract of the heterologous protein.

11. A gene expression construct comprising from 5' to 3':
    (i) an enhancer sequence comprising a nucleic acid sequence comprising a mutated sequence of SEQ ID NO:1 starting with nucleotide 1 of SEQ ID NO:1 and up to target initiation site at positions 161-163, wherein the mutated sequence of SEQ ID NO:1 consists essentially of mutations at the initiation site of positions 115-117 and at the target initiation site at positions 161-163, and wherein neither of the two mutated initiation sites functions as a translational initiation site,
    (ii) a coding sequence for a protein heterologous to CPMV,
    and wherein the coding sequence is operably linked to a functional translation initiation site and is after the mutated target initiation site, wherein the heterologous protein is expressed in a plant,
    and wherein the expression of the heterologous protein is enhanced in comparison with expression of the heterologous protein from a construct comprising the unmutated nucleic acid sequence of SEQ ID NO:1 having a functional target initiation site at positions 161-163 and having a functional initiation site at positions 115-117.

12. The gene expression construct of claim 11, wherein the codon of positions 115-117 of SEQ ID NO:1 is GUG.

13. The method of any one of claims 1, 6, 9, 7, 10, or 8, wherein the target initiation site is deleted.

* * * * *

SEQUENCE LISTING

```
<160> NUMBER OF SEQ ID NOS: 37

<210> SEQ ID NO 1
<211> LENGTH: 3481
<212> TYPE: DNA
<213> ORGANISM: Cowpea mosaic virus

<400> SEQUENCE: 1
tattaaaatc ttaataggtt ttgataaaag cgaacgtggg gaaacccgaa ccaaaccttc      60
ttctaaattc tctctcatct ctcttaaagc aaacttctct cttgtctttc ttgcatgagc     120
gatcttcaac gttgtcagat cgtgcttcgg caccagtaca atgttttctt tcactgaagc     180
gaaatcaaag atctctttgt ggacacgtag tgcggcgcca ttaaataacg tgtacttgtc     240
ctattcttgt cggtgtggtc ttgggaaaag aaagcttgct ggaggctgct gttcagcccc     300
atacattact tgttacgatt ctgctgactt tcggcgggtg caatatctct acttctgctt     360
gacgaggtat tgttgcctgt acttctttct tcttcttctt gctgattggt tctataagaa     420
atctagtatt ttctttgaaa cagagttttc ccgtggtttt cgaacttgga gaaagattgt     480
taagcttctg tatattctgc ccaaatttga aatggaaagc attatgagcc gtggtattcc     540
ttcaggaatt ttggaggaaa aagctattca gttcaaacgt gccaaagaag gaataaaacc     600
cttgaaggat gagattccca agcctgagga tatgtatgtg tctcacactt ctaaatggaa     660
tgtgctcaga aaaatgagcc aaaagactgt ggatctttcc aaagcagctg ctgggatggg     720
attcatcaat aagcatatgc ttacgggcaa catcttggca caaccaacaa cagtcttgga     780
tattcccgtc acaaaggata aaacacttgc gatggccagt gattttattc gtaaggagaa     840
tctcaagact tctgccattc acattggagc aattgagatt attatccaga gctttgcttc     900
ccctgaaagt gatttgatgg gaggcttttt gcttgtggat tctttacaca ctgatacagc     960
taatgctatt cgtagcattt ttgttgctcc aatgcgggga ggaagaccag tcagagtggt    1020
```

-continued

```
gaccttccca aatacactgg cacctgtatc atgtgatctg aacaatagat tcaagctcat    1080
ttgctcattg ccaaactgtg atattgtcca gggtagccaa gtagcagaag tgagtgtaaa    1140
tgttgcagga tgtgctactt ccatagagaa atctcacacc ccttcccaat tgtatacaga    1200
ggaatttgaa aaggagggtg ctgttgttgt agaatactta ggcagacaga cctattgtgc    1260
tcagcctagc aatttaccca cagaagaaaa acttcggtcc cttaagtttg actttcatgt    1320
tgaacaacca agtgtcctga agttatccaa ttcctgcaat gcgcactttg tcaagggaga    1380
aagtttgaaa tactctattt ctggcaaaga agcagaaaac catgcagttc atgctactgt    1440
ggtctctcga aaggggcttc tgcggcacc caagcaatat gatcctattt tgggacgggt    1500
gctggatcca cgaaatggga atgtggcttt tccacaaatg gagcaaaact tgtttgccct    1560
ttctttggat gatacaagct cagttcgtgg ttctttgctt gacacaaaat tcgcacaaac    1620
tcgagttttg ttgtccaagg ctatggctgg tggtgatgtg ttattggatg agtatctcta    1680
tgatgtggtc aatggacaag attttagagc tactgtcgct ttttgcgca cccatgttat    1740
aacaggcaaa ataaaggtga cagctaccac caacatttct gacaactcgg gttgttgttt    1800
gatgttggcc ataaatagtg gtgtgagggg taagtatagt actgatgttt atactatctg    1860
ctctcaagac tccatgacgt ggaacccagg gtgcaaaaag aacttctcgt tcacatttaa    1920
tccaaaccct tgtggggatt cttggtctgc tgagatgata agtcgaagca gagttaggat    1980
gacagttatt tgtgtttcgg gatggacctt atctcctacc acagatgtga ttgccaagct    2040
agactggtca attgtcaatg agaaatgtga gcccaccatt taccacttgg ctgattgtca    2100
gaattggtta cccctaatc gttggatggg aaaaattgact tttccccagg gtgtgacaag    2160
tgaggttcga aggatgcctc tttctatagg aggcggtgct ggtgcgactc aagctttctt    2220
ggccaatatg cccaattcat ggatatcaat gtggagatat tttagaggtg aacttcactt    2280
tgaagttact aaaatgagct ctccatatat taaagccact gttacatttc tcatagcttt    2340
tggtaatctt agtgatgcct ttggttttta tgagagtttt cctcatagaa ttgttcaatt    2400
tgctgaggtt gaggaaaaat gtactttggt tttctcccaa caagagtttg tcactgcttg    2460
gtcaacacaa gtaaacccca gaaccacact tgaagcagat ggttgtccct acctatatgc    2520
aattattcat gatagtacaa caggtacaat ctccggagat tttaatcttg gggtcaagct    2580
tgttggcatt aaggattttt gtggtatagg ttctaatccg ggtattgatg gttcccgctt    2640
gcttggagct atagcacaag gacctgtttg tgctgaagcc tcagatgtgt atagcccatg    2700
tatgatagct agcactcctc ctgctccatt ttcagacgtt acagcagtaa cttttgactt    2760
aatcaacggc aaaataactc ctgttggtga tgacaattgg aatacgcaca tttataatcc    2820
tccaattatg aatgtcttgc gtactgctgc ttggaaatct ggaactattc atgttcaact    2880
taatgttagg ggtgctggtg tcaaaagagc agattgggat ggtcaagtct tgtttaccct    2940
gcgccagtcc atgaaccctg aaagttatga tgcgcggaca tttgtgatct cacaacctgg    3000
ttctgccatg ttgaacttct cttttgatat catagggccg aatagcggat ttgaatttgc    3060
cgaaagccca tgggccaatc agaccacctg gtatcttgaa tgtgttgcta ccaatcccag    3120
acaaatacag caatttgagg tcaacatgcg cttcgatcct aatttcaggg ttgccggcaa    3180
tatcctgatg ccccatttc cactgtcaac ggaaactcca ccgttattaa agtttaggtt    3240
tcgggatatt gaacgctcca agcgtagtgt tatggttgga cacactgcta ctgctgctta    3300
actctggttt cattaaattt tctttagttt gaatttactg ttatttggtg tgcatttcta    3360
tgtttggtga gcggttttct gtgctcagag tgtgtttatt ttatgtaatt taatttcttt    3420
```
gtgagctcct gtttagcagg tcgtcccttc agcaaggaca caaaaagatt ttaattttat 3480
t 3481

<210> SEQ ID NO 2
<211> LENGTH: 31
<212> TYPE: DNA
<213> ORGANISM: Artificial sequence
<220> FEATURE:
<223> OTHER INFORMATION: Synthetic sequence: Oligonucleotide A115G-F

<400> SEQUENCE: 2
cttgtctttc ttgcgtgagc gatcttcaac g 31

<210> SEQ ID NO 3
<211> LENGTH: 31
<212> TYPE: DNA
<213> ORGANISM: Artificial sequence
<220> FEATURE:
<223> OTHER INFORMATION: Synthetic sequence: Oligonucleotide A115G-R

<400> SEQUENCE: 3
cgttgaagat cgctcacgca agaaagacaa g 31

<210> SEQ ID NO 4
<211> LENGTH: 33
<212> TYPE: DNA
<213> ORGANISM: Artificial sequence
<220> FEATURE:
<223> OTHER INFORMATION: Synthetic sequence: Oligonucleotide U162C-F

<400> SEQUENCE: 4
ggcaccagta caacgttttc tttcactgaa gcg 33

<210> SEQ ID NO 5
<211> LENGTH: 33
<212> TYPE: DNA
<213> ORGANISM: Artificial sequence
<220> FEATURE:
<223> OTHER INFORMATION: Synthetic sequence: Oligonucleotide U162C-R

<400> SEQUENCE: 5
cgcttcagtg aaagaaaacg ttgtactggt gcc 33

<210> SEQ ID NO 6
<211> LENGTH: 50
<212> TYPE: DNA
<213> ORGANISM: Cowpea mosaic virus

<400> SEQUENCE: 6
tatattctgc ccaaatttga aatggaaagc attatgagcc gtggtattcc 50

<210> SEQ ID NO 7
<211> LENGTH: 50
<212> TYPE: DNA
<213> ORGANISM: Artificial sequence
<220> FEATURE:
<223> OTHER INFORMATION: Synthetic sequence: Mutated sequence in
pM81-FSC-1

<400> SEQUENCE: 7
tatattctgc ccaaatttgt catgaaaagc attatgagcc gtggtattcc 50

<210> SEQ ID NO 8
<211> LENGTH: 42

```
<212> TYPE: DNA
<213> ORGANISM: Artificial sequence
<220> FEATURE:
<223> OTHER INFORMATION: Synthetic sequence: Mutated sequence in
      pM81-FSC-2

<400> SEQUENCE: 8
tatattctgc ccaaattcgc gacgatcgta ctctcgaggc ct                         42

<210> SEQ ID NO 9
<211> LENGTH: 7732
<212> TYPE: DNA
<213> ORGANISM: Artificial sequence
<220> FEATURE:
<223> OTHER INFORMATION: Synthetic sequence: pM81-FSC-1

<400> SEQUENCE: 9
ttaattaaga attcgagctc caccgcggaa acctcctcgg attccattgc ccagctatct     60
gtcactttat tgagaagata gtggaaaagg aaggtggctc ctacaaatgc catcattgcg    120
ataaaggaaa ggccatcgtt gaagatgcct ctgccgacag tggtcccaaa gatggacccc    180
cacccacgag gagcatcgtg gaaaagaag acgttccaac cacgtcttca agcaagtgg     240 attgatgtga tatctccact gacgtaaggg atgacgcaca atcccactat ccttcgcaag    300
acccttcctc tatataagga agttcatttc atttggagag gtattaaaat cttaataggt    360
tttgataaaa gcgaacgtgg ggaaacccga accaaacctt cttctaaact ctctctcatc    420
tctcttaaag caaacttctc tcttgtcttt cttgcatgag cgatcttcaa cgttgtcaga    480
tcgtgcttcg gcaccagtac aatgttttct ttcactgaag cgaaatcaaa gatctctttg    540
tggacacgta gtgcggcgcc attaaataac gtgtacttgt cctattcttg tcggtgtggt    600
cttgggaaaa gaaagcttgc tggaggctgc tgttcagccc catacattac ttgttacgat    660
tctgctgact ttcggcgggt gcaatatctc tacttctgct tgacgaggta ttgttgcctg    720
tacttctttc ttcttcttct tgctgattgg ttctataaga aatctagtat tttcttttgaa   780 acagagtttt cccgtggttt tcgaacttgg agaaagattg ttaagcttct gtatattctg    840
cccaaatttg tcatgaaaag cattatgagc cgtggtattc cttcaggaat tttggaggaa    900
aaagctattc agttcaaacg tgccaaagaa gggaataaac ccttgaagga tgagattccc    960
aagcctgagg atatgtatgt gtctcacact tctaaatgga atgtgctcag aaaaatgagc   1020
caaaagactg tggatctttc caaagcagct gctgggatgg gattcatcaa taagcatatg   1080
cttacgggca acatcttggc acaaccaaca acagtcttgg atattcccgt cacaaaggat   1140
aaaacacttg cgatggccag tgattttatt cgtaaggaga atctcaagac ttctgccatt   1200
cacattggag caattgagat tattatccag agctttgctt ccctgaaag tgatttgatg    1260 ggaggctttt tgcttgtgga ttctttacac actgatacag ctaatgctat tcgtagcatt    1320
tttgttgctc caatgcgggg aggaagacca gtcagagtgg tgaccttccc aaatacactg    1380
gcacctgtat tatgtgatct gaacaataga ttcaagctca tttgctcatt gccaaactgt    1440
gatattgtcc agggtagcca agtagcagaa gtgagtgtaa atgttgcagg atgtgctact    1500
tccatagaga aatctcacac ccttcccaa ttgtatacag aggaatttga aaggagggt     1560 gctgttgttg tagaatactt aggcagacag acctattgtg ctcagcctag caatttaccc    1620
acagaagaaa aacttcggtc ccttaagttt gactttcatg ttgaacaacc aagtgtcctg    1680
aagttatcca attcctgcaa tgcgcacttt gtcaaggaa aaagtttgaa atactctatt   1740
tctggcaaag aagcagaaaa ccatgcagtt catgctactg tggtctctcg agaaggggct   1800
```

```
tctgcggcac ccaagcaata tgatcctatt ttgggacggg tgctggatcc acgaaatggg   1860
aatgtggctt ttccacaaat ggagcaaaac ttgtttgccc tttctttgga tgatacaagc   1920
tcagttcgtg gttctttgct tgacacaaaa ttcgcacaaa ctcgagtttt gttgtccaag   1980
gctatggctg tggtgatgt gttattggat gagtatctct atgatgtggt caatggacaa    2040
gattttagag ctactgtcgc ttttttgcgc acccatgtta taacaggcaa aataaaggtg   2100
acagctacca ccaacatttc tgacaactcg ggttgttgtt tgatgttggc cataaatagt   2160
ggtgtgaggg gtaagtatag tactgatgtt tatactatct gctctcaaga ctccatgacg   2220
tggaacccag ggtgcaaaaa gaacttctcg ttcacattta atccaaaccc ttgtggggat   2280
tcttggtctg ctgagatgat aagtcgaagc agagttagga tgacagttat ttgtgtttcg   2340
ggatggacct tatctcctac cacagatgtg attgccaagc tagactggtc aattgtcaat   2400
gagaaatgtg agcccaccat ttaccacttg gctgattgtc agaattggtt accccttaat   2460
cgttggatgg gaaaattgac ttttccccag ggtgtgacaa gtgaggttcg aaggatgcct   2520 cttctatag gaggcggtgc tggtgcgact caagctttct tggccaatat gcccaattca    2580
tggatatcaa tgtggagata ttttagaggt gaacttcact ttgaagttac taaaatgagc   2640
tctccatata ttaaagccac tgttacattt ctcatagctt ttggtaatct tagtgatgcc   2700
tttggttttt atgagagttt tcctcataga attgttcaat ttgctgaggt tgaggaaaaa   2760
tgtactttgg ttttctccca caagagtttt gtcactgctt ggtcaacaca agtaaacccc   2820
agaaccacac ttgaagcaga tggttgtccc tacctatatg caattattca tgatagtaca   2880
acaggtacaa tctccggaga ttttatcttg gggtcaagct tgttggcatt aaggattttt   2940
gtggtatagg ttctaatccg ggtattgatg gttcccgctt gcttggagct atagcacaag   3000
gacctgtttg tgctgaagcc tcagatgtgt atagcccatg tatgatagct agcactcctc   3060
ctgctccatt ttcagacgtc acagcagtaa actttgact taatcaacgg caaataact    3120 cctgttggtg atgacaattg gaatacgcac atttataatc ctccaattat gaatgtcttg   3180
cgtactgctg cttggaaatc tggaactatt catgttcaac ttaatgttag gggtgctggt   3240
gtcaaaagag cagattggga tggtcaagtc tttgtttacc tgcgccagtc catgaaccct   3300
gaaagttatg atgcgcggac atttgtgatc tcacaacctg gttctgccat gttgaacttc   3360
tcttttgata tcatagggcc gaatagcgga tttgaatttg ccgaaagccc atgggccaat   3420
cagaccacct ggtatcttga atgtgttgct accaatccca gacaaataca gcaatttgag   3480
gtcaacatgc gcttcgatcc taatttcagg gttgccggca atatcctgat gccccccattt  3540 ccactgtcaa cggaaactcc accgttatta aagtttaggt ttcgggatat tgaacgctcc   3600
aagcgtagtg ttatggttgg acacactgct actgctgcag cgcctgcaaa acagctctta   3660
aactttgacc tacttaagtt agcaggtgac gttgagtcca accctgggcc cagtaaagga   3720
gaagaacttt tcactggagt tgtcccaatt cttgttgaat tagatggtga tgttaatggg   3780
cacaaatttt ctgtcagtgg agagggtgaa ggtgatgcaa catacggaaa acttacccctt  3840 aaatttattt gcactactgg aaaactacct gttccatggc caacacttgt cactactttc   3900
tcttatggtg ttcaatgctt ttcaagatac ccagatcata tgaaacggca tgactttttc   3960
aagagtgcca tgcccgaagg ttatgtacag gaaagaacta tattttcaa ggatgacggg    4020 aactacaaga cacgtgctga agtcaagttt gaaggtgata cccttgttaa tagaatcgag   4080
ttaaaaggta ttgattttaa agaagatgga aacattcttg gacacaaatt ggaatacaac   4140
```

```
tataactcac acaatgtata catcatggca gacaaacaaa agaatggaat caaagttaac    4200
ttcaaaatta gacacaacat tgaagatgga agcgttcaac tagcagacca ttatcaacaa    4260
aatactccaa ttggcgatgg ccctgtcctt ttaccagaca accattacct gtccacacaa    4320
tctgcccttt cgaaagatcc caacgaaaag agagaccaca tggtccttct tgagtttgta    4380
acagctgctg ggattacaca tggcatggat gaactataca aataaaggcc tttaactctg    4440
gtttcattaa attttctttta gtttgaattt actgttattc ggtgtgcatt tctatgtttg    4500
gtgagcggtt ttctgtgctc agagtgtgtt tattttatgt aatttaattt ctttgtgagc    4560
tcctgtttag caggtcgtcc cttcagcaag gacacaaaaa gatttttaatt ttattaaaaa    4620
aaaaaaaaaa aaagaccggg aattcgatat caagcttatc gacctgcaga tcgttcaaac    4680
atttggcaat aaagtttctt aagattgaat cctgttgccg gtcttgcgat gattatcata    4740
taatttctgt tgaattacgt taagcatgta ataattaaca tgtaatgcat gacgttattt    4800
atgagatggg ttttatgat tagagtcccg caattataca tttaatacgc gatagaaaac    4860
aaaatatagc gcgcaaacta ggataaatta tcgcgcgcgg tgtcatctat gttactagat    4920
ctctagagtc tcaagcttgg cgcgccagct gcattaatga atcggccaac gcgcggggag    4980
aggcggtttg cgtattgggc gctcttccgc ttcctcgctc actgactcgc tgcgctcggt    5040
cgttcggctg cggcgagcgg tatcagctca ctcaaaggcg gtaatacggt tatccacaga    5100
atcaggggat aacgcaggaa agaacatgtg agcaaaaggc cagcaaaagg ccaggaaccg    5160
taaaaaggcc gcgttgctgg cgtttttcca taggctccgc cccctgacg agcatcacaa    5220
aaatcgacgc tcaagtcaga ggtggcgaaa cccgacagga ctataaagat accaggcgtt    5280
tccccctgga agctccctcg tgcgctctcc tgttccgacc ctgccgctta ccggatacct    5340
gtccgccttt ctcccttcgg gaagcgtggc gctttctcat agctcacgct gtaggtatct    5400
cagttcggtg taggtcgttc gctccaagct gggctgtgtg cacgaacccc ccgttcagcc    5460
cgaccgctgc gccttatccg gtaactatcg tcttgagtcc aacccggtaa gacacgactt    5520
atcgccactg gcagcagcca ctggtaacag gattagcaga gcgaggtatg taggcggtgc    5580
tacagagttc ttgaagtggt ggcctaacta cggctacact agaagaacag tatttggtat    5640
ctgcgctctg ctgaagccag ttaccttcgg aaaaagagtt ggtagctctt gatccggcaa    5700
acaaaccacc gctggtagcg tggtttttt tgtttgcaag cagcagatta cgcgcagaaa    5760
aaaaggatct caagaagatc ctttgatctt ttctacgggg tctgacgctc agtggaacga    5820
aaactcacgt taagggattt tggttatgag attatcaaaa aggatcttca cctagatcct    5880
tttaaattaa aaatgaagtt ttaaatcaat ctaaagtata tatgagtaaa cttggtctga    5940
cagttaccaa tgcttaatca gtgaggcacc tatctcagcg atctgtctat ttcgttcatc    6000
catagttgcc tgactccccg tcgtgtagat aactacgata cgggagggct taccatctgg    6060
ccccagtgct gcaatgatac cgcgagaccc acgctcaccg gctccagatt tatcagcaat    6120
aaaccagcca gccggaaggg ccgagcgcag aagtggtcct gcaactttat ccgcctccat    6180
ccagtctatt aattgttgcc gggaagctag agtaagtagt tcgccagtta atagtttgcg    6240
caacgttgtt gccattgcta caggcatcgt ggtgtcacgc tcgtcgtttg gtatggcttc    6300
attcagctcc ggttcccaac gatcaaggcg agttacatga tcccccatgt tgtgcaaaaa    6360
agcggttagc tccttcggtc ctccgatcgt tgtcagaagt aagttggccg cagtgttatc    6420
actcatggtt atggcagcac tgcataattc tcttactgtc atgccatccg taagatgctt    6480
ttctgtgact ggtgagtact caaccaagtc attctgagaa tagtgtatgc ggcgaccgag    6540
```

```
ttgctcttgc ccggcgtcaa tacgggataa taccgcgcca catagcagaa ctttaaaagt    6600
gctcatcatt ggaaaacgtt cttcggggcg aaaactctca aggatcttac cgctgttgag    6660
atccagttcg atgtaaccca ctcgtgcacc caactgatct tcagcatctt ttactttcac    6720
cagcgtttct gggtgagcaa aaacaggaag gcaaaatgcc gcaaaaaagg gaataagggc    6780
gacacggaaa tgttgaatac tcatactctt ccttttcaa tattattgaa gcatttatca     6840
gggttattgt cttatgagcg gatacatatt tgaatgtatt tagaaaaata aacaaatagg    6900
ggttccgcgc acatttcccc gaaaagtgcc acctaaattg taagcgttaa tattttgtta    6960
aaattcgcgt taaattttg ttaaatcagc tcatttttta accataggc cgaaatcggc      7020 aaaatccctt ataaatcaaa agaatagacc gagataggt tgagtgttgt tccagtttgg     7080
aacaagagtc cactattaaa gaacgtggac tccaacgtca aagggcgaaa aaccgtctat    7140
cagggcgatg gcccactacg tgaaccatca ccctaatcaa gttttttggg gtcgaggtgc    7200
cgtaaagcac taaatcggaa ccctaaaggg agcccccgat ttagagcttg acggggaaag    7260
ccggcgaacg tggcgagaaa ggaagggaag aaagcgaaag gagcgggcgc tagggcgctg    7320
gcaagtgtag cggtcacgct gcgcgtaacc accacaccccg ccgcgcttaa tgcgccgcta   7380
cagggcgcgt cccattcgcc attcaggctg cgcaactgtt gggaagggcg atcggtgcgg    7440
gcctcttcgc tattacgcca gctggcgaaa ggggatgtg ctgcaaggcg attaagttgg    7500
gtaacgccag ggttttccca gtcacgacgt tgtaaaacga cggccagtga gtactttggc    7560
gtaatcatgg tcatagctgt ttcctgtgtg aaattgttat ccgctcacaa ttccacacaa    7620
catacgagcc ggaagcataa agtgtaaagc ctggggtgcc taatgagtga gctaactcac    7680
attaattgcg ttgcgctcac tgcccgcttt ccagtcggga aacctggcgc gc            7732

<210> SEQ ID NO 10
<211> LENGTH: 4173
<212> TYPE: DNA
<213> ORGANISM: Artificial sequence
<220> FEATURE:
<223> OTHER INFORMATION: Synthetic sequence: pM81-FSC-2

<400> SEQUENCE: 10
tattaaaatc ttaataggtt ttgataaaag cgaacgtggg gaaacccgaa ccaaaccttc     60
ttctaaactc tctctcatct ctcttaaagc aaacttctct cttgtctttc ttgcatgagc    120
gatcttcaac gttgtcagat cgtgcttcgg caccagtaca atgttttctt tcactgaagc    180
gaaatcaaag atctctttgt ggacacgtag tgcggcgcca ttaaataacg tgtacttgtc    240
ctattcttgt cggtgtggtc ttgggaaaag aaagcttgct ggaggctgct gttcagcccc    300
atacattact tgttacgatt ctgctgactt tcggcgggtg caatatctct acttctgctt    360
gacgaggtat tgttgcctgt acttctttct tcttcttctt gctgattggt tctataagaa    420
atctagtatt ttctttgaaa cagagttttc ccgtggtttt cgaacttgga gaaagattgt    480
taagcttctg tatattctgc ccaaattcgc gacgatcgta ctctcgaggc ctttaactct    540
ggtttcatta aatttttctt tagtttgaatt tactgttatt cggtgtgcat ttctatgttt    600
ggtgagcggt tttctgtgct cagagtgtgt ttatttatg taatttaatt tctttgtgag    660 ctcctgtttta gcaggtcgtc ccttcagcaa ggacacaaaa agatttttaat tttattaaaa    720 aaaaaaaaaa aaaagaccgg gaattcgata tcaagcttat cgacctgcag atcgttcaaa    780
catttggcaa taaagtttct taagattgaa tcctgttgcc ggtcttgcga tgattatcat    840
```

```
ataatttctg ttgaattacg ttaagcatgt aataattaac atgtaatgca tgacgttatt    900
tatgagatgg gttttttatga ttagagtccc gcaattatac atttaatacg cgatagaaaa    960
caaaatatag cgcgcaaact aggataaatt atcgcgcgcg gtgtcatcta tgttactaga   1020
tctctagagt ctcaagcttg gcgcgccagc tgcattaatg aatcggccaa cgcgcgggga   1080
gaggcggttt gcgtattggg cgctcttccg cttcctcgct cactgactcg ctgcgctcgg   1140
tcgttcggct gcggcgagcg gtatcagctc actcaaaggc ggtaatacgg ttatccacag   1200
aatcagggga taacgcagga agaacatgt gagcaaaagg ccagcaaaag gccaggaacc   1260
gtaaaaaggc cgcgttgctg gcgttttttcc ataggctccg ccccctgac gagcatcaca   1320
aaaatcgacg ctcaagtcag aggtggcgaa acccgacagg actataaaga taccaggcgt   1380
ttccccctgg aagctccctc gtgcgctctc ctgttccgac cctgccgctt accggatacc   1440
tgtccgcctt tctcccttcg ggaagcgtgg cgctttctca tagctcacgc tgtaggtatc   1500
tcagttcggt gtaggtcgtt cgctccaagc tgggctgtgt gcacgaaccc cccgttcagc   1560
ccgaccgctg cgccttatcc ggtaactatc gtcttgagtc caacccggta agacacgact   1620
tatcgccact ggcagcagcc actggtaaca ggattagcag agcgaggtat gtaggcggtg   1680
ctacagagtt cttgaagtgg tggcctaact acggctacac tagaagaaca gtatttggta   1740
tctgcgctct gctgaagcca gttaccttcg gaaaaagagt tggtagctct tgatccggca   1800
aacaaaccac cgctggtagc ggtggttttt tgtttgcaa gcagcagatt acgcgcagaa   1860
aaaaaggatc tcaagaagat cctttgatct tttctacggg gtctgacgct cagtggaacg   1920
aaaactcacg ttaagggatt ttggttatga gattatcaaa aaggatcttc acctagatcc   1980
ttttaaatta aaaatgaagt tttaaatcaa tctaaagtat atatgagtaa acttggtctg   2040
acagttacca atgcttaatc agtgaggcac ctatctcagc gatctgtcta tttcgttcat   2100
ccatagttgc ctgactcccc gtcgtgtaga taactacgat acgggagggc ttaccatctg   2160
gccccagtgc tgcaatgata ccgcgagacc cacgctcacc ggctccagat ttatcagcaa   2220
taaaccagcc agccggaagg gccgagcgca gaagtggtcc tgcaacttta tccgcctcca   2280
tccagtctat taattgttgc cgggaagcta gagtaagtag ttcgccagtt aatagtttgc   2340
gcaacgttgt tgccattgct acaggcatcg tggtgtcacg ctcgtcgttt ggtatggctt   2400
cattcagctc cggttcccaa cgatcaaggc gagttacatg atccccatg ttgtgcaaaa   2460
aagcggttag ctccttcggt cctccgatcg ttgtcagaag taagttggcc gcagtgttat   2520
cactcatggt tatggcagca ctgcataatt ctcttactgt catgccatcc gtaagatgct   2580
tttctgtgac tggtgagtac tcaaccaagt cattctgaga atagtgtatg cggcgaccga   2640
gttgctcttg cccggcgtca atacgggata taccgcgcc acatagcaga actttaaaag   2700
tgctcatcat tggaaaacgt tcttcggggc gaaaactctc aaggatctta ccgctgttga   2760
gatccagttc gatgtaaccc actcgtgcac ccaactgatc ttcagcatct tttactttca   2820
ccagcgtttc tgggtgagca aaaacaggaa ggcaaaatgc cgcaaaaaag gaataagggc   2880
gacacggaaa atgttgaata ctcatactct tcctttttca atattattga agcatttatc   2940
agggttattg tcttatgagc ggatacatat ttgaatgtat ttagaaaaat aaacaaatag   3000
gggttccgcg cacatttccc cgaaaagtgc cacctaaatt gtaagcgtta atatttttgtt   3060
aaaattcgcg ttaaattttt gttaaatcag ctcattttttt aaccaatagg ccgaaatcgg   3120
caaaatccct tataaatcaa agaatagac cgagataggg ttgagtgttg ttccagtttg   3180
gaacaagagt ccactattaa agaacgtgga ctccaacgtc aaagggcgaa aaaccgtcta   3240
```

```
tcagggcgat ggcccactac gtgaaccatc accctaatca agttttttgg ggtcgaggtg      3300
ccgtaaagca ctaaatcgga accctaaagg gagcccccga tttagagctt gacggggaaa      3360
gccggcgaac gtggcgagaa aggaagggaa gaaagcgaaa ggagcgggcg ctagggcgct      3420
ggcaagtgta gcggtcacgc tgcgcgtaac caccacaccc gccgcgctta atgcgccgct      3480
acagggcgcg tcccattcgc cattcaggct gcgcaactgt tgggaagggc gatcggtgcg      3540
ggcctcttcg ctattacgcc agctggcgaa aggggggatgt gctgcaaggc gattaagttg      3600
ggtaacgcca gggttttccc agtcacgacg ttgtaaaacg acggccagtg agtactttgg      3660
cgtaatcatg gtcatagctg tttcctgtgt gaaattgtta tccgctcaca attccacaca      3720
acatacgagc cggaagcata aagtgtaaag cctggggtgc ctaatgagtg agctaactca      3780
cattaattgc gttgcgctca ctgcccgctt tccagtcggg aaacctggcc gcttaattaa      3840
gaattcgagc tccaccgcgg aaacctcctc ggattccatt gcccagctat ctgtcacttt      3900
attgagaaga tagtggaaaa ggaaggtggc tcctacaaat gccatcattg cgataaagga      3960
aaggccatcg ttgaagatgc ctctgccgac agtggtccca agatggaccc cccacccacg      4020
aggagcatcg tggaaaaaga agacgttcca accacgtctt caaagcaagt ggattgatgt      4080
gatatctcca ctgacgtaag ggatgacgca caatcccact atccttcgca agacccttcc      4140
tctatataag gaagttcatt tcatttggag agg                                  4173

<210> SEQ ID NO 11
<211> LENGTH: 69
<212> TYPE: DNA
<213> ORGANISM: Artificial Sequence
<220> FEATURE:
<223> OTHER INFORMATION: Synthetic sequence: Polylinker
<220> FEATURE:
<221> NAME/KEY: CDS
<222> LOCATION: (3)..(68)

<400> SEQUENCE: 11 tc gcg acc ggt atg cat cac cat cac cat cat ccc ggg cat cac cat        47
   Ala Thr Gly Met His His His His His His Pro Gly His His His
   1               5                   10                  15 cac cat cac tag ctc gag gcc t                                         69
His His His     Leu Glu Ala <210> SEQ ID NO 12
<211> LENGTH: 18
<212> TYPE: PRT
<213> ORGANISM: Artificial Sequence
<220> FEATURE:
<223> OTHER INFORMATION: Synthetic sequence: Polylinker

<400> SEQUENCE: 12

Ala Thr Gly Met His His His His His His Pro Gly His His His
1               5                   10                  15

His His

<210> SEQ ID NO 13
<211> LENGTH: 69
<212> TYPE: DNA
<213> ORGANISM: Artificial Sequence
<220> FEATURE:
<223> OTHER INFORMATION: Synthetic sequence: Polylinker

<400> SEQUENCE: 13
aggcctcgag ctagtgatgg tgatggtgat gcccgggatg atggtgatgg tgatgcatac      60
```

-continued cggtcgcga                                                          69

<210> SEQ ID NO 14
<211> LENGTH: 25
<212> TYPE: DNA
<213> ORGANISM: Artificial sequence
<220> FEATURE:
<223> OTHER INFORMATION: Synthetic sequence: Oligonucleotide pBD-LB-F

<400> SEQUENCE: 14
gccactcagc ttcctcagcg gcttt                                        25

<210> SEQ ID NO 15
<211> LENGTH: 39
<212> TYPE: DNA
<213> ORGANISM: Artificial sequence
<220> FEATURE:
<223> OTHER INFORMATION: Synthetic sequence: Oligonucleotide
      pBD-RB-ApaI-R

<400> SEQUENCE: 15
tattagggcc cccggcgcca gatctgggga accctgtgg                         39

<210> SEQ ID NO 16
<211> LENGTH: 42
<212> TYPE: DNA
<213> ORGANISM: Artificial sequence
<220> FEATURE:
<223> OTHER INFORMATION: Synthetic sequence: Oligonucleotide
      pBD-ColEI-ApaI-F

<400> SEQUENCE: 16
gacttagggc ccgtccattt ccgcgcagac gatgacgtca ct                     42

<210> SEQ ID NO 17
<211> LENGTH: 45
<212> TYPE: DNA
<213> ORGANISM: Artificial sequence
<220> FEATURE:
<223> OTHER INFORMATION: Synthetic sequence: Oligonucleotide
      pBD-TrfA-SpeI-R

<400> SEQUENCE: 17
gcattaacta gtcgctggct gctgaacccc cagccggaac tgacc                  45

<210> SEQ ID NO 18
<211> LENGTH: 33
<212> TYPE: DNA
<213> ORGANISM: Artificial sequence
<220> FEATURE:
<223> OTHER INFORMATION: Synthetic sequence: Oligonucleotide
      pBD-oriV-SpeI-F

<400> SEQUENCE: 18
gtagcactag tgtacatcac cgacgagcaa ggc                               33

<210> SEQ ID NO 19
<211> LENGTH: 38
<212> TYPE: DNA
<213> ORGANISM: Artificial sequence
<220> FEATURE:
<223> OTHER INFORMATION: Synthetic sequence: Oligonucleotide
      pBD-oriV-AhdI-R

<400> SEQUENCE: 19
cagtagacag gctgtctcgc ggccgagggg cgcagccc                          38

<210> SEQ ID NO 20
<211> LENGTH: 77
<212> TYPE: DNA
<213> ORGANISM: Artificial sequence
<220> FEATURE:
<223> OTHER INFORMATION: Synthetic sequence: Oligonucleotide pMini>pMicr
      oBIN-F2

<400> SEQUENCE: 20
ggccggccac gcgttatctg cagagcgatc gcgaattgtg agcggataac aatttcacac      60
aggaaacagc tatgacc                                                    77

<210> SEQ ID NO 21
<211> LENGTH: 77
<212> TYPE: DNA
<213> ORGANISM: Artificial sequence
<220> FEATURE:
<223> OTHER INFORMATION: Synthetic sequence: Oligonucleotide pMini>pMicr
      oBIN-R

<400> SEQUENCE: 21
gcgatcgctc tgcagataac gcgtggccgg ccctcactgg tgaaagaaa aaccacccca       60 gtacattaaa aacgtcc                                                    77

<210> SEQ ID NO 22
<211> LENGTH: 36
<212> TYPE: DNA
<213> ORGANISM: Artificial sequence
<220> FEATURE:
<223> OTHER INFORMATION: Synthetic sequence: Oligonucleotide
      35SP19-PacI-F

<400> SEQUENCE: 22
ttaattaaga attcgagctc ggtaccccccc tactcc                              36

<210> SEQ ID NO 23
<211> LENGTH: 40
<212> TYPE: DNA
<213> ORGANISM: Artificial sequence
<220> FEATURE:
<223> OTHER INFORMATION: Synthetic sequence: Oligonucleotide
      35SP19-AscI-R

<400> SEQUENCE: 23
ggcgcgccat cttttatctt tagagttaag aactctttcg                           40

<210> SEQ ID NO 24
<211> LENGTH: 29
<212> TYPE: DNA
<213> ORGANISM: Artificial sequence
<220> FEATURE:
<223> OTHER INFORMATION: Synthetic sequence: Oligonucleotide
      35SP19-FseI-F

<400> SEQUENCE: 24
ggccggccga attcgagctc ggtaccccc                                       29

<210> SEQ ID NO 25
<211> LENGTH: 30
<212> TYPE: DNA
<213> ORGANISM: Artificial sequence
<220> FEATURE:
<223> OTHER INFORMATION: Synthetic sequence: Oligonucleotide
      35SP19-FseI-R

<400> SEQUENCE: 25
ggccggccat cttttatctt tagagttaag                                     30

<210> SEQ ID NO 26
<211> LENGTH: 40
<212> TYPE: DNA
<213> ORGANISM: Artificial sequence
<220> FEATURE:
<223> OTHER INFORMATION: Synthetic sequence: Oligonucleotide
      pBD-NPTII-FseI-F

<400> SEQUENCE: 26
ggccggccta cagtatgagc ggagaattaa gggagtcacg                          40

<210> SEQ ID NO 27
<211> LENGTH: 44
<212> TYPE: DNA
<213> ORGANISM: Artificial sequence
<220> FEATURE:
<223> OTHER INFORMATION: Synthetic sequence: Oligonucleotide
      pBD-NPTII-FseI-R

<400> SEQUENCE: 27
ggccggccta cagtcccgat ctagtaacat agatgacacc gcgc                     44

<210> SEQ ID NO 28
<211> LENGTH: 35
<212> TYPE: DNA
<213> ORGANISM: Artificial sequence
<220> FEATURE:
<223> OTHER INFORMATION: Synthetic sequence: Oligonucleotide P19-R43W-F

<400> SEQUENCE: 28
cgagttggac tgagtggtgg ctacataacg atgag                               35

<210> SEQ ID NO 29
<211> LENGTH: 35
<212> TYPE: DNA
<213> ORGANISM: Artificial sequence
<220> FEATURE:
<223> OTHER INFORMATION: Synthetic sequence: Oligonucleotide P19-R43W-R

<400> SEQUENCE: 29
ctcatcgtta tgtagccacc actcagtcca actcg                               35

<210> SEQ ID NO 30
<211> LENGTH: 33
<212> TYPE: DNA
<213> ORGANISM: Artificial sequence
<220> FEATURE:
<223> OTHER INFORMATION: Synthetic sequence: Oligonucleotide
      P19-deltaNruI-F

<400> SEQUENCE: 30
ccgtttctgg agggtctcga actcttcagc atc                                 33

<210> SEQ ID NO 31
<211> LENGTH: 33
<212> TYPE: DNA
<213> ORGANISM: Artificial sequence
<220> FEATURE:
<223> OTHER INFORMATION: Synthetic sequence: Oligonucleotide
      P19-deltaNruI-R

<400> SEQUENCE: 31
gatgctgaag agttcgagac cctccagaaa cgg                                 33

<210> SEQ ID NO 32
<211> LENGTH: 57
<212> TYPE: DNA
<213> ORGANISM: Artificial sequence
<220> FEATURE:
<223> OTHER INFORMATION: Synthetic sequence: Oligonucleotide POW-F

<400> SEQUENCE: 32
cgaccggtat gcatcaccat caccatcatc ccgggcatca ccatcaccat cactagc    57

<210> SEQ ID NO 33
<211> LENGTH: 62
<212> TYPE: DNA
<213> ORGANISM: Artificial sequence
<220> FEATURE:
<223> OTHER INFORMATION: Synthetic sequence: Oligonucleotide POW-R

<400> SEQUENCE: 33
tcgagctagt gatggtgatg gtgatgcccg ggatgatggt gatggtgatg cataccggtt    60
cg    62

<210> SEQ ID NO 34
<211> LENGTH: 33
<212> TYPE: DNA
<213> ORGANISM: Artificial sequence
<220> FEATURE:
<223> OTHER INFORMATION: Synthetic sequence: Oligonucleotide GFP-AgeI-F

<400> SEQUENCE: 34
atcggaccgg tatgactagc aaaggagaag aac    33

<210> SEQ ID NO 35
<211> LENGTH: 38
<212> TYPE: DNA
<213> ORGANISM: Artificial sequence
<220> FEATURE:
<223> OTHER INFORMATION: Synthetic sequence: Oligonucleotide GFP-XmaI-F

<400> SEQUENCE: 35
atccgacccg ggactagcaa aggagaagaa cttttcac    38

<210> SEQ ID NO 36
<211> LENGTH: 33
<212> TYPE: DNA
<213> ORGANISM: Artificial sequence
<220> FEATURE:
<223> OTHER INFORMATION: Synthetic sequence: Oligonucleotide GFP-XmaI-R

<400> SEQUENCE: 36
atccgacccg ggtttgtata gttcatccat gcc    33

<210> SEQ ID NO 37
<211> LENGTH: 35
<212> TYPE: DNA
<213> ORGANISM: Artificial sequence
<220> FEATURE:
<223> OTHER INFORMATION: Synthetic sequence: Oligonucleotide GFP-XhoI-R

<400> SEQUENCE: 37
cgatcctcga gttatttgta tagttcatcc atgcc    35